(12) United States Patent
Gao et al.

(10) Patent No.: US 11,376,324 B2
(45) Date of Patent: Jul. 5, 2022

(54) STING ACTIVATING NANOVACCINE FOR IMMUNOTHERAPY

(71) Applicant: The Board of Regents of the University of Texas System, Austin, TX (US)

(72) Inventors: Jinming Gao, Plano, TX (US); Zhijian Chen, Dallas, TX (US); Min Luo, Irving, TX (US); Zhaohui Wang, Dallas, TX (US); Hua Wang, Irving, TX (US); Haocheng Cai, Dallas, TX (US); Gang Huang, Plano, TX (US); Yang-Xin Fu, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 4 days.

(21) Appl. No.: 16/081,911

(22) PCT Filed: Mar. 2, 2017

(86) PCT No.: PCT/US2017/020451
§ 371 (c)(1),
(2) Date: Sep. 2, 2018

(87) PCT Pub. No.: WO2017/151922
PCT Pub. Date: Sep. 8, 2017

(65) Prior Publication Data
US 2019/0060446 A1  Feb. 28, 2019

Related U.S. Application Data

(60) Provisional application No. 62/302,637, filed on Mar. 2, 2016.

(51) Int. Cl.
*A61K 39/39* (2006.01)
*A61K 39/00* (2006.01)
(Continued)

(52) U.S. Cl.
CPC ............ *A61K 39/39* (2013.01); *A61K 9/0019* (2013.01); *A61K 9/5138* (2013.01);
(Continued)

(58) Field of Classification Search
None
See application file for complete search history.

(56) References Cited

U.S. PATENT DOCUMENTS

| 4,435,386 A | 3/1984 | Ribi et al. |
| 4,436,727 A | 3/1984 | Ribi |

(Continued)

FOREIGN PATENT DOCUMENTS

| WO | WO 1991/016347 | 10/1991 |
| WO | WO 2000/061543 | 10/2000 |

(Continued)

OTHER PUBLICATIONS

MC Hanson et al. "Nanoparticulate STING agonists are potent lymph node-targeted vaccine adjuvants." The Journal of Clinical Investigation, vol. 125 No. 6 Jun. 2015, pp. 2532-2546. (Year: 2015).*

(Continued)

*Primary Examiner* — Isaac Shomer
(74) *Attorney, Agent, or Firm* — Parker Highlander PLLC

(57) ABSTRACT

In some aspects, the present disclosure provides vaccine compositions comprising an antigen and a diblock copolymer wherein the diblock copolymer is pH responsive. In some embodiments, these compositions activate the STING and/or the interferon receptor pathways. In some embodiments, the diblock copolymer hits a pKa from about 6 to about 7.5. Also provided herein are methods of treatment using these compositions to treat an infectious disease or cancer.

23 Claims, 23 Drawing Sheets
Specification includes a Sequence Listing.

(51) Int. Cl.

| | |
|---|---|
| *A61K 9/51* | (2006.01) |
| *A61K 47/32* | (2006.01) |
| *A61K 47/58* | (2017.01) |
| *B82Y 5/00* | (2011.01) |
| *A61K 9/00* | (2006.01) |
| *A61K 45/06* | (2006.01) |
| *A61K 39/145* | (2006.01) |

(52) U.S. Cl.
CPC ........ *A61K 9/5146* (2013.01); *A61K 39/0011* (2013.01); *A61K 39/00119* (2018.08); *A61K 39/001168* (2018.08); *A61K 39/145* (2013.01); *A61K 45/06* (2013.01); *A61K 47/32* (2013.01); *A61K 47/58* (2017.08); *A61K 2039/55555* (2013.01); *B82Y 5/00* (2013.01); *Y02A 50/30* (2018.01)

(56) References Cited

U.S. PATENT DOCUMENTS

| | | | |
|---|---|---|---|
| 4,436,728 | A | 3/1984 | Ribi et al. |
| 4,505,899 | A | 3/1985 | Ribi et al. |
| 4,505,900 | A | 3/1985 | Ribi et al. |
| 4,520,019 | A | 5/1985 | Ribi et al. |
| 4,866,034 | A | 9/1989 | Ribi |
| 4,877,611 | A | 10/1989 | Cantrell |
| 4,950,645 | A | 8/1990 | Vosika et al. |
| 5,980,912 | A | 11/1999 | Podolski et al. |
| 10,098,971 | B2 * | 10/2018 | Gao .............. G01N 21/6456 |
| 11,013,818 | B2 * | 5/2021 | Gao .............. G01N 21/6456 |
| 11,096,899 | B2 * | 8/2021 | Gong ................ A61K 9/5138 |
| 2008/0095810 | A1 * | 4/2008 | Alonso Fernandez ................. A61K 9/5161 424/401 |
| 2009/0165152 | A1 * | 6/2009 | Jaffee ................ A61K 39/0011 800/3 |
| 2009/0191227 | A1 | 7/2009 | Hartikka et al. |
| 2010/0062968 | A1 * | 3/2010 | Pulendran ............. A61P 37/02 514/20.1 |
| 2010/0112078 | A1 | 5/2010 | Panda et al. |
| 2011/0065807 | A1 | 3/2011 | Radovic-Moreno et al. |
| 2012/0076752 | A1 | 3/2012 | Wu et al. |
| 2013/0330278 | A1 * | 12/2013 | Gao .................. A61K 49/0082 424/9.6 |
| 2014/0308363 | A1 * | 10/2014 | Zale ................... A61K 9/1647 424/501 |

FOREIGN PATENT DOCUMENTS

| | | |
|---|---|---|
| WO | WO 2002/030930 | 4/2002 |
| WO | WO 2014/093936 | 6/2014 |
| WO | WO 2015/095340 | 6/2015 |

OTHER PUBLICATIONS

H Zhang et al. "Cell-free Tumor Microparticle Vaccines Stimulate Dendritic Cells via cGAS/STING Signaling." Cancer Immunol Res; 3(2) Feb. 2015, pp. 196-205. (Year: 2015).*

Qiang Cheng et al. "The effect of guanidinylation of PEGylated poly(2-aminoethyl methacrylate) on the systemic delivery of siRNA." Biomaterials, vol. 34, 2013, pp. 3120-3131. (Year: 2013).*

Rupei Tang, R. Noelle Palumbo, Lakshmi Nagarajan, Emily Krogstad, Chun Wang. "Well-defined block copolymers for gene delivery to dendritic cells: Probing the effect of polycation chain-length." Journal of Controlled Release, vol. 142, 2010, pp. 229-237. (Year: 2010).*

Lei Miao, C. Michael Lin, and Leaf Huang. "Stromal barriers and strategies for the delivery of nanomedicine to desmoplastic tumors." Journal of Controlled Release, vol. 219 (2015), pp. 192-204. (Year: 2015).*

Cohen et al., "T-cell activation by antigen-loaded pH-sensitive hydrogel particles in vivo: the effect of particle size," *Bioconjugate Chem.*, 20:111-119, 2009.

Extended European Search Report issued in European Application No. 17760821.3, dated Oct. 23, 2019.

Pohlit et al., "Biodegradable pH-Sensitive Poly(ethylene glycol) Nanocarriers for Allergen Encapsulation and Controlled Release," *Biomacromolecules*, 16(10):3103-3111, 2015.

Tang et al., "Block copolymer micelles with acid-labile ortho ester side-chains: Synthesis, characterization, and enhanced drug delivery to human glioma cells," *Journal of Controlled Release*, 151:18-27, 2011.

Trimaille and Verrier, "Micelle-Based Adjuvants for Subunit Vaccine Delivery," *Vaccines*, 3:803-813, 2015.

Wilson et al., "Enhancement of MHC-I antigen presentation via architectural control of pH-responsive, endosomolytic polymer nanoparticles," *The AAPS Journal*, 17(2):358-369, 2015.

Adams, et al., "Effective polymer adjuvants for sustained delivery of protein subunit vaccines", *Acta Biomaterialia*, 14:104-114, 2015.

Adel-Patient et al., "Block Copolymers Have Differing Adjuvant Effects on the Primary Immune Response Elicited by Genetic Immunization and on Further Induced Allergy", *Clin. Vaccine Immunol.*, 17(1):36-42, 2010.

Azuma et al., "Correlations of in vivo growth of CTL-susceptible and-resistant variant tumor cell lines in CTL-responder AKR. H-2b: Fv-1b and-nonresponder AKR. H-2b mice", *Cell Immunol.*, 116(1): 123-134, 1988.

Benjamini et al., "Isolation and characterization of the neutralizable epitope of simian retrovirus-1 (SRV-1) and of the cell receptor for the virus", *Adv. Exp. Med. Biol.*, 303:71-77, 1991.

Bisht et al., "Biological response modifiers: Current use and future prospects in cancer therapy", *Indian J. Cancer*, 47(4):443-451, 2010.

Carvalho et al., "Malaria vaccine: candidate antigens, mechanisms, constraints and prospects", *Scan. J. Immunol.*, 56:327, 2002.

Chen and Mellman, "Oncology meets immunology: the cancer-immunity cycle", *Immunity*, 39:1-10, 2013.

De Taeye et al., "HIV-1 envelope trimer design and immunization strategies to induce broadly neutralizing antibodies", *Trends Immunol.*, 37(3):221-232, 2016.

Gupta and Kanodia, "Biological response modifiers in cancer therapy", *Natl. Med. J. India*, 15(4):202-207, 2002.

Hilgers et al., "Alkyl-esters of polyacrylic acid as vaccine adjuvants", *Vaccine*, 16(16):1575-1581, 1998.

Hubbell et al., "Materials engineering for immuno modulation", *Nature*, 462:449-460, 2009.

Husson et al., "Gene replacement and expression of foreign DNA in mycobacteria", *J. Bacteriol.*, 172(2):519-524, 1990.

International Preliminary Report on Patentability issued in corresponding PCT Application No. PCT/US2017/020451, dated Sep. 13, 2018.

International Search Report and Written Opinion issued in corresponding PCT Application No. PCT/US2017/020451, dated May 25, 2017.

Jacobs et al., "Introduction of foreign DNA into mycobacteria using a shuttle phasmid", *Nature*, 327(6122):532-535, 1987.

Lotte et al., "A bibliography of the complications of BCG vaccination. A comprehensive list of the world literature since the introduction of BCG up to Jul. 1982, supplemented by over 100 personal communications", *Adv. Tuberc. Res.*, 21:194-245, 1984.

Lotte et al., "BCG complications. Estimates of the risks among vaccinated subjects and statistical analysis of their main characteristics", *Adv. Tuberc. Res.*, 21:107-193, 1984.

Luelmo, "BCG vaccination", *Am. Rev. Respir. Dis.*, 125(3 Pt2):70-72, 1982.

Martin et al., "Transposition of an antibiotic resistance element in mycobacteria", *Nature*, 345(6277):739-743, 1990.

Nguyen et al., "Lipid-derived nanoparticles for immunostimulatory RNA adjuvant delivery", *Proc. Natl. Acad. Sci.*, 109(14):E797-E803, 2012.

Ottenhoff and Kaufmann, "Vaccines against Tuberculosis: Where Are We and Where Do We Need to Go?", *PLoS Pathogen*, 8:e1002607, 2012.

(56) References Cited

OTHER PUBLICATIONS

Rabinovich et al., "Vaccine technologies: view to the future", *Science*, 265(5177): 1401-1404, 1994.

Rosenberg and Restifo, "Adoptive cell transfer as personalized immunotherapy for human cancer", *Science*, 348:62-68, 2015.

Snapper et al., "Lysogeny and transformation in mycobacteria: stable expression of foreign genes", *Proc. Natl. Acad. Sci. USA*, 85(18):6987-6991, 1988.

Takada et al., "Identification of varicella-zoster virus strains by PCR analysis of three repeat elements and a PstI-site-less region", *J. Clin. Microbiol.*, 33(3):658-660, 1995.

Tumeh et al., "PD-1 blockade induces responses by inhibiting adaptive immune resistance", *Nature*, 515:568-571, 2014.

Yamamoto et al., "In vitro Augmentation of Natural Killer Cell Activity and Production of Interferon-$\alpha/\beta$ and -$\gamma$ with Deoxyribonucleic Acid Fraction from *Mycobacterium bovis* BCG", *Jpn. J. Cancer Res.*, 79:866-873, 1988.

Yin et al., "Effect of various adjuvants on the antibody response of mice to pneumococcal polysaccharides", *J. Biol. Resp. Modif.*, 8:190-205, 1989.

Zhou et al., "Multicolored pH-tunable and activatable fluorescence nanoplatform responsive to physiologic pH stimuli", *J Am Chem Soc*, 134:7803-7811, 2012.

Zhou et al., "Tunable, ultrasensitive pH—responsive nanoparticles targeting specific endocytic organelles in living cells", *Angew Chem Int Ed Engl*, 50:6109-6114, 2011.

Luo et al., "A self-assembled, modular DNA delivery system mediated by silica nanoparticles", *J. Control. Rel.*, 95:333-341, 2004.

Ma et al., "Ultra-pH-sensitive nanoprobe library with broad pH tunability and fluorescence emissions," *J. Am. Chem. Soc.*, 136:11085-11092, 2014.

Office Action issued in Japanese Application No. 2018-545910, dated Mar. 15, 2021, and English language translation thereof.

* cited by examiner

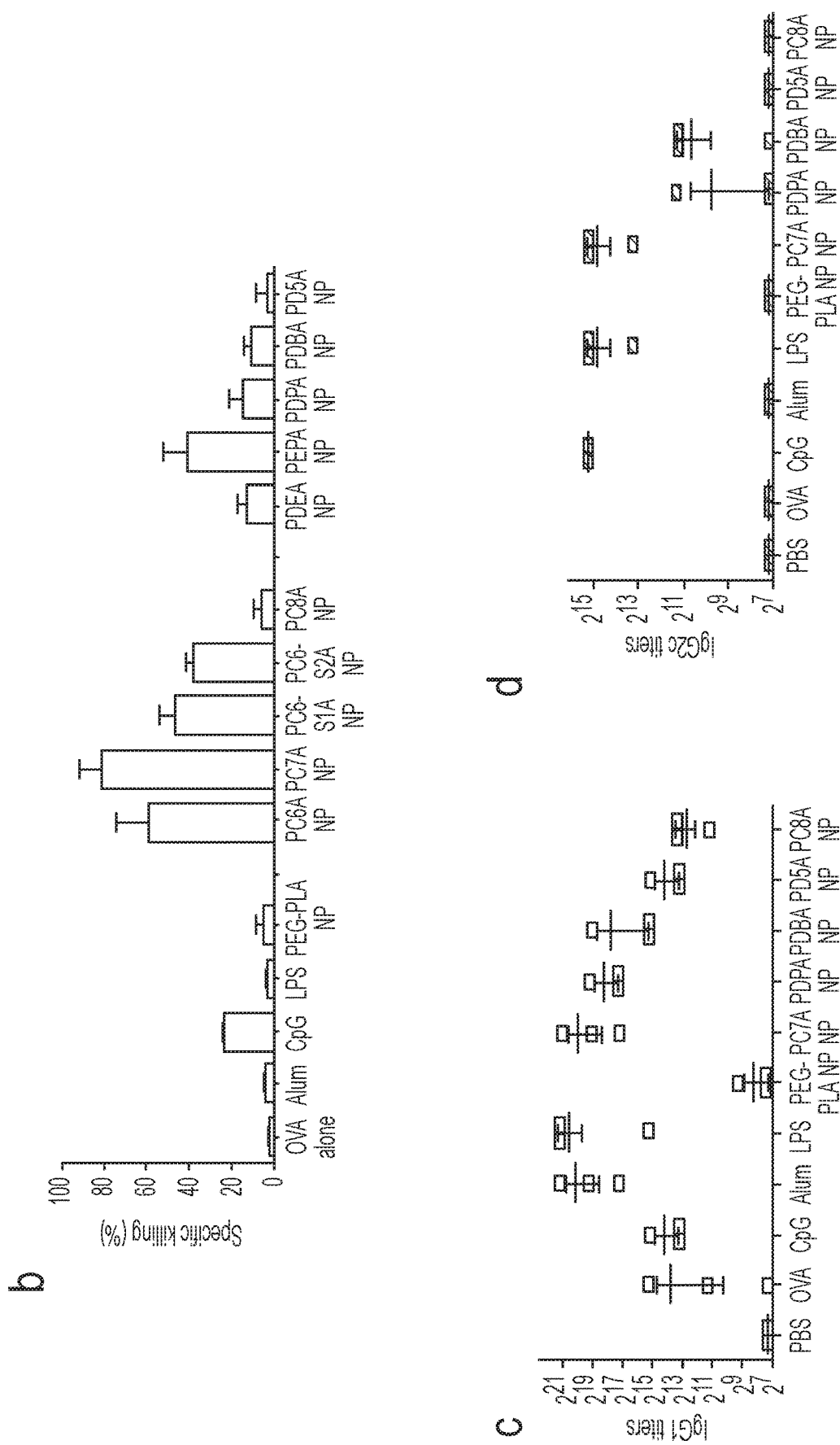
FIG. 1B-D

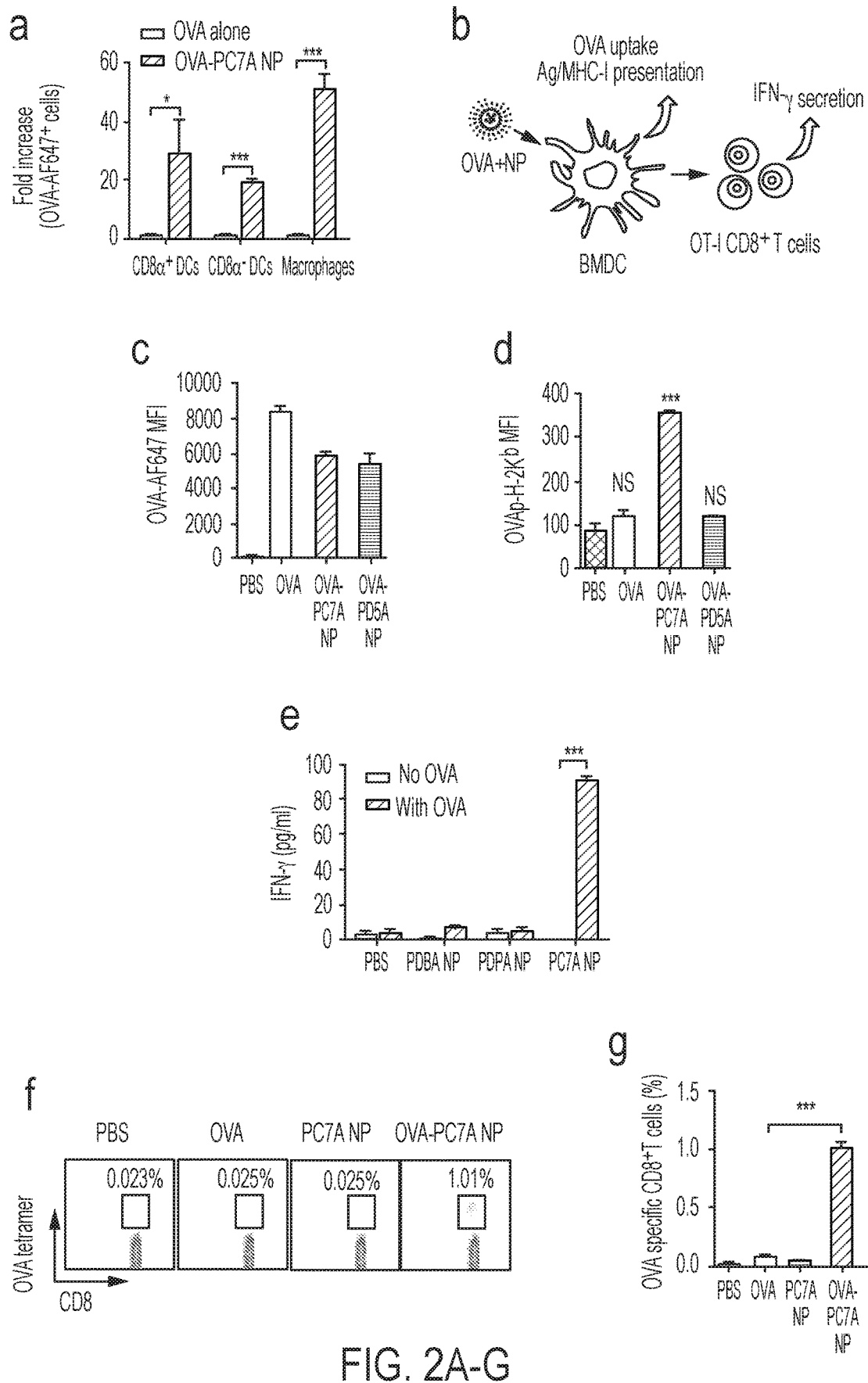
FIG. 2A-G

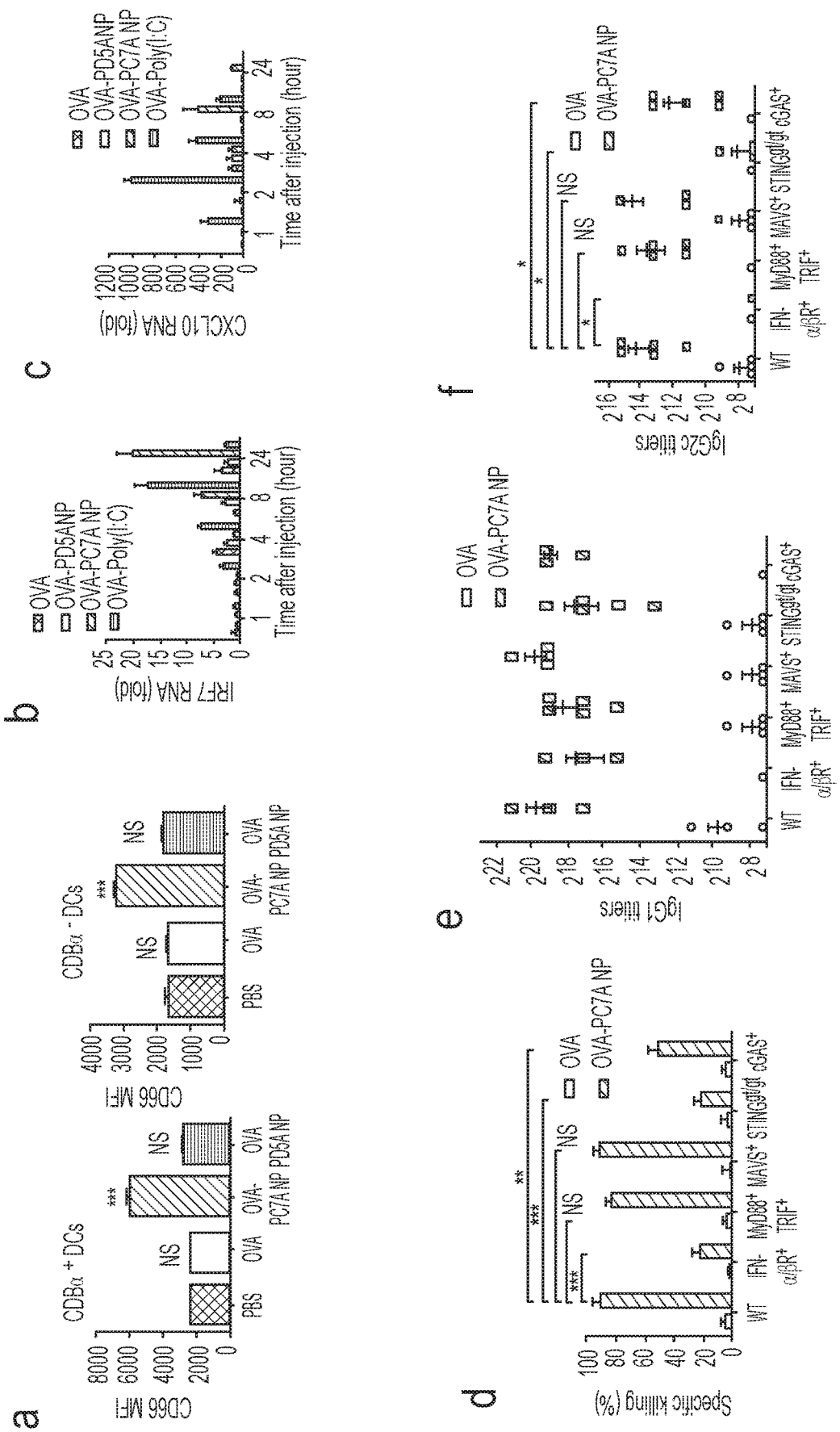
FIG. 3A-F

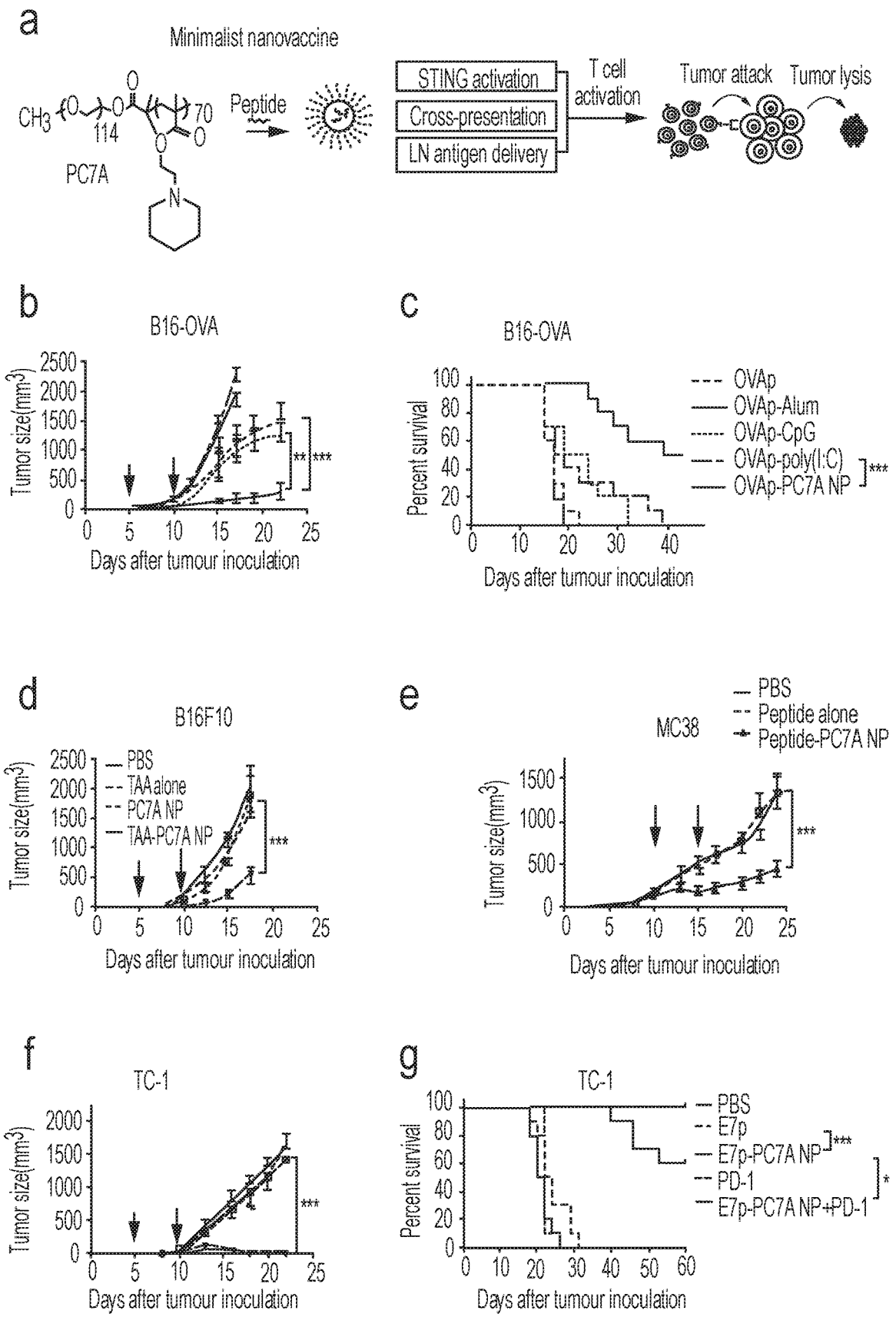
FIG. 4A-G a
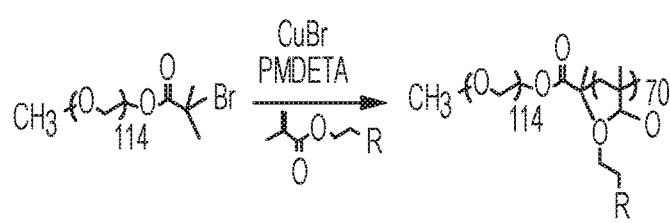
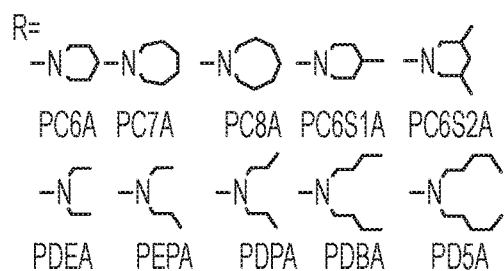
b
| Polymer | Mn (kDa) | PDI | pKa | D$_h$(nm) |
|---|---|---|---|---|
| PDEA | 20.3 | 1.14 | 7.81 | 6.4±1.0 |
| PEPA | 20.2 | 1.12 | 6.95 | 23.3±5.8 |
| PDPA | 20.1 | 1.12 | 6.24 | 31.4±3.7 |
| PDBA | 22.1 | 1.12 | 5.34 | 45.6±3.3 |
| PD5A | 21.1 | 1.17 | 4.38 | 60.6±7.3 |
| PC6A | 19.7 | 1.20 | 7.29 | 23.2±2.6 |
| PC7A | 20.9 | 1.29 | 6.97 | 32.4±2.0 |
| PC8A | 13.4 | 1.25 | 5.65 | 41.4±2.3 |
| PC6S1A | 22.1 | 1.36 | 6.88 | 26.2±1.6 |
| PC6S2A | 21.8 | 1.34 | 6.05 | 30.4±2.3 |
c
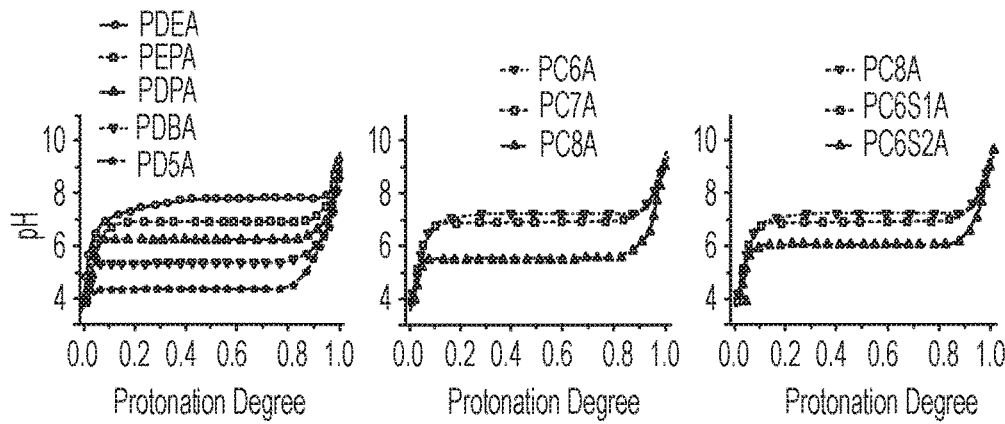
FIG. 5A-C

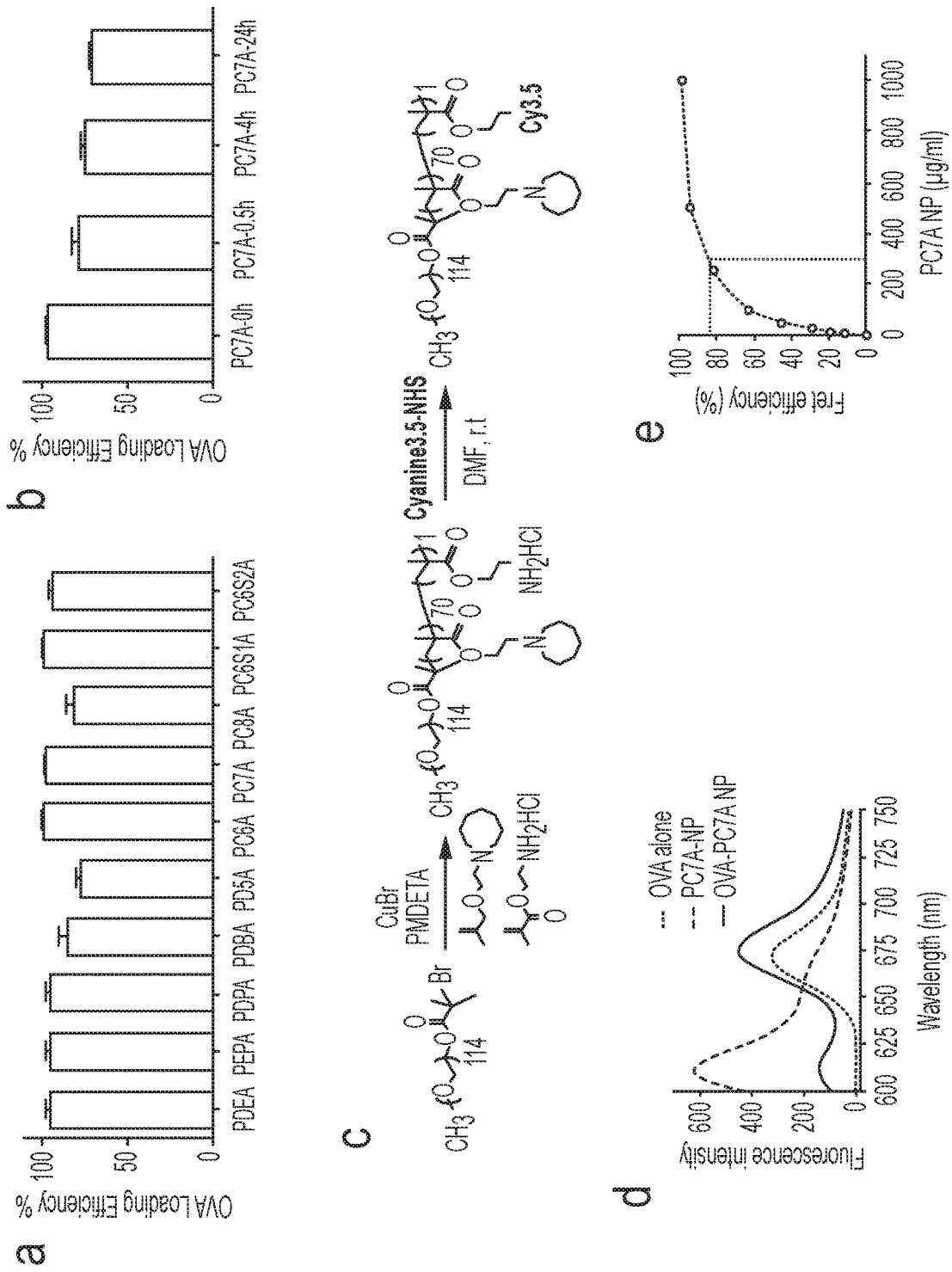
FIG. 6A-E

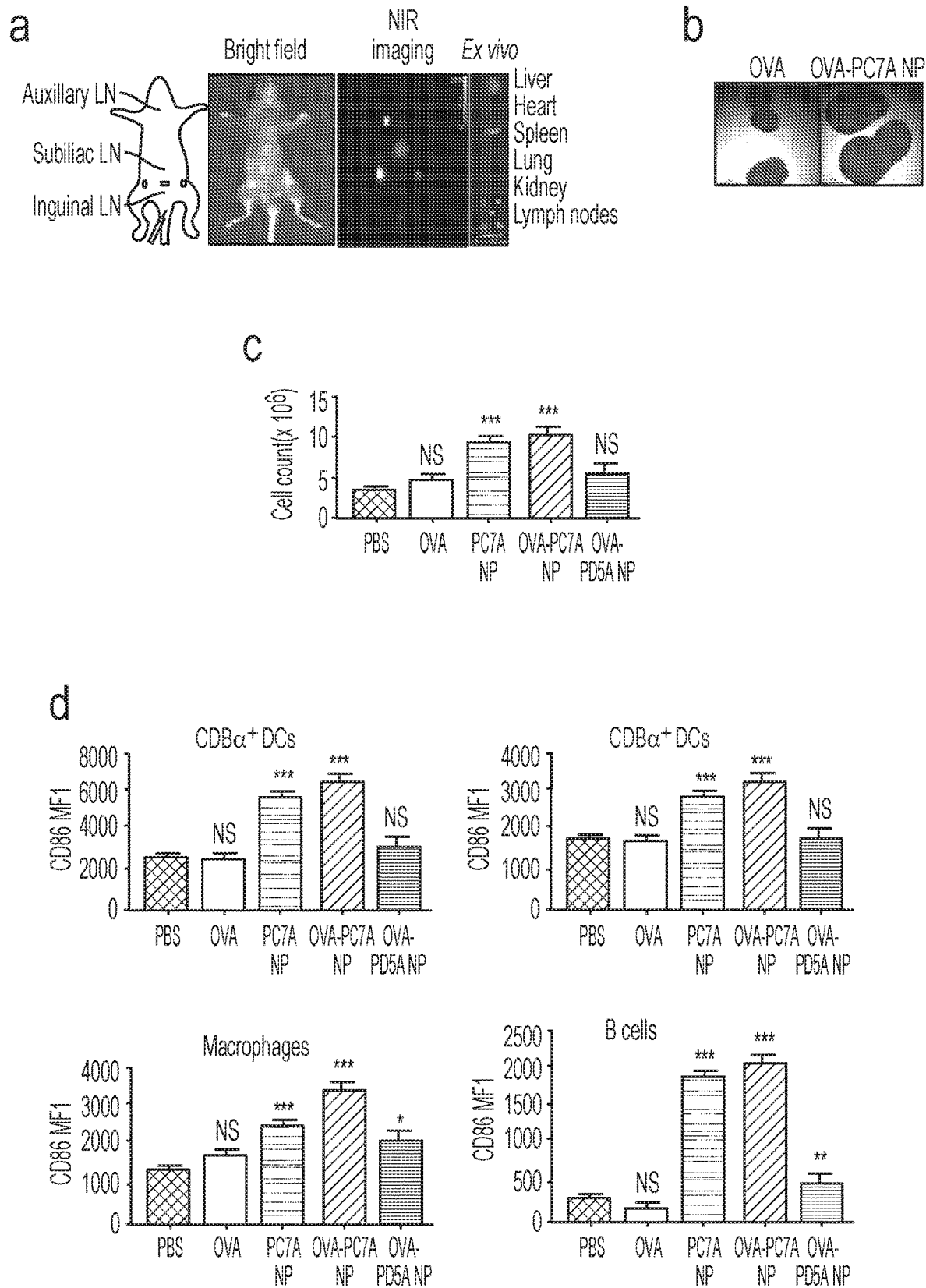
FIG. 7A-D

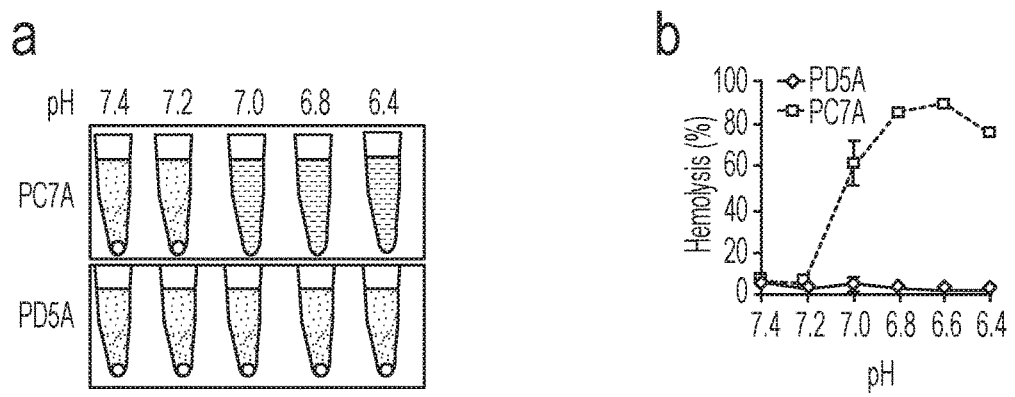
FIG. 8A-B
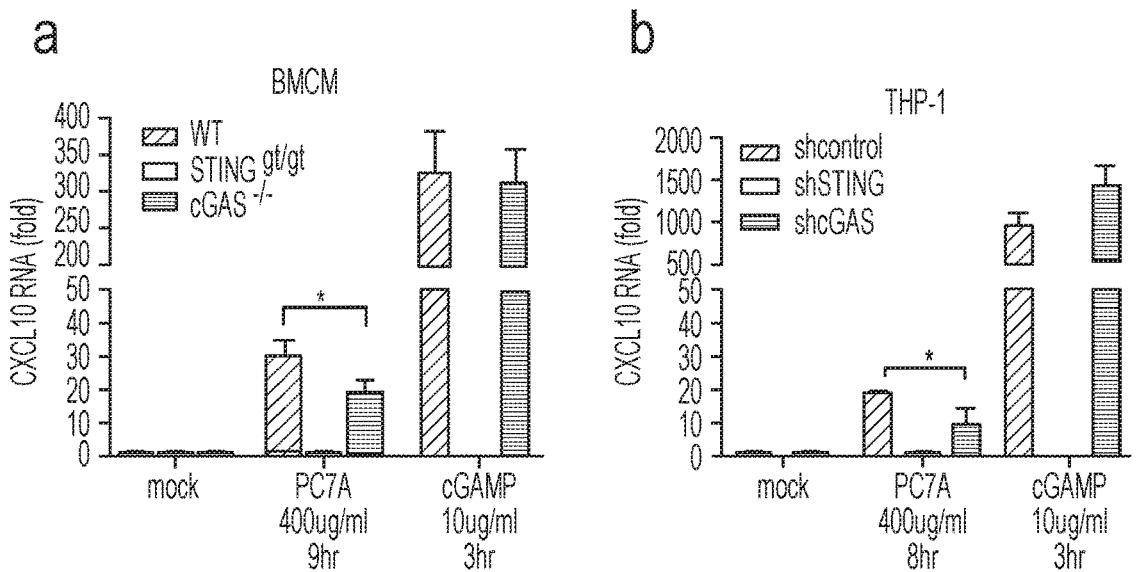
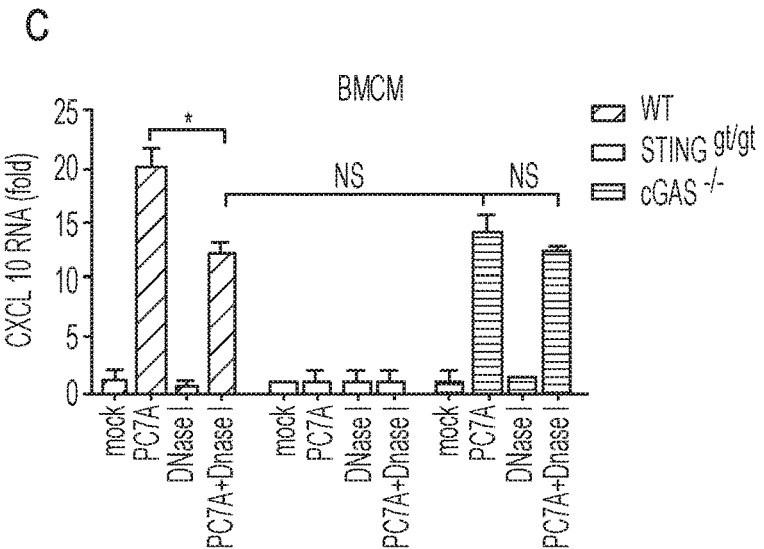
FIG. 9A-C

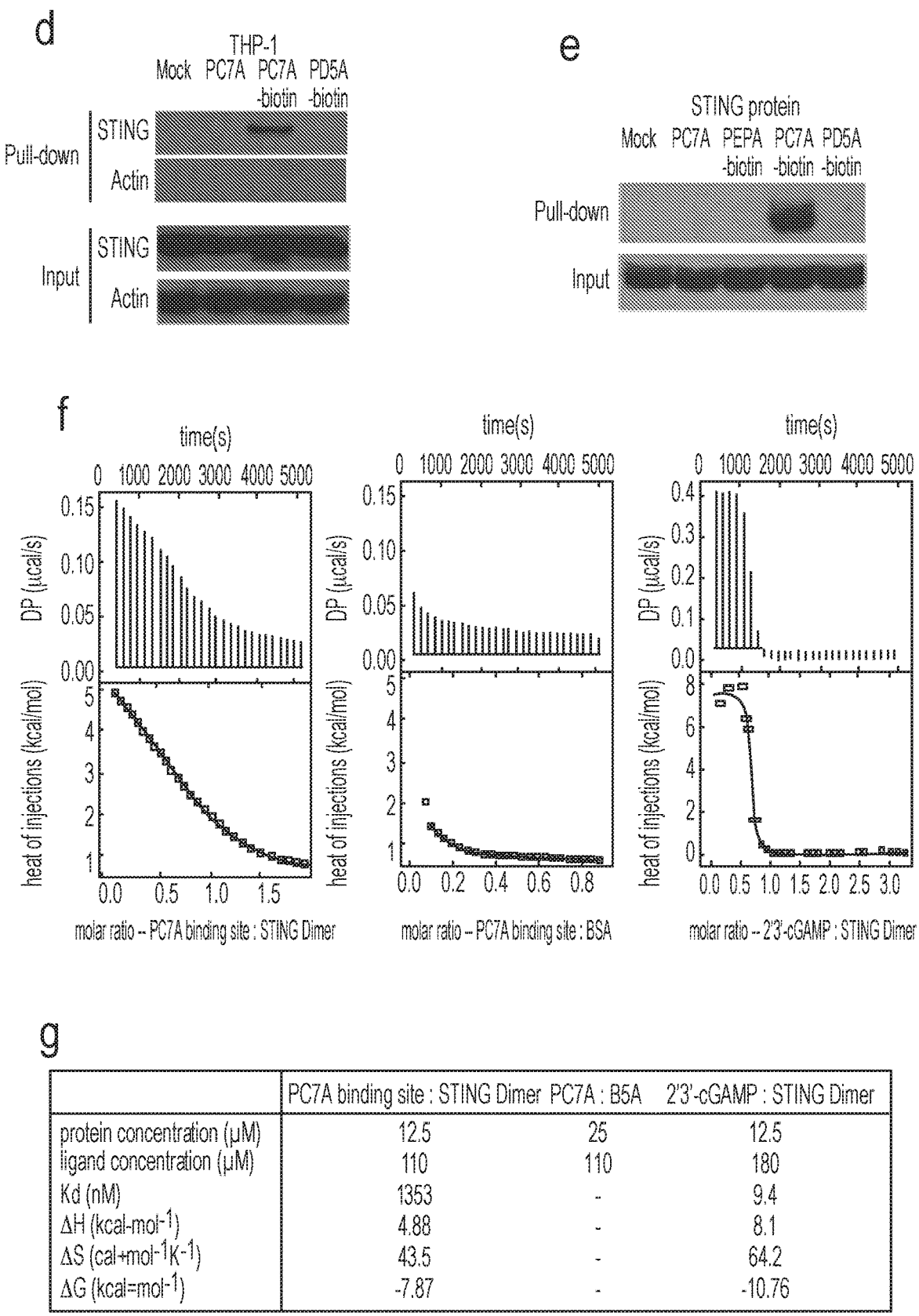
FIG. 9D-G

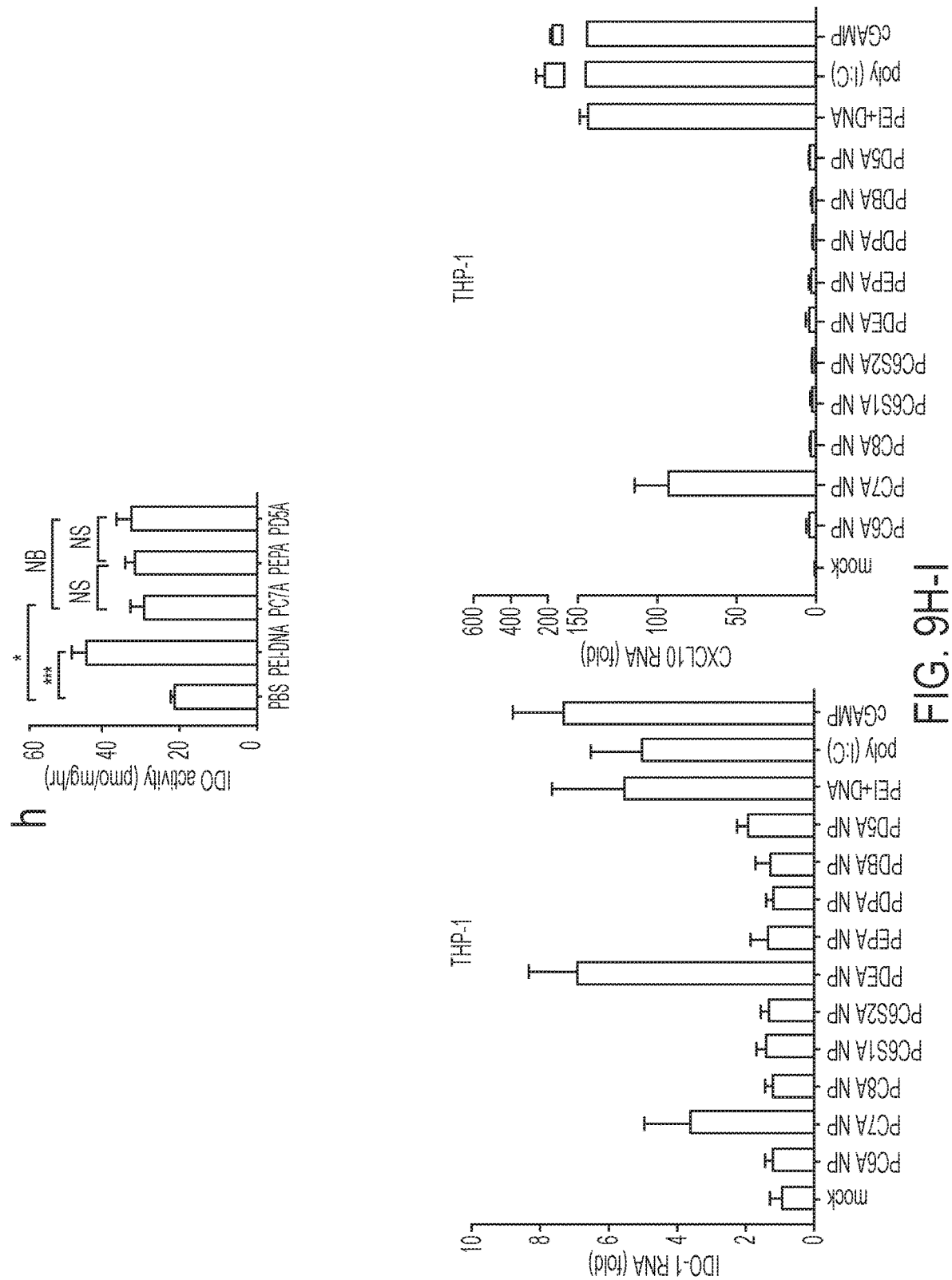
FIG. 9H-I

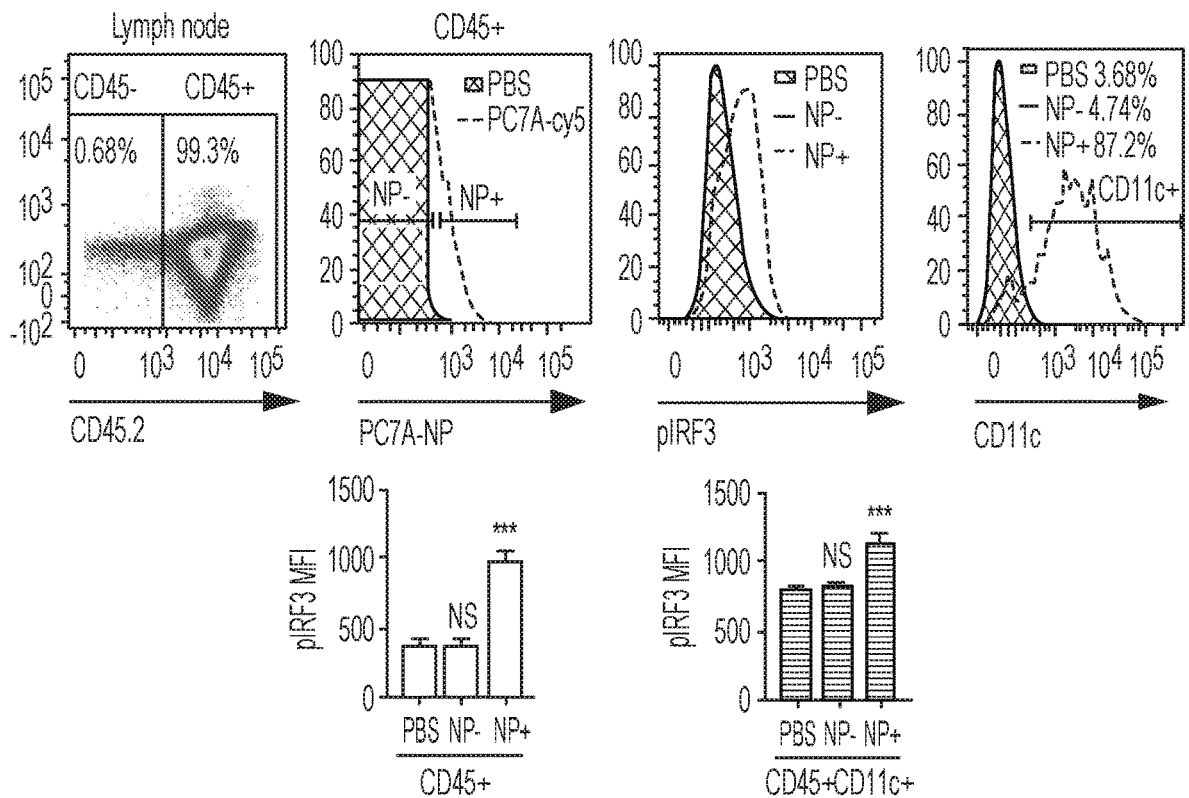
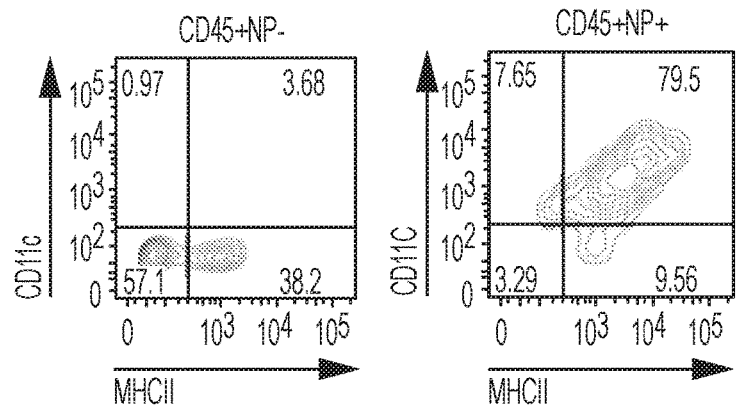
FIG. 10A-B

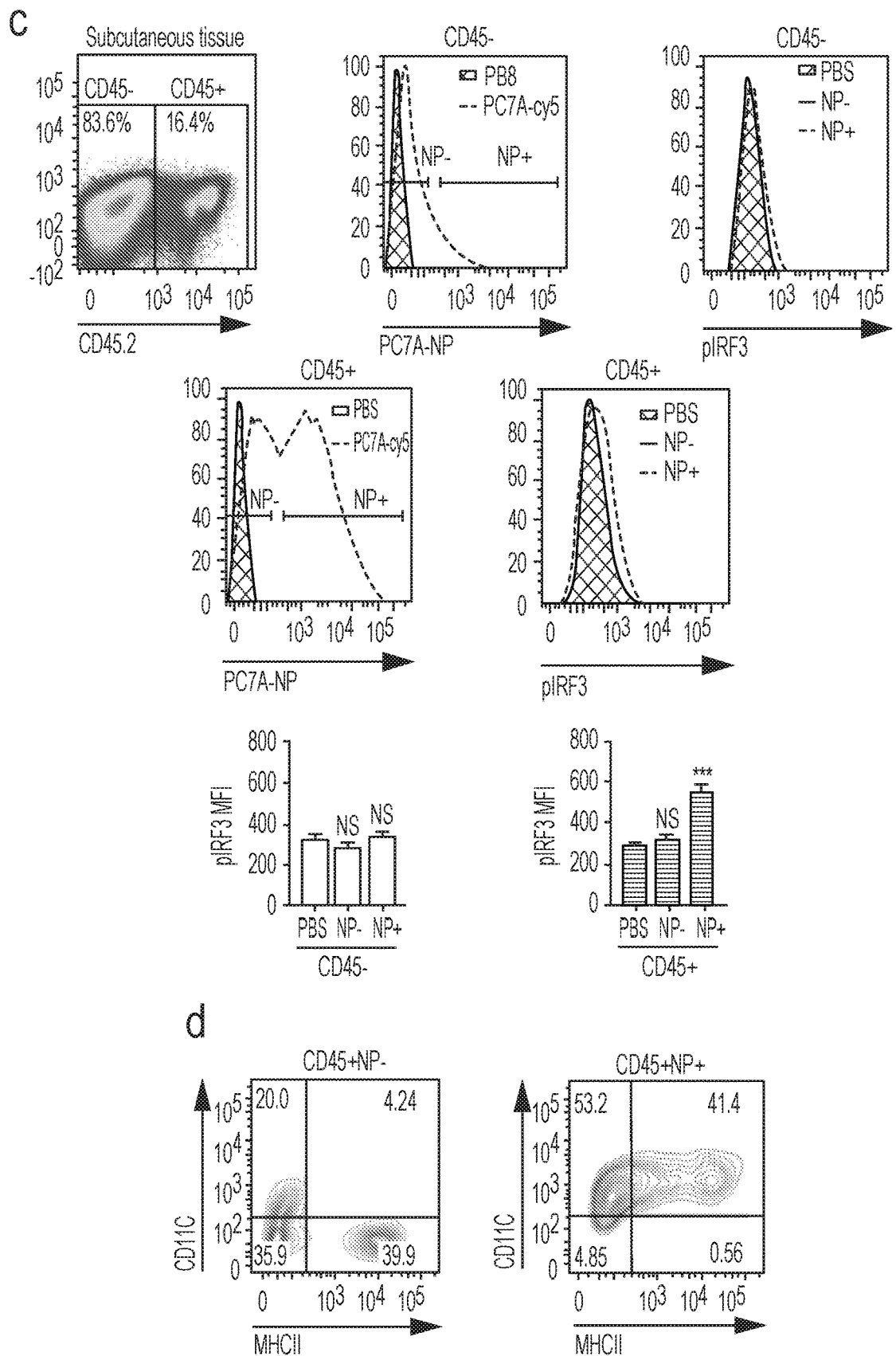
FIG. 10C-D

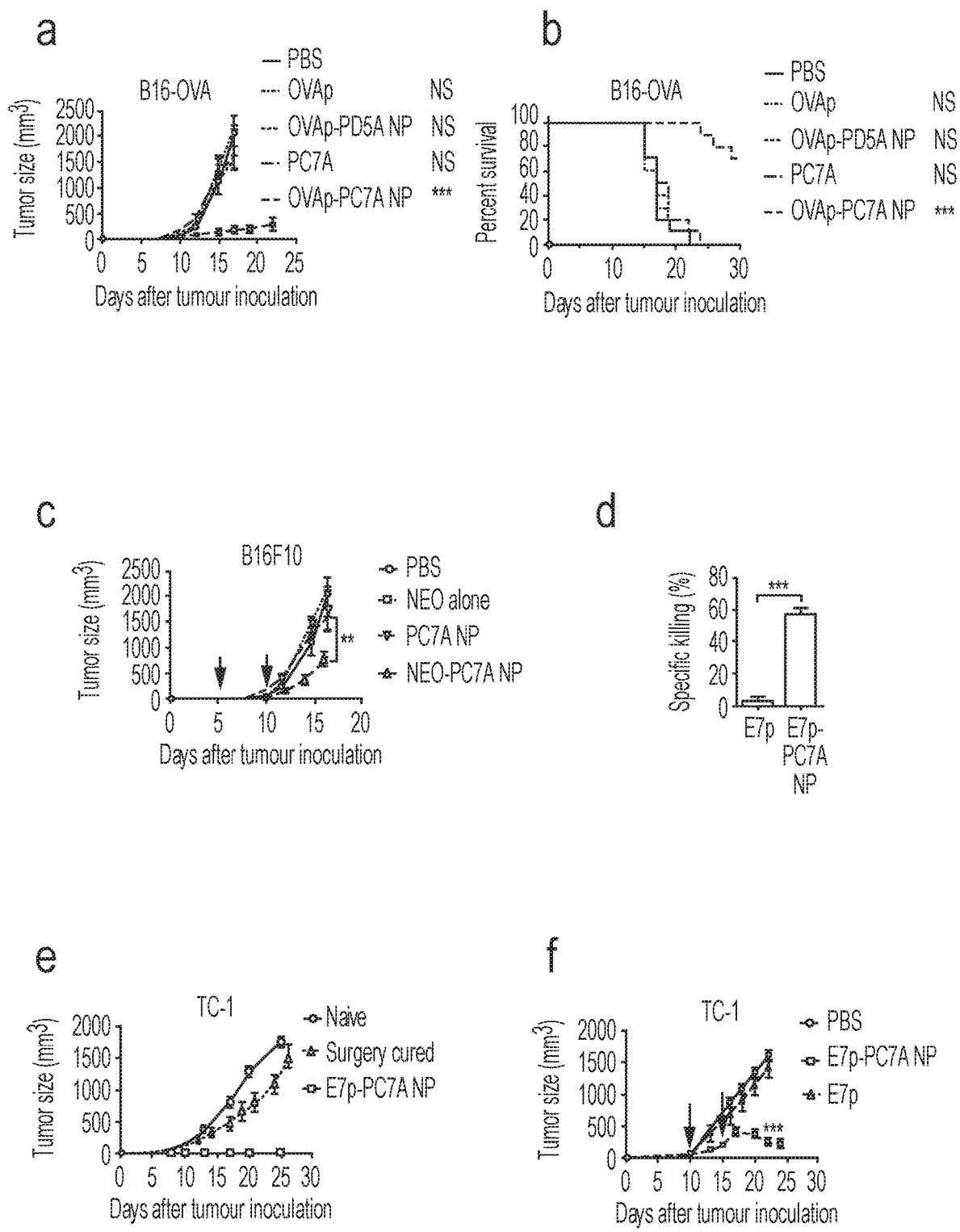
FIG. 11A-F

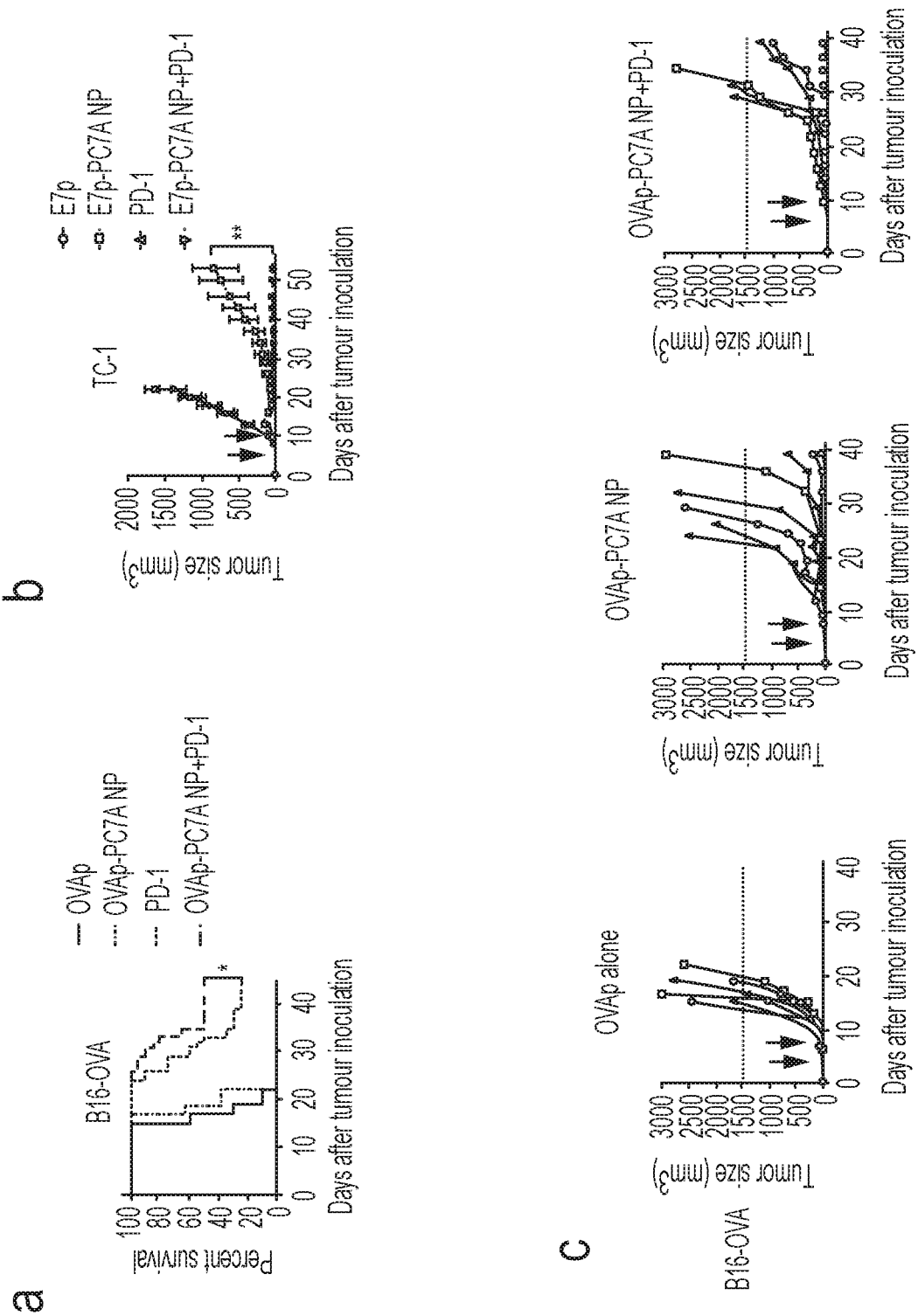
FIG. 12A-C d
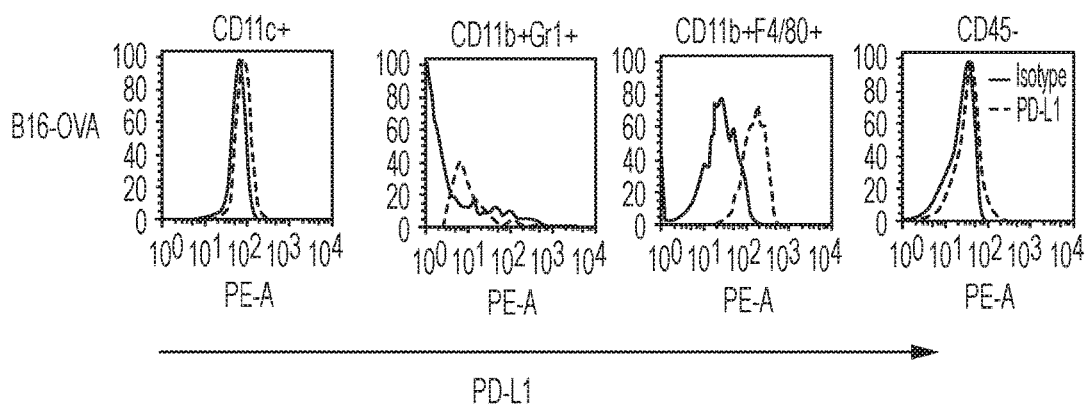
e
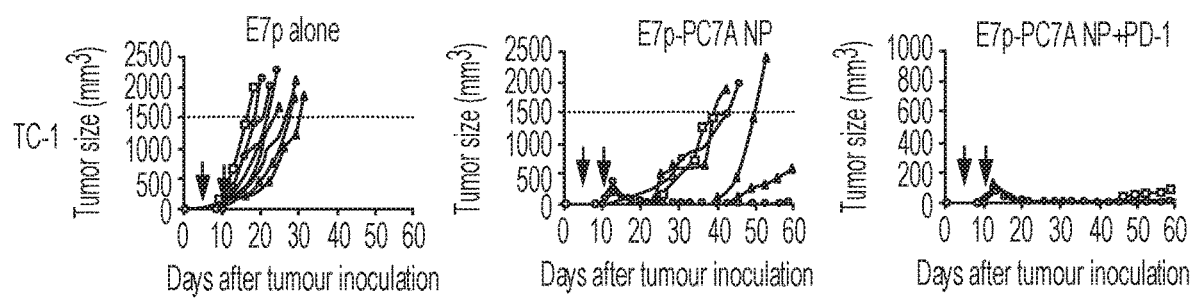
f
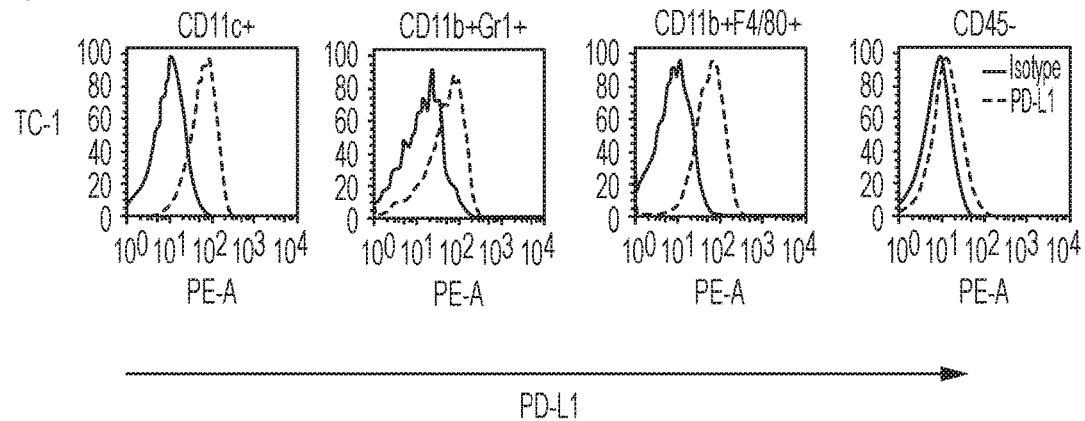
FIG. 12D-F b
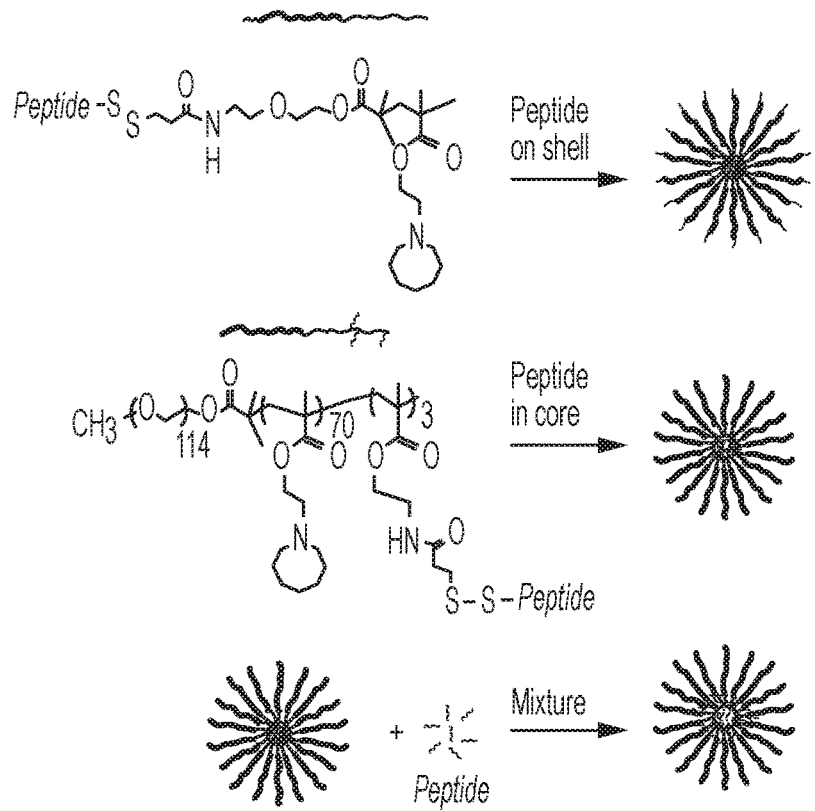
c
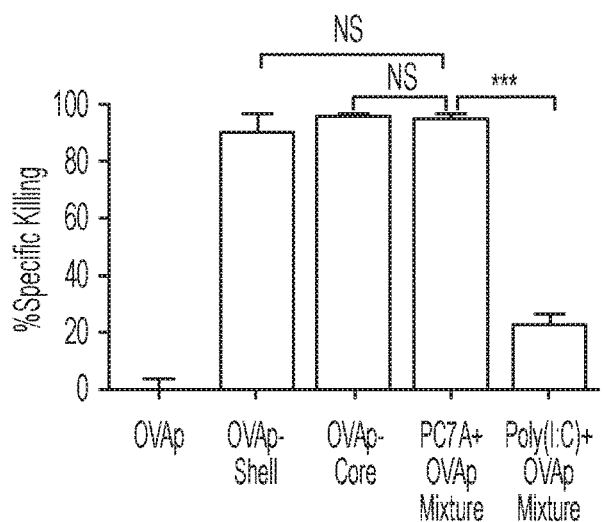
FIG. 16B-C

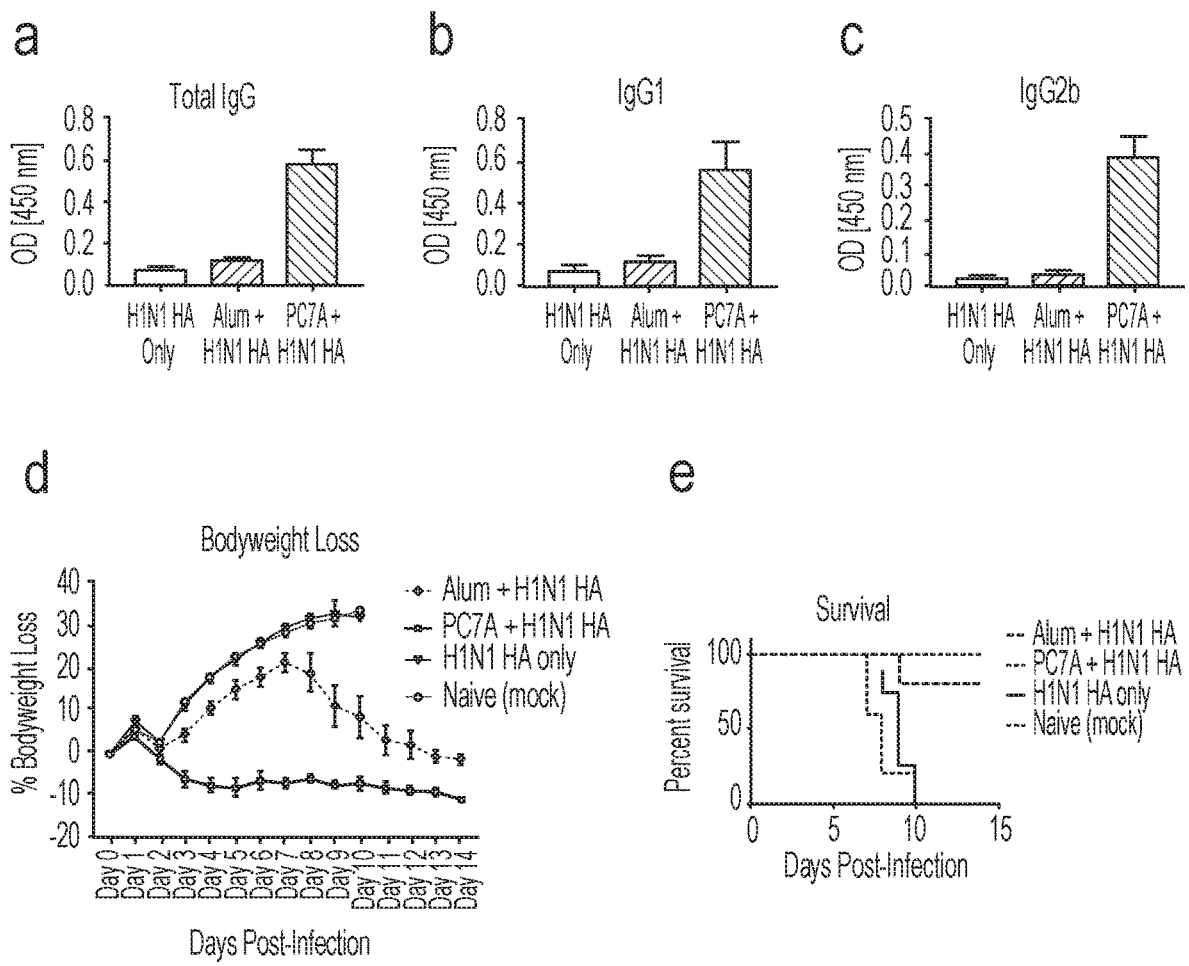
FIG. 17A-E
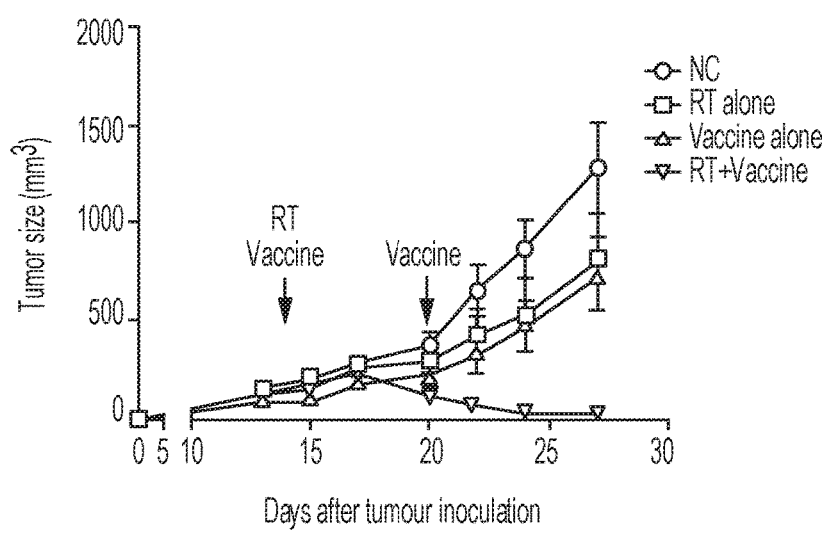
FIG. 18

STING ACTIVATING NANOVACCINE FOR IMMUNOTHERAPY

This application is a national phase application under 35 U.S.C. § 371 of International Application No. PCT/US2017/020451, filed Mar. 2, 2017, which claims benefit of priority to U.S. Provisional Application Ser. No. 62/302,637, filed Mar. 2, 2016, the entire contents of each of which are hereby incorporated by reference.

The invention was made with government support under Grant Nos. R01AI093967, R01EB013149, and R01CA129011 awarded by the National Institutes of Health. The government has certain rights in the invention.

BACKGROUND

1. Field

The present disclosure relates generally to the field of vaccine compositions. More particularly, it concerns vaccine compositions for use in an immunotherapy of cancer or an infectious disease.

2. Description of Related Art

Most cancer cells are only weakly immunogenic. As such, immunotherapies require the use of adjuvants to increase the reaction of the immune system to generate an appropriate immune response. Often, this involves delivery of antigens to promote the development of antibodies for the disease marker. Generation of tumor-specific T cells is critically important for cancer immunotherapy (Rosenberg and Restifo, 2015; Tumeh, et al., 2014). A major challenge in achieving a robust adaptive T cell response is the spatiotemporal orchestration of antigen delivery and cross-presentation in antigen presenting cells (APCs) with innate stimulation (Hubbell, et al., 2009; Abbas, et al., 2014; Chen and Mellman, 2013). Given these and other challenges in the development of vaccines for cancer as well as infectious disease, new vaccine compositions are need.

SUMMARY

In some aspects, the present disclosure provides compositions which may be used to promote an immune response to a disease or disorder via the STING pathway. In some aspects, the present disclosure provides compositions comprising:

(A) an antigen;
(B) a pH sensitive diblock copolymer;

wherein the antigen is encapsulated by the copolymer. In some embodiments, the antigen is an anti-cancer antigen. In some embodiments, the antigen is a tumor-associated antigen or a tumor neoantigen. In some embodiments, the tumor-associated antigen is a human papilloma virus E6 protein, E7 protein, or a fragment thereof such as LHEYMLDLQPETVDLDLLMGTLGIVCPICSQ (SEQ ID NO: 1) or DTPTLHEYMLDLQPETVDLYCYE (SEQ ID NO: 2). In other embodiments, the tumor-associated antigen is mesothelin or a fragment thereof such as GQKMNAQA-IALVACYLRGGGQLDEDMV (SEQ ID NO: 3). In other embodiments, the anti-cancer antigen is a melanoma tumor associated antigen or a neoantigen such as HAS-STFTITDQVPFSVSVSQLQAL (SEQ ID NO: 4), SHEGPAFLTWHRYHLLQLERDMQE (SEQ ID NO: 5), QPQIANCSVYDFFVWLHYYSVRDT (SEQ ID NO: 6), REGVELCPGNKYEMRRHGTTHSLVIHD (SEQ ID NO: 7), DSGSPFPAAVILRDALHMARGLKYLHQ (SEQ ID NO: 8), VVDRNPQFLDPVLAYLMKGLCEKPLAS (SEQ ID NO: 9), PSKPSFQEFVDWENVSPELNSTDQPFL (SEQ ID NO: 10), or NHSGLVTFQAFIDVMSRETTDTD-TADQ (SEQ ID NO: 11). In some embodiments, the anti-cancer antigen is a bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid cancer antigen. In some embodiments, the anti-cancer antigen is a mesothelioma, melanoma, pancreatic, ovarian, or cervical cancer antigen.

In other embodiments, the antigen is a viral antigen. In some embodiments, the viral antigen is a hepatitis B virus antigen such as a HBV surface (HBsAg), core (HBcAg) antigen, or a fragment thereof. In other embodiments, the viral antigen is an influenza virus antigen such as a haemagglutinin antigen (HA), a neuroaminidase antigen (NA), or a fragment thereof. In other embodiments, the viral antigen is a West Nile virus antigen such as an envelope protein (E), a premembrane protein (prM), or a fragment thereof. In other embodiments, the viral antigen is a Dengue virus antigen such as a 80E subunit protein or a fragment thereof. In other embodiments, the viral antigen is an Ebola virus antigen such as a glycoprotein (GP) or fragment thereof. In other embodiments, the viral antigen is a HIV antigen such as a HIV envelope protein gp41, gp120, or a fragment thereof. In other embodiments, the antigen is a bacterial antigen such as a Mycobacterium tuberculosis (Mtb) antigen such as recombinant Ag85A, Ag85B, ESAT6, TB10.4, or a fragment thereof. In other embodiments, the antigen is a malaria antigen such as a circumsporozoite protein (CSP), sporozoite and liver-stage antigen (SALSA), merozoite surface protein (MSP) of *Plasmodium falciparum*, or a fragment thereof.

In some embodiments, the diblock copolymer has a $pK_a$ in water from about 6 to about 7.5 as calculated by pH titration. In some embodiments, the nanoparticle formed from the diblock copolymer is dissociates at a pH below the $pK_a$. In some embodiments, the diblock copolymer comprises a hydrophilic block and a hydrophobic block. In some embodiments, the hydrophilic block is a PEG polymer, a PVP polymer, or a MPC polymer. In some embodiments the hydrophilic block is a PEG polymer. In some embodiments, the hydrophobic block comprises an amine group which has a $pK_a$ from about 6 to about 7.5. In some embodiments, the hydrophobic block becomes hydrophilic upon protonation of the amine group. In some embodiments, the amine group is a cyclic amine group. In some embodiments, the diblock copolymer is further defined by the formula:

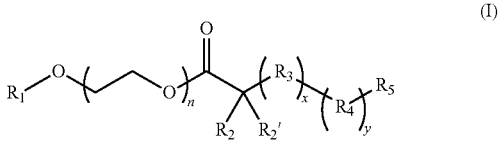

wherein:
R$_1$ is hydrogen, alkyl$_{(C \leq 12)}$, cycloalkyl$_{(C \leq 12)}$, substituted alkyl$_{(C \leq 12)}$, substituted cycloalkyl$_{(C \leq 12)}$;
n is an integer from 1 to 500;

R$_2$ and R$_2$' are each independently selected from hydrogen, alkyl$_{(C\leq12)}$, cycloalkyl$_{(C\leq12)}$, substituted alkyl$_{(C\leq12)}$, or substituted cycloalkyl$_{(C\leq12)}$;

R$_3$ is a group of the formula:

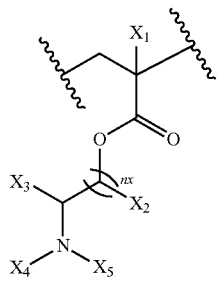

(II)

wherein:
n$_x$ is 1-10;
X$_1$, X$_2$, and X$_3$ are each independently selected from hydrogen, alkyl$_{(C\leq12)}$, cycloalkyl$_{(C\leq12)}$, substituted alkyl$_{(C\leq12)}$, or substituted cycloalkyl$_{(C\leq12)}$; and
X$_4$ and X$_5$ are each independently selected from alkyl$_{(C\leq12)}$, cycloalkyl$_{(C\leq12)}$, or a substituted version of any of these groups, or X$_4$ and X$_5$ are taken together and are alkanediyl$_{(C\leq12)}$, alkoxydiyl$_{(C\leq12)}$, alkylaminodiyl$_{(C\leq12)}$, or a substituted version of any of these groups;

x is an integer from 1 to 150;
R$_4$ is a group of the formula:

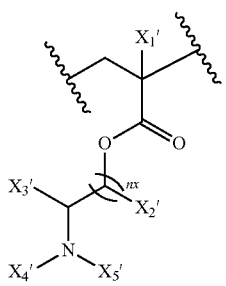

(III)

wherein:
n$_y$ is 1-10;
X$_1$', X$_2$', and X$_3$' are each independently selected from hydrogen, alkyl$_{(C\leq12)}$, cycloalkyl$_{(C\leq12)}$, substituted alkyl$_{(C\leq12)}$, or substituted cycloalkyl$_{(C\leq12)}$; and
X$_4$' and X$_5$' are each independently selected from hydrogen, alkyl$_{(C\leq12)}$, cycloalkyl$_{(C\leq12)}$, acyl$_{(C\leq12)}$, substituted alkyl$_{(C\leq12)}$, substituted cycloalkyl$_{(C\leq12)}$, substituted acyl$_{(C\leq12)}$, a dye, or a fluorescence quencher or X$_4$' and X$_5$' are taken together and are alkanediyl$_{(C\leq12)}$, alkoxydiyl$_{(C\leq12)}$, alkylaminodiyl$_{(C\leq12)}$, or a substituted version of any of these groups;
y is an integer from 0 to 150;
R$_5$ is hydrogen, halo, hydroxy, alkyl$_{(C\leq12)}$, or substituted alkyl$_{(C\leq12)}$, wherein R$_3$ and R$_4$ can occur in any order within the polymer, provided that R$_3$ and R$_4$ are not the same group. In some embodiments, the diblock copolymer is further defined as:

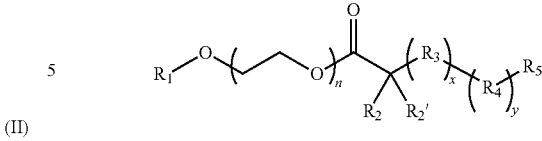

(IV)

wherein:
R$_1$ is hydrogen, alkyl$_{(C\leq12)}$, cycloalkyl$_{(C\leq12)}$, substituted alkyl$_{(C\leq12)}$, substituted cycloalkyl$_{(C\leq12)}$;
n is an integer from 1 to 500;
R$_2$ and R$_2$' are each independently selected from hydrogen, alkyl$_{(C\leq12)}$, cycloalkyl$_{(C\leq12)}$, substituted alkyl$_{(C\leq12)}$, or substituted cycloalkyl$_{(C\leq12)}$;
R$_3$ is a group of the formula:

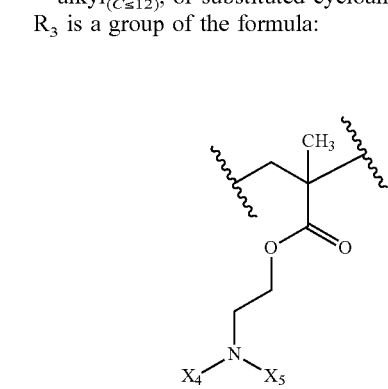

(V)

wherein:
X$_4$ and X$_5$ are each independently selected from alkyl$_{(C\leq12)}$, cycloalkyl$_{(C\leq12)}$, or a substituted version of either of these groups, or X$_4$ and X$_5$ are taken together and are alkanediyl$_{(C\leq12)}$, alkoxydiyl$_{(C\leq12)}$, alkylaminodiyl$_{(C\leq12)}$, or a substituted version of any of these groups;
x is an integer from 1 to 150;
R$_4$ is a group of the formula:

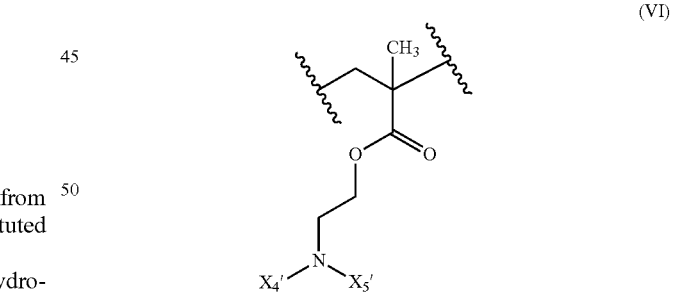

(VI)

wherein:
X$_4$' and X$_5$' are each independently selected from hydrogen, alkyl$_{(C\leq12)}$, cycloalkyl$_{(C\leq12)}$, acyl$_{(C\leq12)}$, substituted alkyl$_{(C\leq12)}$, substituted cycloalkyl$_{(C\leq12)}$, substituted acyl$_{(C\leq12)}$, a dye, or a fluorescence quencher or X$_4$' and X$_5$' are taken together and are alkanediyl$_{(C\leq12)}$, alkoxydiyl$_{(C\leq12)}$, alkylaminodiyl$_{(C\leq12)}$, or a substituted version of any of these groups;
y is an integer from 0 to 150;
R$_5$ is hydrogen, halo, hydroxy, alkyl$_{(C\leq12)}$, or substituted alkyl$_{(C\leq12)}$, wherein $R_3$ and $R_4$ can occur in any order within the polymer, provided that $R_3$ and $R_4$ are not the same group. In some embodiments, the diblock copolymer is further defined as:

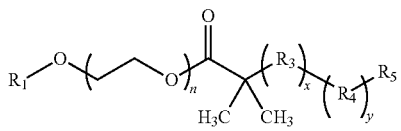

(IV)

wherein:
$R_1$ is hydrogen, alkyl$_{(C \le 12)}$, cycloalkyl$_{(C \le 12)}$, substituted alkyl$_{(C \le 12)}$, substituted cycloalkyl$_{(C \le 12)}$;
n is an integer from 1 to 500;
$R_3$ is a group of the formula:

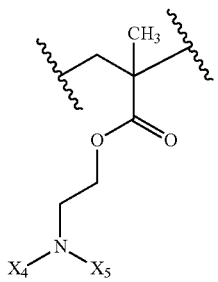

(V)

wherein:
$X_4$ and $X_5$ are each independently selected from alkyl$_{(C \le 12)}$, cycloalkyl$_{(C \le 12)}$, or a substituted version of either of these groups, or $X_4$ and $X_5$ are taken together and are alkanediyl$_{(C \le 12)}$, alkoxydiyl$_{(C \le 12)}$, alkylaminodiyl$_{(C \le 12)}$, or a substituted version of any of these groups;
x is an integer from 1 to 150;
$R_4$ is a group of the formula:

(VI)

wherein:
$X_4'$ and $X_5'$ are each independently selected from hydrogen, alkyl$_{(C \le 12)}$, cycloalkyl$_{(C \le 12)}$, acyl$_{(C \le 12)}$, substituted alkyl$_{(C \le 12)}$, substituted cycloalkyl$_{(C \le 12)}$, substituted acyl$_{(C \le 12)}$, a dye, or a fluorescence quencher or $X_4'$ and $X_5'$ are taken together and are alkanediyl$_{(C \le 12)}$, alkoxydiyl$_{(C \le 12)}$, alkylaminodiyl$_{(C \le 12)}$, or a substituted version of any of these groups;
y is an integer from 0 to 15;

$R_5$ is hydrogen, halo, hydroxy, alkyl$_{(C \le 12)}$, or substituted alkyl$_{(C \le 12)}$,
provided that $R_3$ and $R_4$ are not the same group. In some embodiments, the diblock copolymer further defined as:

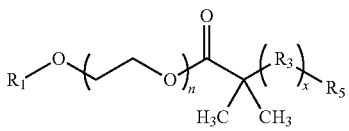

(V)

wherein:
$R_1$ is hydrogen, alkyl$_{(C \le 12)}$, cycloalkyl$_{(C \le 12)}$, substituted alkyl$_{(C \le 12)}$, substituted cycloalkyl$_{(C \le 12)}$;
n is an integer from 1 to 500;
$R_3$ is a group of the formula:

(V)

wherein:
$X_4$ and $X_5$ are each independently selected from alkyl$_{(C \le 12)}$, cycloalkyl$_{(C \le 12)}$, or a substituted version of either of these groups, or $X_4$ and $X_5$ are taken together and are alkanediyl$_{(C \le 12)}$, alkoxydiyl$_{(C \le 12)}$, alkylaminodiyl$_{(C \le 12)}$, or a substituted version of any of these groups;
x is an integer from 1 to 150;
$R_5$ is hydrogen, halo, hydroxy, alkyl$_{(C \le 12)}$, or substituted alkyl$_{(C \le 12)}$,
provided that $R_3$ and $R_4$ are not the same group.

In some embodiments, $R_1$ is alkyl$_{(C \le 12)}$ such as methyl. In some embodiments, n is 50 to 200. In some embodiments, n is 75 to 150. In some embodiments, n is 114.

In some embodiments, $X_4$ is alkyl$_{(C \le 12)}$ or cycloalkyl$_{(C \le 12)}$. In some embodiments, $X_4$ is alkyl$_{(C \le 12)}$ such as ethyl, isopropyl, n-propyl, n-butyl, or n-pentyl. In some embodiments, $X_4$ is alkyl$_{(C1-3)}$. In some embodiments, $X_5$ is alkyl$_{(C \le 12)}$ or cycloalkyl$_{(C \le 12)}$. In some embodiments, $X_5$ is alkyl$_{(C \le 12)}$ such as ethyl, isopropyl, n-propyl, n-butyl, or n-pentyl. In some embodiments, $X_4$ is alkyl$_{(C1-3)}$. In some embodiments, $X_4$ and $X_5$ are taken together and are alkanediyl$_{(C \le 12)}$, alkoxydiyl$_{(C \le 12)}$, alkylaminodiyl$_{(C \le 12)}$, or a substituted version of any of these groups. In some embodiments, $X_4$ and $X_5$ are taken together and are alkanediyl$_{(C \le 12)}$ or substituted alkanediyl$_{(C \le 12)}$. In some embodiments, $X_4$ and $X_5$ are taken together and are
—CH$_2$CH$_2$CH$_2$CH$_2$CH$_2$—,
—CH$_2$CH$_2$CH$_2$CH$_2$CH$_2$CH$_2$—,
—CH$_2$CH$_2$CH$_2$CH$_2$CH$_2$CH$_2$CH$_2$—, —CH$_2$CH$_2$CH(CH$_3$)CH$_2$CH$_2$—, or —CH$_2$CH(CH$_3$)CH$_2$CH(CH$_3$)CH$_2$—.

In some embodiments, x is 50 to 120. In some embodiments, x is 60 to 100. In some embodiments, y is 0. In other embodiments, y is 1, 2, 3, 4, or 5. In some embodiments, $X_4'$ is a dye such as a fluorescent dye or a fluorescence quencher. In some embodiments, $X_4'$ is alkyl$_{(C≤12)}$. In some embodiments, $X_4'$ and $X_5'$ are taken together and are alkanediyl$_{(C≤12)}$. In some embodiments, $X_5'$ is hydrogen. In some embodiments, $X_5'$ is alkyl$_{(C≤12)}$. In some embodiments, the diblock copolymer is PEG$_{114}$-b-PDEA$_{70}$, PEG$_{114}$-b-PEPA$_{70}$, PEG$_{114}$-b-PDPA$_{70}$, PEG$_{114}$-b-PDBA$_{70}$, PEG$_{114}$-b-PD5A$_{70}$, PEG$_{114}$-b-PC6A$_{70}$, PEG$_{114}$-b-PC7A$_{70}$, PEG$_{114}$-b-PC8A$_{70}$, PEG$_{114}$-b-PC6S1A$_{70}$, or PEG$_{114}$-b-PC6S2A$_{70}$. In some embodiments, the diblock copolymer is PEG$_{114}$-b-PEPA$_{70}$, PEG$_{114}$-b-PC6A$_{70}$, PEG$_{114}$-b-PC7A$_{70}$, PEG$_{114}$-b-PC6S1A$_{70}$, or PEG$_{114}$-b-PC6S2A$_{70}$.

In some embodiments, the compositions further comprise a solvent. In some embodiments, the solvent is water. In some embodiments, the solvent is an aqueous buffer such as phosphate buffered saline (PBS). In some embodiments, the compositions activate the STING pathway. In some embodiments, the compositions activate the interferon receptor pathway.

In another aspect, the present disclosure provides compositions comprising an adjuvant and an antigen which activates the STING pathway and the adjuvant forms a nanoparticle.

In still yet another aspect, the present disclosure provides compositions comprising an adjuvant and an antigen which activates one or more interferon receptor proteins and the adjuvant forms a nanoparticle.

In yet another aspect, the present disclosure provides compositions comprising:
 (A) an adjuvant; and
 (B) an antigen;
wherein the composition is a nanoparticle comprising a particle size of less than 50 nm, a plurality of heterocycloalkyl groups on the adjuvant, wherein at least one of the heteroatoms in the heterocycloalkyl group is a nitrogen atom, and a pH transition point from about 6.5 to 7.4. In some embodiments, the particle size is from 5 nm to 50 nm. In some embodiments, the plurality of heterocycloalkyl group is from 10 to 200 heterocycloalkyl groups. In some embodiments, the plurality of heterocycloalkyl group is from 40 to 160 heterocycloalkyl groups. In some embodiments, the heterocycloalkyl group is azepane. In some embodiments, the pH transition point is from 6.5 to 7.2. In some embodiments, the pH transition point is from 6.8 to 7.0.

In still yet another aspect, the present disclosure provides pharmaceutical compositions comprising:
 (A) a composition described herein; and
 (B) an excipient.
In some embodiments, the pharmaceutical compositions are formulated for injection. In some embodiments, the pharmaceutical compositions are formulated for intravenous, intramuscular, intraperitoneal, or subcutaneous injection. In some embodiments, the pharmaceutical compositions are formulated as a unit dose.

In some embodiments, the pharmaceutical compositions further comprise a second active agent. In some embodiments, the second active agent is a checkpoint inhibitor. In some embodiments, the checkpoint inhibitor is a PD-1 inhibitor. In some embodiments, the PD-1 inhibitor is an anti-PD-1 antibody. the anti-PD-I antibody is nivolumab, pembrolizumab, BMS 936559, MPDL328OA, or pidilizumab.

In yet another aspect, the present disclosure provides methods of treating a disease or disorder in a patient in need thereof comprising administering to the patient a therapeutically effective amount of the compositions described herein.

In some embodiments, the disease or disorder is cancer. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is melanoma mesothelioma, or cervical cancer.

In some embodiments, the methods further comprise a second anti-cancer therapy. In some embodiments, the second anti-cancer therapy is surgery, chemotherapeutic, radiation therapy, gene therapy, or second immunotherapy. In some embodiments, the second anti-cancer therapy is a second immunotherapy. In some embodiments, the second immunotherapy is a checkpoint therapy. In some embodiments, the immunotherapy is an inhibitor of PD-1. In some embodiments, the immunotherapy is nivolumab, pembrolizumab, pidilizumab, BMS 936559, or MPDL328OA. In other embodiments, the second anti-cancer therapy is radiation therapy. In some embodiments, the radiation therapy is administered two or more times, the composition is administered two or more times, or both are administered two or more times.

In other embodiments, the disease or disorder is an infectious disease. In some embodiments, the disease or disorder is malaria. In some embodiments, the disease or disorder is a viral infection such as HIV, Hepatitis B, Ebola, dengue, or West Nile virus. In other embodiments, the disease or disorder is a bacterial infection such as tuberculosis. In other embodiments, the disease or disorder is an autoimmune disease.

In some embodiments, the patient is a mammal. In some embodiments, the patient is a human. In some embodiments, the methods comprise administering the composition once. In other embodiments, the methods comprise administering the composition two or more times.

In still yet another aspect, the present disclosure provides methods of activating the STING pathway in a patient comprising administering to the patient in need thereof a composition comprising an antigen and an adjuvant wherein the adjuvant forms a nanoparticle. In some embodiments, the adjuvant is a synthetic polymer.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-D. PC7A NP induces robust antigen-specific CTL and Th1 responses. (FIG. 1A) Schematic of CFSE method to screen for polymer structures that generate strong OVA-specific CTL response. OVA was used as a model antigen (10 µg) and loaded in different polymer NPs (30 µg). (FIG. 1B) Quantitative comparison of OVA-specific CTL responses in different NP groups (n=3 for each group) identified PC7A NP as the best candidate. OVA-specific productions of IgG1 (FIG. 1C) and IgG2c (FIG. 1D) as induced by different vaccine groups. PC7A NP produced broad CTL, Th1 and Th2 responses comparable to or better than the known adjuvants in each category. In FIGS. 1B-D, representative data from three independent experiments are presented as means±s.e.m.

FIGS. 2A-G. PC7A NP improves antigen delivery and cross-presentation in APCs and stimulates CD8 T cell responses. (FIG. 2A) Quantification of OVA-positive cells in three APC subtypes inside lymph nodes 24 h after subcutaneous injection of AF647-OVA-PC7A NP at the tail base of C57BL/6 mice (n=5). (FIG. 2B) Schematic of detection of antigen cross-presentation in BMDCs and CD8$^+$ T cell activation in vitro. (FIG. 2C) Quantification of AF647-OVA uptake in BMDCs by flow cytometry after incubation with AF647-OVA alone, AF647-OVA-PC7A NP or AF647-OVA-PD5A NP for 4 h. Mean fluorescence intensity (MFI) of AF647-OVA$^+$ cells in BMDCs was determined (n=3). (FIG. 2D) Levels of antigen presentation on H-2K$^b$ in BMDCs induced by PC7A or PD5A NP (n=3). (FIG. 2E) IFN-γ secretion by OT-I CD8$^+$ T cells after incubating OT-I CD8$^+$ T cells with BMDCs treated with different OVA-NPs (n=3). (FIG. 2F) Representative flow dot plots of H-2k$^b$/SIINFEKL tetratmer staining of CD8$^+$ T cells in spleen. (FIG. 2G) Percentage of OVA (SIINFEKL) specific CD8$^+$ T cells was measured by flow cytometry (n=4). In FIGS. 2A, 2C-E and 2G, representative data from three independent experiments are presented as means±s.e.m. Statistical significance was calculated by Student's t-test, *P<0.001, P<0.01, *P<0.05. NS, not significant.

FIGS. 3A-F. PC7A NP activates APCs in draining lymph nodes and stimulates STING-dependent adaptive immune responses. (FIG. 3A) Expression of co-stimulator CD86 on CD8α$^+$ and CD8α$^-$ DCs in inguinal lymph nodes 24 h after injection of nanovaccine (n=5 for each group). Data on macrophages and B cells are shown in FIG. 7D. (FIGS. 3B-C) Measurement of expression levels of interferon-stimulated genes (IRF7 and CXCL10) at injection site by qPCR (n=6). (FIG. 3D) Quantitative comparison of OVA-specific CTL responses in different knockout mouse groups (n=5 for each group). IgG1 (FIG. 3E) and IgG2c (FIG. 3F) antibody titers in the serum were determined by ELISA (n=5 for each group). Data are presented as means±s.e.m. Statistical significance was calculated by Student's t-test, *P<0.001, P<0.01, *P<0.05. NS, not significant.

FIGS. 4A-G. PC7A nanovaccine inhibits tumor growth and prolongs survival in tumor bearing mice. (FIG. 4A) Schematic of the minimalist design of PC7A nanovaccine. (FIGS. 4B-C) C57BL/6 mice (n=10 per group) inoculated with 1.5×10$^5$ B16-OVA tumor cells were treated with OVA peptide, PC7A nanovaccine, CpG, poly(I:C) and Alum plus peptide (0.5 µg). Tumor growth (FIG. 4B) and Kaplan-Meier survival curves (FIG. 4C) of tumor-bearing mice were shown. (FIG. 4D) Tumor growth inhibition study of B16F10 melanoma. C57BL/6 mice (n=10 per group) inoculated with 1.5×10$^5$ B16F10 tumor cells were treated with a cocktail of tumor associated antigens (Gp100$_{21-41}$, Trp1$_{214-237}$, Trp2$_{173-196}$) in PC7A NP at specific time point indicated by the arrows. (FIG. 4E) Tumor growth inhibition study of MC38 colon cancer in C57BL/6 mice. Mice (n=10 per group) inoculated with 1.0×10$^6$ MC38 tumor cells were treated with a cocktail of neoantigens (Reps1$_{P45A}$, Adpgk$_{R304M}$, Dpagt1$_{V213L}$) in PC7A NP, and nanovaccine was administered on day 10 and 15 in established tumors (100-200 mm$^3$). In the HPV tumor model, tumor growth inhibition (FIG. 4F) and survival data (FIG. 4G) in C57BL/6 mice (n=10 per group) were analyzed after tumor inoculation with 1.5×10$^5$ TC-1 tumor cells. In FIGS. 4B and 4D-F, data are presented as means±s.e.m. Statistical significance was calculated by Student's t-test, *P<0.001, P<0.01, *P<0.05. Statistical significance for survival analysis in FIGS. 4C and 4G was calculated by the log-rank test, *P<0.001, P<0.01, *P<0.05.

FIGS. 5A-C. Syntheses and pH titration of ultra-pH sensitive (UPS) PEG-b-PR block copolymers. (FIG. 5A) Schematic syntheses of block copolymers using an atom-transfer radical polymerization (ATRP) method. PEG-Br (MW=5 kD) was used as an initiator and metharylates with different tertiary amine side chains were used as monomers. (FIG. 5B) Characterization of the copolymers from the library. Number-averaged molecular weight (Mn) was determined by GPC using THF as the eluent; pKa was determined by pH titration of polymer solutions using 4 M NaOH. Size was measured using dynamic light scattering, mean±s.d. (FIG. 5C) pH titration of UPS copolymers displayed pH-specific buffer effect from pH 4 to 8. For the cyclic series, both the size of cyclic rings (i.e., 6, 7 and 8) and number of methyl substitutions (e.g., 0, 1 and 2) on the 6-membered ring were investigated. Copolymers with similar hydrophobic strengths (e.g., PC7A vs. PC6S1A; PC8A vs. PC6S2A) share similar pKa values despite different polymer architectures and CTL response (see FIG. 1B).

FIGS. 6A-D. Efficient loading of OVA in PC7A NP through a physical mixing procedure. (FIG. 6A) The OVA loading efficiency in the micelle nanoparticles was measured by an ultrafiltration method. (FIG. 6B) Loading stability of OVA in PC7A micelles was examined in PBS buffer (pH 7.4) containing 5% fetal bovine serum at different time points. (FIG. 6C) Schematic synthesis of dye-conjugated PEG-b-PC7A copolymer. Cy3.5 was used as a dye example. (FIG. 6D) Fluorescence spectra of Cy3.5 labelled PC7A, AF647-OVA and PC7A+OVA mixture, which showed strong fluorescence resonance electron transfer (FRET) effect in the mixture group indicating OVA loading inside PC7A NP. (FIG. 6E) AF647-OVA (100 µg/mL) was incubated with serially diluted Cy3.5-conjugated PC7A in PBS buffer (pH=7.4), dotted line showed the working concentration of nanovaccine and its FRET efficiency. In FIGS. 6A-B, representative data from three independent experiments are presented as means±s.e.m.

FIGS. 7A-D. PC7A NP improves antigen delivery in draining lymph nodes, induces LN inflammation and APC maturation. (FIG. 7A) Near infrared imaging of ICG-labelled PC7A NP accumulation in lymphoid organs after subcutaneous injection at the tail base of C57BL/6 mice (n=3). After 24 h, lymph nodes and major organs were collected, and ex vivo imaging showed high PC7A NP accumulation in the lymph nodes over other organs. (FIG. 7B) Midline cross-section (maximal surface) of resected draining lymph nodes from C57BL/6 mice showed enlarged nodes by PC7A NP over OVA alone. (FIG. 7C) Quantification of total cell numbers in the draining lymph nodes at 24 h. Enlarged lymph nodes and increased cell number in the PC7A NP group indicate innate stimulation (n=5). (FIG. 7D) Quantitative comparison of CD86 expressions in $CD8\alpha^+$, $CD8\alpha^-$ DCs, macrophages and B cells in inguinal lymph nodes 24 h after injection of nanovaccine (n=5 for each group). In FIGS. 7C-D, representative data from three independent experiments are presented as means±s.e.m. Statistical significance was calculated by Student's t-test, *$P<0.001$, $P<0.01$, *$P<0.05$. NS, not significant.

FIGS. 8A-B. PC7A NP disrupts membranes at acidic pH. (FIG. 8A) Hemolytic analysis of the red blood cells after treatment with PC7A or PD5A copolymers in different pH medium. (FIG. 8B) Percentage of hemolysis was quantified by the release of hemoglobin into the medium as a function of pH for PC7A or PD5A NP (n=3). Both polymer concentrations were controlled at 20 μg/mL. In FIG. 8B, representative data from three independent experiments are presented as means±s.e.m.

FIG. 9A-J. PC7A NP activates type I IFN-induced genes through STING pathway. Mouse bone marrow derived macrophages (BMDMs, FIG. 9A), human THP-1 monocytic cells (FIG. 9B) were incubated with PC7A NP at indicated concentration and time, followed by measurement of CXCL10 mRNA by qPCR (n=3). cGAMP, a STING activator transfected by lipofectamine was used as a positive control. Results show STING-dependent expression of CXCL10 in both cell lines. (FIG. 9C) BMDMs were transfected with DNase I for 1 hr, and followed by treatment with PC7A NP. CXCL10 mRNA was measured by qPCR (n=3). (FIG. 9D) PC7A NP treated THP-1 cells resulted in pull-down of STING proteins by streptavidin modified dynabeads. PD5A-biotin and PC7A only (biotin free) controls did not show any STING pulldown. (FIG. 9E) Direct pulldown assay of purified human STING C-terminal domain (CTD, 139-379AAs). PC7A-biotin copolymer pulled down STING CTD, but not other copolymers or PC7A only control. (FIG. 9F) Titration of PC7A binding to STING CTD by isothermal calorimetry (ITC) experiments. The original titration traces (top) and integrated data (bottom) were shown. ITC of PC7A-bovine serum albumin (BSA) was used as a negative control and cGAMP-STING CTD as a positive control. (FIG. 9G) Summary of binding affinity in ITC experiment. Negligible binding was found between PC7A and BSA. (FIG. 9H) Measurement of IDO enzyme activity in spleen cells after subcutaneous injection of different copolymers (150 μg, n=5). PEI-DNA (30 μg) was used as a positive control. (FIG. 9I) Human THP-1 and (FIG. 9J) mouse BMDM cells were treated with different NPs, followed by measurement of IDO-1 and CXCL10 mRNAs by qPCR (n=3). PEI-DNA, Poly(I:C) and cGAMP were used as positive controls. In FIGS. 9A-C, and FIGS. 9I-J, representative data from three independent experiments are presented as means±s.e.m. In FIG. 9H, representative data from two independent experiments are presented as means±s.e.m. Statistical significance was calculated by Student's t-test, *$P<0.001$, $P<0.01$, *$P<0.05$. NS, not significant.

FIGS. 10A-D. APCs are the major cell population that take up PC7A NP and activate STING pathway in vivo. PC7A NP-Cy5 was injected subcutaneously at the tail base of C57BL/6 mice, and PBS injected mice were included as control (n=5). After 24 hrs, inguinal LNs and subcutaneous tissue were isolated, and made into single cell suspension. Cells were first gated on live cells and then divided as leukocytes (CD45+) and non-leukocytes (CD45−). By the fluorescence of PC7A NP, cells from NP treated mice were divided into NP+ and NP− populations. The pIRF3 expression and DC marker CD11c were assessed in these subsets. (FIG. 10A) Comparative assessment of CD45+NP+ and CD45+NP− cells in LNs. (FIG. 10B) Phenotypic analysis of NP+ and NP− cells in LNs by flow cytometry. (FIG. 10C) Assessment of NP accumulated cells (NP+) in both CD45+ and CD45− cells from subcutaneous tissue. (FIG. 10D) Phenotypic analysis of CD45+NP− and CD45+ NP+ cells in subcutaneous tissue by flow cytometry. In FIGS. 10A and 10C, representative data from two independent experiments are presented as means±s.e.m. Statistical significance was calculated by Student's t-test, ***$P<0.001$. NS, not significant.

FIGS. 11A-F. PC7A nanovaccine inhibits tumor growth and prolongs survival. C57BL/6 mice (n=10 per group) were first inoculated with $1.5\times10^5$ B16-OVA tumor cells and followed by treatment with OVA peptide (0.5 μg), OVAp-PD5A NP, PC7A alone or OVAp-PC7A NP. PC7A NP alone without OVAp had no observable effect in tumor growth inhibition (FIG. 11A) or animal survival curves (FIG. 11B). (FIG. 11C) Tumor growth inhibition of B16F10 treated by neoantigen-PC7A NP. C57BL/6 mice (n=10 per group) inoculated with $1.5\times10^5$ B16F10 tumor cells were treated with a cocktail of neoantigens (Obsl1$_{T1764M}$, Kif18b$_{K739N}$, Def8$_{R255G}$) in PC7A NP (0.5 μg for each peptide, 30 μg polymer) per time points indicated by the arrows. (FIG. 11D) C57BL/6 mice (n=3 per group) were immunized with E7 peptide (E7p, 0.5 μg) and E7p-PC7A NP. E7-specific cytotoxicity was measured using an in vivo cytotoxicity killing assay. (FIG. 11E) Naïve mice or tumor-free mice 82 days after tumor inoculation in TC-1 model (n=10 per group) were challenged with $1\times10^6$ TC-1 tumor cells. On day 30 after surgery, mice were rechallenged with $1\times10^6$ TC-1 tumor cell. Memory T cells in the nanovaccine cured group completely inhibited tumor growth over 60 days. (FIG. 11F) Tumor growth inhibition curves in C57BL/6 mice (n=10 per group) inoculated with $1.5\times10^5$ TC-1 tumor cells and treated with nanovaccine at day 10 and 15 when tumors were established at ~100 mm³. In FIGS. 11A and 11C-F, data are presented as means±s.e.m. Statistical significance was calculated by Student's t-test, *$P<0.001$, $P<0.01$, *$P<0.05$. NS, not significant. Statistical significance for survival analysis in FIG. 11B was calculated by the log-rank test, ***$P<0.001$. NS, not significant.

FIGS. 12A-F. Synergy effect of nanovaccine and anti-PD-1 antibody in two tumor models. (FIG. 12A) C57BL/6 mice inoculated with $1.5\times10^5$ B16-OVA tumor cells were treated with OVA peptide, PC7A nanovaccine, anti-PD-1 alone and anti-PD-1 in combination with PC7A nanovaccine. Kaplan-Meier survival curves of tumor-bearing mice were shown. (FIG. 12B) Long-term tumor growth inhibition curves in C57BL/6 mice (n=10 per group) inoculated with $1.5\times10^5$ TC-1 tumor cells followed by treatment with E7p (0.5 μg), PC7A nanovaccine, and a combination of anti-PD-1 and nanovaccine. (FIG. 12C) Individual tumor growth curves for OVAp alone, OVAp-PC7A NP, and OVAp-PC7A NP combined with anti-PD-1. (FIG. 12B) The PD-L1 expression profile in B16-OVA tumors. The PD-L1 were highly expressed in MDSCs (CD11b+Gr1+) and macrophages (CD11b+F4/80+) over the isotype control whereas the expression in DCs (CD11c+) and B16-OVA melanoma cells (CD45−) are modest. (FIG. 12E) Individual tumor growth curves for E7p alone, E7p-PC7A NP, and E7p-PC7A NP combined with anti-PD-1. Data show 50% and 90% of mice had tumor-free survival in the E7p-PC7A NP and E7p-PC7A NP/anti-PD-1 groups, respectively. (FIG. 12F) The PD-L1 expression profile in TC-1 tumors. The PD-L1 expressions were highly expressed in DCs, MDSCs, and macrophages over the isotype control whereas the expression in TC-1 tumor cells is modest. In FIG. 12B, data are presented as means±s.e.m. Statistical significance was calculated by Student's t-test, **P<0.01. Statistical significance for survival analysis in FIG. 12A was calculated by the log-rank test, *P<0.05.

FIGS. 16A-16C. Evaluation of physical loading versus covalent conjugation of peptide antigens on CTL response. (FIG. 16A) Two synthetic routes of peptide conjugation to the surface or core of the PEG-b-PC7A micelle nanoparticles for antigen loading. (FIG. 16B) Schematic illustration of the nanovaccines as produced from three different strategies. (FIG. 16C) Quantitative comparison of OVA-specific CTL response across different nanovaccine groups (n=3 per group). OVAp-poly(I:C) was used as a control. Data represent mean±s.e.m., *P<0.001, P<0.01, *P<0.05, NS, not significant.

FIGS. 17A-E. Mice vaccinated with the influenza virus H1N1 HA antigen and PC7A nanoparticle produced anti-HA antibodies and are protected from lethal infections by the H1N1 influenza virus. For FIGS. 17A-C, circulating anti-H1N1 HA total IgG (FIG. 17A) levels were measured by ELISA in serum harvested from vaccinated mice one week post-boost. Circulating anti-H1N1 HA IgG1 (FIG. 17B) and IgG2b (FIG. 17C) levels in vaccinated mouse sera were also measured. B6 WT mice (n=5/group) were primed i.m. with H1N1 PR8 HA alone or in combination with either Alum or PC7A. A booster dose was administered ten days post-prime. For FIGS. 17D-E, mice were vaccinated intranasally challenged with 10× $MLD_{50}$ (median lethal dose for 50% mortality) of influenza A/PR/8/34 (H1N1) virus 1.5 weeks post-boost. Bodyweight (FIG. 17D) and survival (FIG. 17E) were tracked daily for two weeks.

FIG. 18. Nanovaccine combined with radiation therapy (RT) can induce regression of established HPV tumors. $2 \times 10^5$ TC-1 cells were injected subcutaneously on the back of C57BL/6 mice (n=8/group). Tumors were radiated at 20 Gy 14 days later when they reached the size of ~200 mm³. For vaccination treatments, on the same day of ionizing radiation, the nanovaccine (30 μg PC7A+0.5 μg peptide $E7_{43-62}$ (GQAEPDRAHYNIVTFCCKCD, SEQ ID NO: 26)) was injected subcutaneously onto the back of mice at the tail base. Six days later, the mice were boosted with another injection of nanovaccine with the same dose. Tumor growth was subsequently measured twice a week using a digital caliper and calculated as 0.5×length×width² by blinded investigators. Mice were sacrificed when tumor size reached 1500 mm³. The combined nanovaccine and radiation therapy showed significantly improved therapeutic synergy over radiation or nanovaccine alone treatment.

DETAILED DESCRIPTION

Figure 1A:
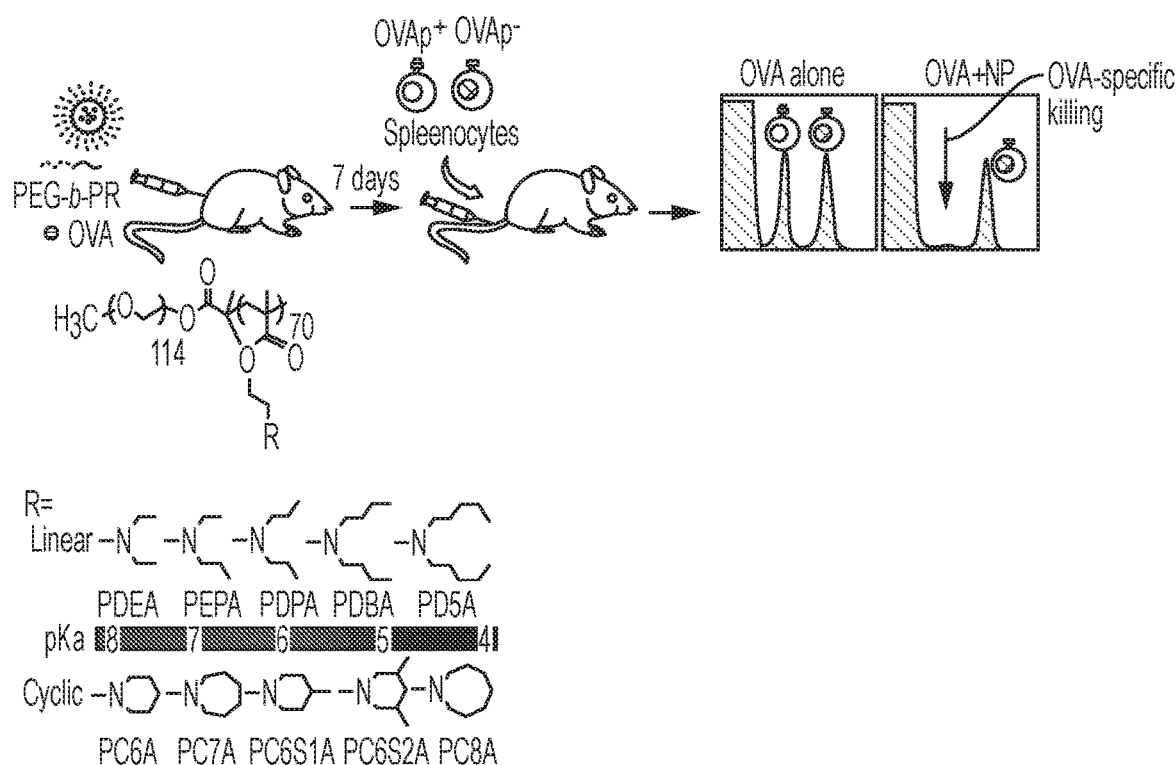

In some aspects, the present disclosure provides vaccine compositions which may be used to generate an immune response to a disease antigen such as cancer or an infectious disease. These vaccine compositions may activate the STING and/or the interferon receptor pathways in vivo leading to an enhanced immunoresponse. In some embodiments, the vaccine compositions comprise an antigen and a pH sensitive diblock copolymer. These compositions may be used in the treatment of various diseases and disorders such as cancer or an infectious disease.

I. Vaccine Components

The compositions described herein may comprise one or more immunostimulatory agents. Immunostimulatory agents include but are not limited to an antigen or antigenic compound, an immunomodulator, an APC, an adjuvant or a carrier. Other immunopotentiating compounds are also contemplated for use with the compositions of the present disclosure such as polysaccharides, including chitosan, which is described in U.S. Pat. No. 5,980,912, which is incorporated herein by reference. Multiple (more than one) antigens may be crosslinked to one another (e.g., polymerized). The use of small peptides for antibody generation or vaccination also may require conjugation of the peptide to an immunogenic carrier protein.

One of ordinary skill would know various assays to determine whether an immune response against a tumor-associated peptide was generated. The phrase "immune response" includes both cellular and humoral immune responses. Various B lymphocyte assays are well known, such as ELISAs, proliferation assays using peripheral blood lymphocytes (PBL), cytokine production and antibody production assays. See Benjamini et al. (1991), which is incorporated herein by reference.

A. Antigens

In some aspects, the present disclosure provides compositions one or more antigenic components. An antigen is a substance which promotes an immune response such that antibodies are generated against the substance specifically. Some substances are more immunogenic and thus the immune system will readily develop an appropriate immune response but other substances require assistance to generate an immune response sufficient to generate antibodies against the antigen. Most cancers may require additional activation to enhance the generation of antibodies against the antigen. Some non-limiting examples of antigens include proteins or fragments thereof of cancer specific surface proteins or surface proteins overexpressed by cancer cells. Additionally, the antigen may be one of the peptides or proteins included in Table 1:

bacteria into the blood, or a decrease in immune function. For example, *Staphylococcus* or *Streptococcus* are also part of the normal human flora and usually exist on the skin or in the nose without causing disease, but can potentially cause skin infections, pneumonia, meningitis, and even overwhelming sepsis, a systemic inflammatory response producing shock, massive vasodilation and death. Some species of bacteria, such as *Pseudomonas aeruginosa, Burkholderia cenocepacia*, and *Mycobacterium avium*, are opportunistic pathogens and cause disease mainly in people suffering from immunosuppression or cystic fibrosis.

TABLE 1

Sequence of Some Non-Limiting Examples of Protein and Peptide Antigens

| Antigen type | Source | Protein or Peptide Sequence | Cancer type |
|---|---|---|---|
| Tumor associated antigen | E7 (4-26) | DTPTLHEYMLDLQPETVDLYCYE (SEQ ID NO: 2) | HPV-induced cervical cancer, head and neck cancer, anogenital cancers |
| | E7 comb | LHEYMLDLQPETVDLDLLMGTLGIVCPICSQ (SEQ ID NO: 1) | |
| | Meso(406-432) | GQKMNAQAIALVACYLRGGGQLDEDMV (SEQ ID NO: 3) | Pancreatic cancer |
| | Gp100(201-224) | HASSTFTITDQVPFSVSVSQLQAL (SEQ ID NO: 4) | Melanoma |
| | Trp1(214-237) | SHEGPAFLTWHRYHLLQLERDMQE (SEQ ID NO: 5) | Melanoma |
| | Trp2(173-196) | QPQIANCSVYDFFVWLHYYSVRDT (SEQ ID NO: 6) | Melanoma |
| Tumor neoantigen | Obsl1T1764M | REGVELCPGNKYEMRRHGTTHSLVIHD (SEQ ID NO: 7) | Melanoma |
| | Pbk$_{V145D}$ | DSGSPFPAAVILRDALHMARGLKYLHQ (SEQ ID NO: 8) | Melanoma |
| | Tnpo3$_{G504A}$ | VVDRNPQFLDPVLAYLMKGLCEKPLAS (SEQ ID NO: 9) | Melanoma |
| | Kif18b$_{K739N}$ | PSKPSFQEFVDWENVSPELNSTDQPFL (SEQ ID NO: 10) | Melanoma |
| | Actn4 $_{F835V}$ | NHSGLVTFQAFIDVMSRETTDTDTADQ (SEQ ID NO: 11) | Melanoma |

Additionally, antigens for specific indications including several different infectious diseases, toxins, and cancers are contemplated herein.

i. Bacterial Pathogens

There are hundreds of bacterial pathogens in both the Gram-positive and Gram-negative families that cause significant illness and mortality around the word, despite decades of effort developing antibiotic agents. Indeed, antibiotic resistance is a growing problem in bacterial disease.

One of the bacterial diseases with highest disease burden is tuberculosis, caused by the bacterium *Mycobacterium tuberculosis*, which kills about 2 million people a year, mostly in sub-Saharan Africa. Some non-limiting examples of *Mycobacterium tuberculosis* antigens include recombinant Ag85A, Ag85B, ESAT6, TB10.4, or fragments thereof including those taught by Ottenhoff and Kaufmann, 2012, which is incorporated herein by reference. Pathogenic bacteria contribute to other globally important diseases, such as pneumonia, which can be caused by bacteria such as *Streptococcus* and *Pseudomonas*, and foodborne illnesses, which can be caused by bacteria such as *Shigella, Campylobacter*, and *Salmonella*. Pathogenic bacteria also cause infections such as tetanus, typhoid fever, diphtheria, syphilis, and leprosy.

Conditionally pathogenic bacteria are only pathogenic under certain conditions, such as a wound facilitates entry of Other bacterial invariably cause disease in humans, such as obligate intracellular parasites (e.g., *Chlamydophila, Ehrlichia, Rickettsia*) that are capable of growing and reproducing only within the cells of other organisms. Still, infections with intracellular bacteria may be asymptomatic, such as during the incubation period. An example of intracellular bacteria is *Rickettsia*. One species of *Rickettsia* causes typhus, while another causes Rocky Mountain spotted fever. Chlamydia, another phylum of obligate intracellular parasites, contains species that can cause pneumonia or urinary tract infection and may be involved in coronary heart disease. *Mycobacterium, Brucella, Francisella, Legionella*, and *Listeria* can exist intracellularly, though they are facultative (not obligate) intracellular parasites. Antigens for these bacteria may be used in the present compositions.

ii. Viral Pathogens

Vaccines may be developed for any viral pathogen for which protective antibodies are available. These include respiratory viruses such as Adenoviruses, Avian influenza, Influenza virus type A, Influenza virus type B, Measles, Parainfluenza virus, Respiratory syncytial virus (RSV), Rhinoviruses, and SARS-CoV, gastro-enteric viruses such as Coxsackie viruses, enteroviruses such as Poliovirus and Rotavirus, hepatitis viruses such as Hepatitis B virus, Hepatitis C virus, Bovine viral diarrhea virus (surrogate), herpes-viruses such as Herpes simplex 1, Herpes simplex 2, Human cytomegalovirus, and Varicella zoster virus, retroviruses such as Human immunodeficiency virus 1 (HIV-1), and Human immunodeficiency virus 2 (HIV-2), as well as Dengue virus, Hantavirus, Hemorrhagic fever viruses, Lymphocytic choromeningitis virus, Smallpox virus, Ebola virus, Rabies virus, West Nile virus and Yellow fever virus. Some non-limiting viral antigens include hepatitis B virus HBV surface and core antigens, influenza virus haemagglutinin and neuroaminidase antigens, West Nile virus envelop protein (E) and premembrane protein (prM), Dengue virus 80E subunit protein, Ebola virus glycoprotein, HIV envelope protein gp41 and gp120, or fragments thereof. Other HIV antigens can be found in de Taeye, et al., 2016, which is incorporated herein by reference. An antigen for any of these viral pathogens may be used in the present compositions.

iii. Fungal Pathogens

Pathogenic fungi are fungi that cause disease in humans or other organisms. The following are but a few examples.

*Candida* species are important human pathogens that are best known for causing opportunist infections in immunocompromised hosts (e.g., transplant patients, AIDS sufferers, and cancer patients). Infections are difficult to treat and can be very serious. *Aspergillus* can and does cause disease in three major ways: through the production of mycotoxins; through induction of allergic responses; and through localized or systemic infections. With the latter two categories, the immune status of the host is pivotal. The most common pathogenic species are *Aspergillus fumigatus* and *Aspergillus flavus*. *Cryptococcus neoformans* can cause a severe form of meningitis and meningo-encephalitis in patients with HIV infection and AIDS. The majority of *Cryptococcus* species lives in the soil and do not cause disease in humans. *Cryptococcus laurentii* and *Cryptococcus albidus* have been known to occasionally cause moderate-to-severe disease in human patients with compromised immunity. *Cryptococcus gattii* is endemic to tropical parts of the continent of Africa and Australia and can cause disease in non-immunocompromised people. *Histoplasma capsulatum* can cause histoplasmosis in humans, dogs and cats. *Pneumocystis jirovecii* (or *Pneumocystis carinii*) can cause a form of pneumonia in people with weakened immune systems, such as premature children, the elderly, transplant patients and AIDS patients. *Stachybotrys chartarum* or "black mold" can cause respiratory damage and severe headaches. It frequently occurs in houses in regions that are chronically damp. Antigens from these fungi may be included in the compositions described herein.

iv. Parasites

Parasite presents a major health issue, particularly in under-developed countries around the world. Significant pathogenic parasites include *Entamoeba histolytica, Giardia lamblia, Trichomonas vaginalis, Plasmodium falciparum, Plasmodium malariae, Plasmodium ovale, Plasmodium vivax, Trypanosoma gambiense, Trypanosoma rhodesiense, Trypanosoma cruzi, Ascaris lumbricoides, Trichinella spiralis, Toxoplasma gondii, Leishmania donovani, Leishmania tropica, Leishmania braziliensis, Schistosoma mansoni, Schistosoma japonicum, Schistosoma haematobium*, and *Pneumocystis jiroveci*. Antigens from malaria parasites may include but are not limited to circumsporozoite protein (CSP), sporozoite and liver-stage antigen (SALSA), merozoite surface protein (MSP) of *Plasmodium falciparum*, or fragments thereof as well as those described in Carvalho, et al., 2002, which is incorporated herein by reference. Antigens from these parasites may be included in the compositions described herein.

v. Toxins

Toxins constitute a significant threat to the population in both developed and under-developed countries. Biotoxins are biological in nature, i.e., they are produced by many living organisms, including bacteria, insects, snakes and plants. These include a wide variety of insect toxins, such as spider, scorpion, bee wasp, or ants, snake toxins, many of which are neurotoxins to hemotoxins, cyanotoxins, jellyfish toxins, ricin, botulism toxin, tetanus toxoid and mycotoxins.

Environmental toxins, on the other hand, are toxins that are non-biological in origin, and can be natural or manmade. These include industrial and agricultural chemicals such as phthalates, polychlorinated biphenyls (PCBs), pesticides, dioxin, asbestos, chlorine, chloroform, volatile organic compounds (VOCs), and heavy metals such as lead, cadmium and arsenic. Any of these toxins may be used in the present compositions to promote an immune response.

vi. Cancer

A variety of different peptides, protein fragments, or proteins may be used as antigens in the present compositions. Some non-limiting examples include 5T4, 707-AP (707 alanine proline), 9D7, AFP (α-fetoprotein), AlbZIP HPG1, α5β1-Integrin, α5β6-Integrin, α-methylacyl-coenzyme A racemase, ART-4 (adenocarcinoma antigen recognized by T cells 4), B7H4, BAGE-1 (B antigen), BCL-2, BING-4, CA 15-3/CA 27-29, CA 19-9, CA 72-4, CA125, calreticulin, CAMEL (CTL-recognized antigen on melanoma), CASP-8 (caspase-8), cathepsin B, cathepsin L, CD 19, CD20, CD22, CD25, CD30, CD33, CD40, CD52, CD55, CD56, CD80, CEA (carcinoembryonic antigen), CLCA2 (calcium-activated chloride channel-2), CML28, Coactosin-like protein, Collagen XXIII, COX-2, CT-9/BRD6 (bromodomain testis-specific protein), Cten (C-terminal tensin-like protein), cyclin B1, cyclin D1, cyp-B (cyclophilin B), CYPB1 (cytochrom P450 1B1), DAM-10/MAGE-B1 (differentiation antigen melanoma 10), DAM-6/MAGE-B2 (differentiation antigen melanoma 6), EGFR/Her1, EMMPRIN (tumour cell-associated extracellular matrix metalloproteinase inducer), EpCam (epithelial cell adhesion molecule), EphA2 (ephrin type-A receptor 2), EphA3 (ephrin type-A receptor 3), ErbB3, EZH2 (enhancer of Zeste homolog 2), FGF-5 (fibroblast growth factor-5), FN (fibronectin), Fra-1 (Fos-related antigen-1), G250/CAIX (glycoprotein 250), GAGE-1 (G antigen 1), GAGE-2 (G antigen 2), GAGE-3 (G antigen 3), GAGE-4 (G antigen 4), GAGE-5 (G antigen 5), GAGE-6 (G antigen 6), GAGE-7b (G antigen 7b), GAGE-8 (G antigen 8), GDEP (gene differentially expressed in prostate), GnT-V (N-acetylglucosaminyltransferase V), gp100 (glycoprotein 100 kDa), GPC3 (glypican 3), HAGE (helicase antigen), HAST-2 (human signet ring tumour-2), hepsin, Her2/neu/ErbB2 (human epidermal receptor-2/neurological), HERV-K-MEL, HNE (human neutrophil elastase), homeobox NKX 3.1, HOM-TES-14/SCP-1, HOM-TES-85, HPV-E6, HPV-E7, HST-2, hTERT (human telomerase reverse transcriptase), iCE (intestinal carboxyl esterase), IGF-1R, IL-13Ra2 (interleukin 13 receptor α 2 chain), IL-2R, IL-5, immature laminin receptor, kallikrein 2, kallikrein 4, Ki67, KIAA0205, KK-LC-1 (Kita-kyushu lung cancer antigen 1), KM-HN-1, LAGE-1 (L antigen), livin, MAGE-A1 (melanoma antigen-A1), MAGE-A10 (melanoma antigen-A10), MAGE-A12 (melanoma antigen-A12), MAGE-A2 (melanoma antigen-A2), MAGE-A3 (melanoma antigen-A3), MAGE-A4 (melanoma antigen-A4), MAGE-A6 (melanoma antigen-A6), MAGE-A9 (melanoma-antigen-A9), MAGE-B1 (melanoma-antigen-B 1), MAGE-B 10 (melanoma-antigen-B 10), MAGE-B16 (melanoma-antigen-B16), MAGE-B17 (melanoma-antigen-B17), MAGE- B2 (melanoma-antigen-B2), MAGE-B3 (melanoma-antigen-B3), MAGE-B4 (melanoma-antigen-B4), MAGE-B5 (melanoma-antigen-B5), MAGE-B6 (melanoma-antigen-B6), MAGE-C1 (melanoma-antigen-C1), MAGE-C2 (melanoma-antigen-C2), MAGE-C3 (melanoma-antigen-C3), MAGE-D 1 (melanoma-antigen-D1), MAGE-D2 (melanoma-antigen-D2), MAGE-D4 (melanoma-antigen-D4), MAGE-E1 (melanoma-antigen-E1), MAGE-E2 (melanoma-antigen-E2), MAGE-F1 (melanoma-antigen-F1), MAGE-H1 (melanoma-antigen-H1), MAGEL2 (MAGE-like 2), mammaglobin A, MART-1/Melan-A (melanoma antigen recognized by T cells-1/melanoma antigen A), MART-2 (melanoma antigen recognized by T cells-2), matrix protein 22, MC1R (melanocortin 1 receptor), M-CSF (macrophage colony-stimulating factor gene), mesothelin, MG50/PXDN, MMP 11 (M-phase phosphoprotein 11), MN/CA IX-antigen, MRP-3 (multidrug resistance-associated protein 3), MUC1 (mucin 1), MUC2 (mucin 2), NA88-A (NA cDNA clone of patient M88), N-acetylglucosaminyltransferase-V, Neo-PAP (Neo-poly(A) polymerase), NGEP, NMP22, NPM/ALK (nucleophosmin/anaplastic lymphoma kinase fusion protein), NSE (neuronspecific enolase), NY-ESO-1 (New York esophageous 1), NY-ESO-B, OA1 (ocular albinism type 1 protein), OFA-iLRP (oncofetal antigen-immature laminin receptor), OGT (O-linked N-acetylglucosamine transferase gene), OS-9, osteocalcin, osteopontin, p15 (protein 15), p15, p190 minor bcr-abl, p53, PAGE-4 (prostate GAGE-like protein-4), PAI-1 (plasminogen activator inhibitor 1), PAI-2 (plasminogen activator inhibitor 2), PAP (prostate acic phosphatase), PART-1, PATE, PDEF, Pim-1-Kinase, Pin1 (Propyl isomerase), POTE, PRAME (preferentially expressed antigen of melanoma), prostein, proteinase-3, PSA (prostate-specific antigen), PSCA, PSGR, PSM, PSMA (prostate-specific membrane antigen), RAGE-1 (renal antigen), RHAMM/CD168 (receptor for hyaluronic acid mediated motility), RU1 (renal ubiquitous 1), RU2 (renal ubiquitous 1), S-100, SAGE (sarcoma antigen), SART-1 (squamous antigen rejecting tumour 1), SART-2 (squamous antigen rejecting tumour 1), SART-3 (squamous antigen rejecting tumour 1), SCC (squamous cell carcinoma antigen), Sp17 (sperm protein 17), SSX-1 (synovial sarcoma X breakpoint 1), SSX-2/HOM-MEL-40 (synovial sarcoma X breakpoint), SSX-4 (synovial sarcoma X breakpoint 4), STAMP-1, STEAP (six transmembrane epithelial antigen prostate), surviving, survivin-2B (intron 2-retaining survivin), TA-90, TAG-72, TARP, TGFb (TGFbeta), TGFbRII (TGFbeta receptor II), TGM-4 (prostate-specific transglutaminase), TRAG-3 (taxol resistant associated protein 3), TRG (testin-related gene), TRP-1 (tyrosine related protein 1), TRP-2/6b (TRP-2/novel exon 6b), TRP-2/INT2 (TRP-2/intron 2), Trp-p8, Tyrosinase, UPA (urokinase-type plasminogen activator), VEGF (vascular endothelial growth factor), VEGFR-2/FLK-1 (vascular endothelial growth factor receptor-2), WT1 (Wilm' tumour gene), or may comprise e.g. mutant antigens expressed in cancer diseases selected from the group comprising, without being limited thereto, α-actinin-4/m, ARTC1/m, bcr/abl (breakpoint cluster region-Abelson fusion protein), β-Catenin/m (β-Catenin), BRCA1/m, BRCA2/m, CASP-5/m, CASP-8/m, CDC27/m (cell-division-cycle 27), CDK4/m (cyclin-dependent kinase 4), CDKN2A/m, CML66, COA-1/m, DEK-CAN (fusion protein), EFTUD2/m, ELF2/m (Elongation factor 2), ETV6-AML1 (Ets variant gene6/acute myeloid leukemia 1 gene fusion protein), FN1/m (fibronectin 1), GPNMB/m, HLA-A*0201-R170I (arginine to isoleucine exchange at residue 170 of the α-helix of the α2-domain in the HLA-A2 gene), HLA-A11/m, HLA-A2/m, HSP70-2M (heat shock protein 70-2 mutated), KIAA0205/m, K-Ras/m, LDLR-FUT (LDR-Fucosyltransferase fusion protein), MART2/m, ME1/m, MUM-1/m (melanoma ubiquitous mutated 1), MUM-2/m (melanoma ubiquitous mutated 2), MUM-3/m (melanoma ubiquitous mutated 3), Myosin class I/m, neo-PAP/m, NFYC/m, N-Ras/m, OGT/m, OS-9/m, p53/m, Pml/RARα (promyelocytic leukemia/retinoic acid receptor α), PRDX5/m, PTPRK/m (receptor-type proteintyrosine phosphatase κ), RBAF600/m, SIRT2/m, SYT-SSX-1 (synaptotagmin I/synovial sarcoma X fusion protein), SYT-SSX-2 (synaptotagmin I/synovial sarcoma X fusion protein), TEL-AML1 (translocation Ets-family leukemia/acute myeloid leukemia 1 fusion protein), TGFβRII (TGFβ receptor II), TPI/m (triosephosphate isomerase).

vii. Other Agents

A variety of other agents may be subject to vaccines developed in accordance with the present disclosure. For example, antigens to prions (proteinaceous infectious particles) that can give rise to diseases such as mad cow and kuru may be used in the compositions described herein. Also, antigens from small insects that embed themselves in the skin such as ticks, bed bugs or lice can be subject to a host immune response from the present compositions.

B. Diblock Copolymers

In some aspects, diblock copolymers described herein may act as adjuvants in immunogenic compositions. The pH-responsive micelles and nanoparticles disclosed herein comprise block copolymers. A block copolymer comprises a hydrophilic polymer segment and a hydrophobic polymer segment. The hydrophobic polymer segment is pH sensitive. For example, the hydrophobic polymer segment may comprise an ionizable amine group to render pH sensitivity. Within the hydrophobic polymer segment, multiple different monomers (e.g. 1, 2, 3, or more different monomers) may be used to adjust the $pK_a$ sensitivity of the hydrophobic polymer segment. The block copolymers form pH-activatable micellar (pHAM) nanoparticles based on the supramolecular self-assembly of these ionizable block copolymers. At higher pH, the block copolymers assemble into micelles, whereas at lower pH, ionization of the amine group in the hydrophobic polymer segment results in dissociation of the micelle. The ionizable groups may act as tunable hydrophilic/hydrophobic blocks at different pH values, which may directly affect the dynamic self-assembly of micelles.

In some aspects, the block copolymers have a pH transition value, which is the pH value that the block copolymer go from a nanoparticle to a dissociated form. The pH transition value may from 6.0 to 7.4, from 6.5 to 7.4, from 6.5 to 7.2, from 6.8 to 7.4, from 6.8 to 7.2, or from 6.0, 6.2, 6.4, 6.5, 6.6, 6.7, 6.8, 6.85, 6.9, 6.95, 7.0, 7.05, 7.1, 7.2 to 7.4, or any range derivable therein. In some aspects, the block copolymers form a nanoparticle with a particle size of less than 50 nm. In some embodiments, the nanoparticle may have a particle size from 1 nm to 50 nm, from 5 nm to 50 nm, from 10 nm to 50 nm, from 10 nm to 40 nm, from 20 nm to 40 nm, or from 5 nm, 10 nm, 15 nm, 20 nm, 22 nm, 24 nm, 26 nm, 28 nm, 30 nm, 32 nm, 34 nm, 35 nm, 40 nm, 45 nm to 50 nm, or any range derivable therein.

i. Hydrophilic Block

In some embodiments, the hydrophilic polymer segment comprises poly(ethylene oxide) (PEO). In some embodiments, the hydrophilic polymer segment comprises poly (methacrylate phosphatidyl choline) (MPC). In some embodiments, the hydrophilic polymer segment comprises polyvinylpyrrolidone (PVP). In general, the PEO, MPC, or PVP polymer in the hydrophilic polymer segment is about 2 kD to about 20 kD in size. In some embodiments, the polymer is about 2 kD to about 10 kD in size. In some embodiments, the polymer is about 2 kD to about 5 kD in size. In some embodiments, the polymer is about 3 kD to about 8 kD in size. In some embodiments, the polymer is about 4 kD to about 6 kD in size. In some embodiments, the polymer is about 5 kD in size. In some embodiments, the polymer has about 100 to about 130 monomer units. In some embodiments, the polymer has about 110 to about 120 monomer units. In some embodiments, the polymer has about 114 monomer units. Suitable hydrophilic polymer segments for use as the hydrophilic block of the diblock copolymer may be prepared using methods known in the art or may be purchased. For example, MPC polymers (e.g. narrowly distributed MPC polymers) can be prepared by atom transfer radical polymerization (ATRP) with commercially available small molecule initiators such as ethyl 2-bromo-2-methylpropanoate (Sigma Aldrich). These resulting MPC polymers can be used as macromolecular A TRP initiators to further copolymerize with other monomers to form block polymers such as MPC-b-PDPA. PEO-b-PR block copolymers can be synthesized using atom transfer radical polymerization (ATRP) or reversible addition fragmentation chain transfer (RAFT) methods (See e.g. Australian Journal of Chemistry Volume: 58 Issue: 6 Pages: 379-410 (2005); Progress in Polymer Science Volume: 32 Issue: 1 Pages: 93-146 (2007)). ATRP or RAFT allows for living polymerization which can yield PEO-b-PR copolymers with narrow polydispersity (<1.1). Different metharylate or acrylate monomers can be used to produce PR segments with different pH sensitivity.

ii. Hydrophobic Block

In some aspects, the hydrophobic polymer segment is prepared using amine containing methacrylate units which are pH sensitive. The hydrophobic polymer segment may comprise a polymer with x repeating units. In some embodiments, x is about 40 to about 100 in total. In some embodiments, x is about 50 to about 100 in total. In some embodiments, x is about 40 to about 70 in total. In some embodiments, x is about 60 to about 80 in total. The hydrophobic polymer segment may be synthesized according to, e.g. atom transfer radical Polymerization (ATRP) or reversible addition-fragmentation chain transfer (RAFT) or as described in the Examples below.

In some aspects, the hydrophobic polymer segment contains a repeating unit wherein $X_4$ and $X_5$ are an alkyl group with C1-C3 carbon atoms or are taken together and have C4-C8 carbon atoms. In some embodiments, these carbon atom lengths are optimized to obtain a hydrophobic polymer segment with a $pK_a$ from about 6.0 to about 7.5. In some embodiments, the $pK_a$ is from about 6.5 to about 7.4. $pK_a$ may be measured using methods known to a person of skill in the art such as a pH titration.

C. Additional Adjuvants

As also well known in the art, the immunogenicity of a particular immunogen composition can be enhanced by the use of non-specific stimulators of the immune response, known as adjuvants. Adjuvants have been used experimentally to promote a generalized increase in immunity against poorly immunogenic antigens (e.g., U.S. Pat. No. 4,877, 611). Immunization protocols have used adjuvants to stimulate responses for many years, and as such adjuvants are well known to one of ordinary skill in the art. Some adjuvants affect the way in which antigens are presented. For example, the immune response is increased when protein antigens are adsorbed to alum. Emulsification of antigens also prolongs the duration of antigen presentation and initiates an innate immune response. Suitable molecule adjuvants include all acceptable immunostimulatory compounds, such as cytokines, toxins or synthetic compositions.

In some aspects, the compositions described herein may further comprise another adjuvant. Although Alum is an approved adjuvant for humans, adjuvants in experimental animals include complete Freund's adjuvant (a non-specific stimulator of the immune response containing killed *Mycobacterium tuberculosis*), incomplete Freund's adjuvants and aluminum hydroxide adjuvant. Other adjuvants that may also be used in animals and sometimes humans include Interleukin (IL)-1, IL-2, IL-4, IL-7, IL-12, interferon, Bacillus Calmette-Guérin (BCG), aluminum hydroxide, muramyl dipeptide (MDP) compounds, such as thur-MDP and nor-MDP (N-acetylmuramyl-L-alanyl-D-isoglutamine MDP), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MHC antigens may even be used.

In one aspect, and approved for humans, an adjuvant effect is achieved by use of an agent, such as alum, used in about 0.05 to about 0.1% solution in phosphate buffered saline. Alternatively, in experimental animals the antigen is made as an admixture with synthetic polymers of sugars (Carbopol®) used as an about 0.25% solution. Adjuvant effects may also be achieved by aggregation of the antigen in the vaccine by heat treatment with temperatures ranging between about 70° to about 101° C. for a 30 second to 2-minute period, respectively. Aggregation by reactivating with pepsin treated (Fab) antibodies to albumin, mixture with bacterial cell(s) such as *C. parvum*, an endotoxin or a lipopolysaccharide component of Gram-negative bacteria, emulsion in physiologically acceptable oil vehicles, such as mannide mono-oleate (Aracel A), or emulsion with a 20% solution of a perfluorocarbon (Fluosol-DA®) used as a block substitute, also may be employed.

Some adjuvants, for example, certain organic molecules obtained from bacteria, act on the host rather than on the antigen. An example is MDP, a bacterial peptidoglycan. The effects of MDP, as with most adjuvants, are not fully understood, although the inventors are now beginning to understand that they activate cells of the innate immune system, e.g. dendritic cells, macrophages, neutrophils, NKT cells, NK cells, etc. MDP stimulates macrophages but also appears to stimulate B cells directly. The effects of adjuvants, therefore, are not antigen-specific. If they are administered together with a purified antigen, however, they can be used to selectively promote the response to the antigen.

In certain embodiments, hemocyanins and hemoerythrins may also be used in the compositions of the present disclosure. The use of hemocyanin from keyhole limpet (KLH) is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin.

Another group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative muramyl tripeptide phosphatidyle-thanolamide (MTPPE) are also contemplated.

U.S. Pat. No. 4,950,645 describes a lipophilic disaccharide-tripeptide derivative of muramyl dipeptide which is described for use in artificial liposomes formed from phosphatidyl choline and phosphatidyl glycerol. This is effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present disclosure.

BCG and BCG-cell wall skeleton (CWS) may also be used as adjuvants, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945. BCG is an important clinical tool because of its immunostimulatory properties. BCG acts to stimulate the reticuloendothelial system (RES), activates natural killer (NK) cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990). Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Lotte et al., 1984). It is one of the few vaccines that can be given at birth, it engenders long-lived immune responses with only a single dose, and there is a worldwide distribution network with experience in BCG vaccination. An exemplary BCG vaccine is sold as TICE BCG (Organon Inc., West Orange, N.J.).

Amphipathic and surface active agents, e.g., saponin and derivatives such as QS21 (Cambridge Biotech), form yet another group of adjuvants for use with the immunogens of the present disclosure. Nonionic block copolymer surfactants (Rabinovich et al., 1994) may also be employed. Oligonucleotides are another useful group of adjuvants (Yamamoto et al., 1988). Quil A and lentinen are other adjuvants that may be used in certain embodiments of the present disclosure.

Another group of adjuvants are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cCWS or CWS and trehalose dimycolate, as described in U.S. Pat. Nos. 4,436,727, 4,436,728 and 4,505,900. Combinations of just CWS and trehalose dimycolate, without detoxified endotoxins, are also envisioned to be useful, as described in U.S. Pat. No. 4,520,019.

Those of skill in the art will know the different kinds of adjuvants that can be conjugated to vaccines in accordance with this disclosure and which are approved for human vs experimental use. These include alkyl lysophosphilipids (ALP); BCG; and biotin (including biotinylated derivatives) among others. Certain adjuvants particularly contemplated for use are the teichoic acids from Gram⁻ bacterial cells. These include the lipoteichoic acids (LTA), ribitol teichoic acids (RTA) and glycerol teichoic acid (GTA). Active forms of their synthetic counterparts may also be employed in connection with the compositions of this disclosure (Takada et al., 1995).

Various adjuvants, even those that are not commonly used in humans, may still be employed in animals. Adjuvants may be encoded by a nucleic acid (e.g., DNA or RNA). It is contemplated that such adjuvants may be also be encoded in a nucleic acid (e.g., an expression vector) encoding the antigen, or in a separate vector or other construct. Nucleic acids encoding the adjuvants can be delivered directly, such as for example with lipids or liposomes.

D. Biological Response Modifiers (BRM)

In addition to adjuvants, it may be desirable to co-administer BRM, which have been shown to upregulate T cell immunity or downregulate suppressor cell activity. Such BRMs include, but are not limited to, cimetidine (CIM; 1200 mg/d) (Smith/Kline, PA); low-dose cyclophosphamide (CYP; 300 mg/m$^2$) (Johnson/Mead, NJ), cytokines such as—interferon, IL-2, or IL-12 or genes encoding proteins involved in immune helper functions, such as B-7. Additional biological response modifiers include those described in Gupta and Kanodia, 2002 and Bisht, et al., 2010, both of which are incorporated herein by reference.

E. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-α, MIP1-β, IP-10 and combinations thereof. The skilled artisan will recognize that certain cytokines are also known to have chemoattractant effects and could also be classified under the term chemokines.

F. Immunogenic Carrier Proteins

In some embodiments, the vaccine composition described herein may be chemically coupled to a carrier or recombinantly expressed with a immunogenic carrier peptide or polypetide (e.g., a antigen-carrier fusion peptide or polypeptide) to enhance an immune reaction. Exemplary and preferred immunogenic carrier amino acid sequences include hepatitis B surface antigen (HBSA), tetanus toxoid (TT), keyhole limpet hemocyanin (KLH) and BSA. In humans, TT would be advantageous since it is already an approved protein vaccine. For experimental animals, other albumins such as OVA, mouse serum albumin or rabbit serum albumin also can be used as immunogenic carrier proteins. Means for conjugating a polypeptide or peptide to an immunogenic carrier protein are well known in the art and include, for example, glutaraldehyde, m-maleimidobenzoyl-N-hydroxysuccinimide ester, carbodiimide and bis-biazotized benzidine.

II. Pharmaceutical Formulations and Methods of Treatment

A. Pharmaceutical Formulations and Routes of Administration

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

One will generally desire to employ appropriate salts and buffers to render the compositions stable and allow for uptake by target cells. Buffers also will be employed when the compositions are introduced into a patient. Aqueous compositions of the present disclosure comprise an effective amount of the vaccine composition, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the compositions of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the vaccine composition described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

One method for the delivery of a pharmaceutical composition according to the present disclosure is systemically. However, dependent upon the context, the pharmaceutical compositions disclosed herein may alternatively be administered parenterally, intravenously, subcutaneously, intradermally, intramuscularly, transdermally or even intraperitoneally as described in U.S. Pat. Nos. 5,543,158; 5,641,515 and 5,399,363 (each specifically incorporated herein by reference in its entirety).

Injection may be by syringe or any other method used for injection of a solution, as long as the agent can pass through the particular gauge of needle required for injection. A novel needleless injection system has been described (U.S. Pat. No. 5,846,233) having a nozzle defining an ampule chamber for holding the solution and an energy device for pushing the solution out of the nozzle to the site of delivery.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 mL of hypodermolysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "buffer or diluent" includes any and all solvents, dispersion media, vehicles, coatings, diluents, excipients, antibacterial and antifungal agents, isotonic and absorption delaying agents, buffers, solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrases "pharmaceutically-acceptable" or "pharmacologically-acceptable" refer to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

B. Methods of Treatment

In particular, the compositions that may be used in treating cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that inhibits the growth or proliferation of a bacterial cell, inhibits the growth of a biofilm, or induces death of cancerous cells (e.g., induces apoptosis of a cancer cell), as assayed by identifying a reduction in hematological parameters (complete blood count—CBC), or cancer cell growth or proliferation. In some embodiments, amounts of the meayamycin, thailanstatin A methyl ester, and analogs thereof used to induce apoptosis of the cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the vaccine compositions described herein may be more efficacious and thus a smaller dose is required to achieve a similar effect. Such a dose is typically administered once a day for a few weeks or until sufficient reducing in cancer cells has been achieved.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the disclosure provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

III. Combination Therapies

It is envisioned that the vaccine compositions described herein may be used in combination therapies with one or more additional therapies or a compound which mitigates one or more of the side effects experienced by the patient. It is common in the field of medicine to combine therapeutic modalities. The following is a general discussion of therapies that may be used in conjunction with the therapies of the present disclosure.

To treat a disease or disorder using the methods and compositions of the present disclosure, one would generally administer to the patient the composition and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the vaccine compositions and the other includes the other agent.

Alternatively, the vaccine compositions described herein may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations. Additionally, it is also contemplated that each of these therapies may be administered two or more times either in combination or individually. For example, a first therapy may be administered with a second therapy and then the first therapy may be administered a second time either alone or again in combination with the second therapy.

It also is conceivable that more than one administration of either the vaccine compositions or the other therapy will be desired. Various combinations may be employed, where a vaccine compositions of the present disclosure is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are also contemplated. The following is a general discussion of additional therapies that may be used combination with the compositions of the present disclosure.

A. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin γ1 and calicheamicin ω1; dynemicin, including dynemicin A; uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, or zorubicin; antimetabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein transferase inhibitors, transplatinum, 5-fluorouracil, vincristin, vinblastin and methotrexate and pharmaceutically acceptable salts, acids or derivatives of any of the above.

B. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

C. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

D. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurance of the tumor. Additionally, the compounds of the present disclosure can also be used in a neoadjuvant setting.

E. Other Agents

It is contemplated that other agents may be used with the present disclosure. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1$\beta$, MCP-1, RANTES, and other chemokines. It is further contemplated that the upregulation of cell surface receptors or their ligands such as Fas/Fas ligand, $DR_4$ or DR5/TRAIL (Apo-2 ligand) would potentiate the apoptotic inducing abilities of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents may be used in combination with the present disclosure to improve the anti-hyerproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

F. Antibiotics

The term "antibiotics" are drugs which may be used to treat a bacterial infection through either inhibiting the growth of bacteria or killing bacteria. Without being bound by theory, it is believed that antibiotics can be classified into two major classes: bactericidal agents that kill bacteria or bacteriostatic agents that slow down or prevent the growth of bacteria.

The first commercially available antibiotic was released in the 1930's. Since then, many different antibiotics have been developed and widely prescribed. In 2010, on average, 4 in 5 Americans are prescribed antibiotics annually. Given the prevalence of antibiotics, bacteria have started to develop resistance to specific antibiotics and antibiotic mechanisms. Without being bound by theory, the use of antibiotics in combination with another antibiotic may modulate resistance and enhance the efficacy of one or both agents.

In some embodiments, antibiotics can fall into a wide range of classes. In some embodiments, the compounds of the present disclosure may be used in conjunction with another antibiotic. In some embodiments, the compounds may be used in conjunction with a narrow spectrum antibiotic which targets a specific bacteria type. In some non-limiting examples of bactericidal antibiotics include penicillin, cephalosporin, polymyxin, rifamycin, lipiarmycin, quinolones, and sulfonamides. In some non-limiting examples of bacteriostatic antibiotics include macrolides, lincosamides, or tetracyclines. In some embodiments, the antibiotic is an aminoglycoside such as kanamycin and streptomycin, an ansamycin such as rifaximin and geldanamycin, a carbacephem such as loracarbef, a carbapenem such as ertapenem, imipenem, a cephalosporin such as cephalexin, cefixime, cefepime, and ceftobiprole, a glycopeptide such as vancomycin or teicoplanin, a lincosamide such as lincomycin and clindamycin, a lipopeptide such as daptomycin, a macrolide such as clarithromycin, spiramycin, azithromycin, and telithromycin, a monobactam such as aztreonam, a nitrofuran such as furazolidone and nitrofurantoin, an oxazolidonones such as linezolid, a penicillin such as amoxicillin, azlocillin, flucloxacillin, and penicillin G, an antibiotic polypeptide such as bacitracin, polymyxin B, and colistin, a quinolone such as ciprofloxacin, levofloxacin, and gatifloxacin, a sulfonamide such as silver sulfadiazine, mefenide, sulfadimethoxine, or sulfasalazine, or a tetracycline such as demeclocycline, doxycycline, minocycline, oxytetracycline, or tetracycline. In some embodiments, the compounds could be combined with a drug which acts against mycobacteria such as cycloserine, capreomycin, ethionamide, rifampicin, rifabutin, rifapentine, and streptomycin. Other antibiotics that are contemplated for combination therapies may include arsphenamine, chloramphenicol, fosfomycin, fusidic acid, metronidazole, mupirocin, platensimycin, quinupristin, dalfopristin, thiamphenicol, tigecycline, tinidazole, or trimethoprim.

G. Antivirals

The term "antiviral" or "antiviral agents" are drugs which may be used to treat a viral infection. In general, antiviral agents act via two major mechanisms: preventing viral entry into the cell and inhibiting viral synthesis. Without being bound by theory, viral replication can be inhibited by using agents that mimic either the virus-associated proteins and thus block the cellular receptors or using agents that mimic the cellular receptors and thus block the virus-associated proteins. Furthermore, agents which cause an uncoating of the virus can also be used as antiviral agents.

The second mechanism of viral inhibition is preventing or interrupting viral synthesis. Such drugs can target different proteins associated with the replication of viral DNA including reverse transcriptase, integrase, transcription factors, or ribozymes. Additionally, the therapeutic agent interrupts translation by acting as an antisense DNA strain, inhibiting the formation of protein processing or assembly, or acting as virus protease inhibitors. Finally, an anti-viral agent could additionally inhibit the release of the virus after viral production in the cell.

Additionally, anti-viral agents could modulate the bodies own immune system to fight a viral infection. Without being bound by theory, the anti-viral agent which stimulates the immune system may be used with a wide variety of viral infections.

In some embodiments, the present disclosure provides methods of using the disclosed compounds in a combination therapy with an anti-viral agent as described above. In some non-limiting examples, the anti-viral agent is abacavir, aciclovir, acyclovir, adefovir, amantadine, amprenavir, ampligen, arbidol, atazanavir, atripla, balavir, boceprevirertet, cidofovir, combivir, dolutegravir, daruavir, delavirdine, didanosine, docosanol, edoxudine, efavirenz, emtricitabine, enfuvirtide, entecavir, ecoliever, famciclovir, fomivirsen, fosamprenavir, foscarnet, fosfonet, ganciclovir, ibacitabine, imunovir, idoxuridine, imiquimod, indinavir, inosine, interferon type I, type II, and type III, lamivudine, lopinavir, loviride, maraviroc, moroxydine, methisazone, nelfinavir, nevirapine, nexavir, oseltamivir, penciclovir, peramivir, pleconaril, podophyllotoxin, raltegravir, ribavirin, rimantadine, ritonavir, pyramidine, saquinavir, sofosbuvir, stavudine, telaprevir, tenofovir, tenofovir disoproxil, tipranavir, trifluridine, trizivir, tromantadine, truvada, traporved, valaciclovir, valganciclovir, vicriviroc, vidarabine, viramidine, zalcitabine, zanamivir, or zidovudine. In some embodiments, the anti-viral agents is an anti-retroviral, a fusion inhibitor, an integrase inhibitor, an interferon, a nucleoside analogues, a protease inhibitor, a reverse transcriptase inhibitor, a synergistic enhancer, or a natural product such as tea tree oil.

It also should be pointed out that any of the foregoing therapies may prove useful by themselves in treating cancer or an infection thereof.

IV. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "- - - -" represents an optional bond, which if present is either single or double. The symbol " ==== " represents a single bond or a double bond. Thus, the formula

covers, for example,

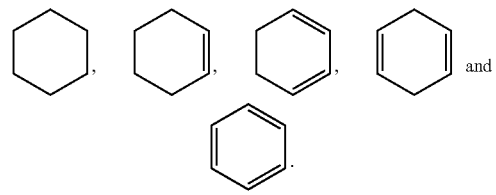

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " ∿∿∿ ", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀━" means a single bond where the group attached to the thick end of the wedge is "out of the page." The symbol " ⦀⦀⦀ " means a single bond where the group attached to the thick end of the wedge is "into the page". The symbol " ∿ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

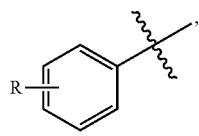

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

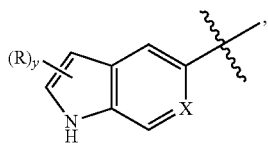

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom(s) in a moiety replacing a hydrogen atom is not counted. Thus methoxyhexyl, which has a total of seven carbon atoms, is an example of a substituted alkyl$_{(C1-6)}$.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or alkanediyl-NH-alkanediyl-. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

An "active ingredient" (AI) (also referred to as an active compound, active substance, active agent, pharmaceutical agent, agent, biologically active molecule, or a therapeutic compound) is the ingredient in a pharmaceutical drug or a pesticide that is biologically active. The similar terms active pharmaceutical ingredient (API) and bulk active are also used in medicine, and the term active substance may be used for pesticide formulations.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]

oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug) is a drug used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients (defined above) in pharmaceutical contexts.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present disclosure.

V. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Methods and Materials

A. Material

Monomers 2-(diethylamino)ethyl methacrylate (DEA-MA) and 2-aminoethyl methacrylate (AMA-MA) were purchased from Polyscience Company. Ovalbumin and $OVA_{257-263}$, CpG ODN were purchased from Invivogen. Imject Alum was purchased from Thermo Scientific, LPS and Poly(I:C) were purchased from Sigma-Aldrich. $OVA_{257-280}$ (SIINFEKLTEWTSSNVMEERKIKV (SEQ ID NO: 27)), $E7_{43-62}$ (GQAEPDRAHYNIVTFCCKCD (SEQ ID NO: 26)), $E7_{49-57}$ (RAHYNIVTF (SEQ ID NO: 28)), $Gp100_{21-41}$(VGALEGSRNQDWLGVPRQLVT (SEQ ID NO: 29)), $Trp1_{214-237}$(SHEGPAFLTWHRYHLLQLER-DMQE (SEQ ID NO: 5)), $Trp2_{173-196}$ (QPQIANCSVYDFFVWLHYYSVRDT (SEQ ID NO: 6)), $Obsl1_{T1764M}$ (EGVELCPGNKYEMRRHGTTHSLVIHD (SEQ ID NO: 7)), $Kif18b_{K739N}$(PSKPSFQEFVD-WENVSPELNSTDQPFL (SEQ ID NO: 10)), $Def8_{R255G}$ (SHCHWNDLAVIPAGVVHNWDFEPRKVS (SEQ ID NO: 30)), $Reps1_{P45A}$ (GRVLELFRAAQ-LANDVVLQIMELCGATR (SEQ ID NO: 31)), $Adpgk_{R304M}$ (GIPVHLELASMTNMELMSSIVHQQVFPT (SEQ ID NO: 32)), $Dpagt1_{V213L}$(EAGQSLVISASIIVFNL-LELEGDYR (SEQ ID NO: 33)) were synthesized by Biomatik. PEG-PLA was purchased from Advanced Polymer Materials Inc. (Montreal, QC, Canada). Other solvents and reagents were purchased from Sigma-Aldrich or Fisher Scientific Inc.

B. Syntheses of Methacrylate Monomers

Monomer AMA-MA was recrystallized twice in isopropanol and ethyl acetate (3:7) before use. Monomers including 2-(ethylpropylamino) ethyl methacrylate (EPA-MA), 2-(dipropylamino) ethyl methacrylate (DPA-MA), 2-(dibutylamino) ethyl methacrylate (DBA-MA) and 2-(dipentylamino) ethyl methacrylate (D5A-MA), 2-(pentamethyleneimino)ethyl methacrylate (C6A-MA), 2-(hexamethyleneimino)ethyl methacrylate (C7A-MA) were synthesized following previous publications (Zhou et al., 2011; 2012). New monomers including 2-(heptamethyleneimino)ethyl methacrylate (C8A-MA), 2-(4-methylpiperidineleneimino) ethyl methacrylate (C6S1A-MA), 2-(3,5-dimethylpiperidineleneimino)ethyl methacrylate (C6S2A-MA) were synthesized following a previously published procedure (Zhou et al., 2012). Below are the chemical characterizations of the new monomers:

2-(Heptamethyleneimino)ethyl methacrylate (C8A-MA): $^1$H NMR (TMS, CDCl$_3$, ppm): 6.10 (br, 1H, CHH=C (CH$_3$)—), 5.54 (br, 1H, CHH=C(CH$_3$)—), 4.19 (t, J=6.1 Hz, 2H, —OCH$_2$CH$_2$N—), 2.77 (t, J=6.1 Hz, 2H, —OCH$_2$CH$_2$N—), 2.60 (td, 4H, —N(CH$_2$CH$_2$CH$_2$)$_2$CH$_2$), 1.94 (m, 3H, CH$_2$=C(CH$_3$)—), 1.61 (tdd, 2H, —N(CH$_2$CH$_2$CH$_2$)$_2$CH$_2$), 1.54 (td, 8H, —N(CH$_2$CH$_2$)$_2$CH$_2$).

2-(4-Methylpiperidineleneimino)ethyl methacrylate (C6S1A-MA): $^1$H NMR (TMS, CDCl$_3$, ppm): 6.07 (br, 1H, CHH=C(CH$_3$)—), 5.53 (br, 1H, CHH=C(CH$_3$)—), 4.26 (m, 2H, —OCH$_2$CH$_2$N—), 2.88 (m, 2H, —OCH$_2$CH$_2$N—), 2.65 (m, 2H, —N(CHHCH$_2$)$_2$CHCH$_3$), 2.04 (tt, 2H, —N(CHHCH$_2$)$_2$CHCH$_3$), 1.92 (m, 3H, CH$_2$=C(CH$_3$)—), 1.59 (m, 2H, —N(CH$_2$CHH)$_2$CHCH$_3$), 1.31 (m, 1H, —CHCH$_3$), 1.21 (m, 2H, —N(CH$_2$CHH)$_2$CHCH$_3$), 0.89 (d, 3H, —CHCH$_3$).

2-(3,5-Dimethylpiperidineleneimino)ethyl methacrylate (C6S2A-MA): $^1$H NMR (TMS, CDCl$_3$, ppm): 6.09 (br, 1H, CHH=C(CH$_3$)—), 5.55 (br, 1H, CHH=C(CH$_3$)—), 4.28 (t, 2H, —OCH$_2$CH$_2$N—), 2.85 (ddt, 2H, —OCH$_2$CH$_2$N—), 2.66 (t, 2H, —N(CHHCHCH$_3$)$_2$CH$_2$), 1.94 (m, 3H, CH$_2$=C (CH$_3$)—), 1.68 (m, 3H, —N(CH$_2$CHCH$_3$)$_2$CHH), 1.57 (t, 2H, —N(CH$_2$CHCH$_3$)$_2$CH$_2$), 0.93 (d, 1H, —N(CH$_2$CHCH$_3$)$_2$CHH), 0.84 (d, 3H, —N(CH$_2$CHCH$_3$)$_2$CH$_2$).

C. Syntheses of PEG-b-PR Block Copolymers

PEG-b-PR copolymers were synthesized by atom transfer radical polymerization (ATRP) following similar procedures previously reported (Tsavrevsky et al., 2007). The dye free copolymers were used in polymer characterizations. PEG-b-PDPA is used as an example to illustrate the procedure. First, DPA-MA (1.48 g, 7 mmol), PMDETA (21 μL, 0.1 mmol), and MeO-PEG$_{114}$-Br (0.5 g, 0.1 mmol) were charged into a polymerization tube. Then a mixture of 2-propanol (2 mL) and DMF (2 mL) was added to dissolve the monomer and initiator. After three cycles of freeze-pump-thaw to remove the oxygen, CuBr (14 mg, 0.1 mmol) was added into the polymerization tube under nitrogen atmosphere, and the tube was sealed in vacuo. The polymerization was carried out at 40° C. for 10 hours. After polymerization, the reaction mixture was diluted with 10 mL THF, and passed through a neutral Al$_2$O$_3$ column to remove the catalyst. The THF solvent was removed by rotovap. The residue was dialyzed in distilled water and lyophilized to obtain a white powder. After syntheses, the polymers were characterized by $^1$H NMR and gel permeation chromatography (GPC).

D. Syntheses of PEG-b-(PR-r-Dye) Block Copolymers

AMA-MA was introduced in the PEG-b-PR copolymers for the conjugation of dyes. Synthesis of PEG-b-(PR-r-AMA) copolymers followed the procedure described above (Zhou et al., 2011; 2012). One primary amino group was introduced into each polymer chain by controlling the feeding ratio of AMA-MA monomer to the initiator (ratio=1). After synthesis, PEG-b-(PR-r-AMA) (10 mg) was dissolved in 2 mL DMF. Then the NHS-ester (1.5 equivalences for Dye-NHS) was added. After overnight reaction, the copolymers were purified by preparative gel permeation chromatography (PLgel Prep 10 m 10E3 Å 300×250 columns by Varian, THF as eluent at 5 mL/min) to remove the free dye molecules. The produced PEG-b-(PR-r-Dye) copolymers were lyophilized and kept at −20° C. for storage.

E. Preparation of Micelle Nanoparticles

Micelles were prepared following a solvent evaporation method as previously published (Zhou et al. 2012). In the example of PEG-b-PC7A, 10 mg of the copolymer was first dissolved in 1 mL methanol and then added into 4 mL distilled water dropwise under sonication. The mixture was filtered 4 times to remove THF using the micro-ultrafiltration system (MW=100 KD). Then distilled water was added to adjust the polymer concentration to 10 mg/mL as a stock solution. After micelle formation, the nanoparticles were characterized by dynamic light scattering (DLS, Malvern MicroV model, He—Ne laser, λ=632 nm) for hydrodynamic diameter (Dh).

F. OVA-PC7A Affinity Assay

The FRET experiment was designed to investigate the polymer and protein interaction at different ratio. In a typical procedure, the Cy3.5 conjugated PC7A (100 μg/mL) was incubated with Alexa Fluor 647-labelled OVA (20 μg/mL) in PBS buffer, pH 7.4. After 0.5 hours incubation, the fluorescence emission spectra were obtained on a Hitachi fluorometer (F-7500 model). The samples were excited at 590 nm, and the emission spectra were collected from 600 to 750 nm.

G. Lymph Node Imaging

To investigate whether NP can accumulate in the draining lymph nodes, the inventors labeled the PC7A copolymer with indocyanine green (ICG, $\lambda_{ex}/\lambda_{em}$=800/820 nm). ICG-encoded PC7A NP (30 μg per mice) was injected subcutaneously at the tail base of C57BL/6 mice. NP distribution was imaged using a clinical camera (SPY Elite®). Animals were sacrificed at 24 h after injection of NP, major organs and inguinal and axillary LNs were excised and imaged.

H. Peptide Introduction to the NP Through Disulfide Bond

To introduce the peptide into the core of the PC7A NP, PEG-b-P(C7A-r-AMA) and (succinimidyl 3-(2-pyridyldithio)propionate) (SPDP, 1.5 ratio to —NH$_2$ of PC7A) was dissolved by DMF in a flask. The mixture was stirred at room temperature for 24 h. The mixture was diluted with methanol and filtered 4 times to remove unreacted SDPD and byproduct. Then SH-peptide was dissolved in PBS, 7.4 and added into the polymer solution. After 6 h incubation, the mixture was filtered 4 times to remove unreacted peptide and byproduct. The peptide-PC7A conjugate was lyophilized and kept at −80° C. for storage. The preparation of micelle solution used the protocol described before. For the peptide conjugation on the surface of NP, the same procedure was used except that the Fmoc-PC7A was pretreated with piperidine for deprotection.

I. Animals and Cells

All animal procedures were performed with ethical compliance and approval by the Institutional Animal Care and Use Committee at the University of Texas Southwestern Medical Center. Female C57BL/6 mice (6-8 weeks) were obtained from the UT southwestern breeding core. INF-α/βR$^{-/-}$mice were kindly provided by Dr. David Farrar (UT Southwestern). STING$^{gt/gt}$ mice,MyD88$^{-/-}$mice, TRIF$^{-/-}$ mice C57BL/6-Tg (TcraTcrb)1100Mjb/J (CD45.2, H-2$^b$) (OT-I) mice, C57BL/6-CD45.1 mice were purchased from the Jackson laboratory. MyD88$^{-/-}$/TRIF$^{-/-}$ mice were crossed in our lab. cGas$^{-/-}$ mice were generated as previously described[4]. All these strains were maintained on C57BL/6J background. For each experiment, mice were randomly allocated by blinded investigators to each group. STING$^{gt/gt}$ and cGAS$^{-/-}$ BMDMs were derived from corresponding knockout mice, and then cultured in M-CSF containing medium for 6-7 days. THP-1 cells were purchased from ATCC and the inventors established THP-1 cell lines stably expressing shRNA targeting hSTING and hcGAS as described before (Collins et al., 2015), these THP-1 cell lines were grown in suspension RPMI media (Gibco) supplemented with 10% FBS, 0.05% β-mercaptoethanol (Sigma), and Pen/strep. B16-OVA cells were kindly provided by Dr. Patrick Hwu at MD Anderson Cancer Center, TC-1 cells were kindly provided by Dr. T. C. Wu at John Hopkins University, MC38 cells were kindly provide by Dr. Yangxin Fu (UT Southwestern). All cell lines were routinely tested using mycoplasma contamination kit (R&D). Cells were cultured in complete medium (DMEM, 10% fetal bovine serum, 100 U/mL penicillin G sodium and 100 µg/mL streptomycin (Pen/Strep), MEM non-essential amino acids (all from Invitrogen), and 20 µM β-mercaptoethanol(β-ME)) at 37° C. in 5% $CO_2$ and the normal level of $O_2$.

J. In Vivo Cytotoxicity Killing Assay

Groups of C57BL/6 mice were injected (OVA 10 µg plus nanoparticles 30 µg or other adjuvants with the same dose) subcutaneously at the tail base of C57BL/6 mice. Imject Alum (4 mg per mouse, 50 µl:50 µl mixture with the antigen solution) was used by volume ratio as recommended by manufacture. One week later, naïve C57BL/6 mice were sacrificed and spleenocytes were collected. Half of the spleenocytes were pulsed with $OVA_{257-263}$ or $E7_{49-57}$ peptides for 2 h in complete media at 37° C. The unpulsed and peptide-pulsed cells were labeled with 0.5 or 0.05 µM Carboxyfluorescein succinimidyl ester (CFSE), respectively, in serum free media for 15 mins. Equal numbers (1×10$^7$) of CFSE$^{low}$ (OVA pulsed cells) and CFSE$^{high}$ (unpulsed cells) were mixed together and injected intravenously into the immunized mice. After 16 h, the blood from treated mice was collected and subjected to flow cytometry analysis. The number of CFSE$^{high}$ and CFSE$^{low}$ was determined and used to calculate the percentage of OVA peptide-pulsed target cell killing. Specific killing was defined as percentage of specific lysis=[1-non-transferred control ratio/experimental ratio]×100.

K. ELISA Assay

For antibody detection, groups of C57BL/6 mice were immunized with different vaccines on day 0 and 14. On day 21, 50 µL of blood was drawn from tail vein and the antigen-specific IgG1 and IgG2c in serum were measured by ELISA. For ELISA assay, flat-bottomed 96-well plates (Nunc, Rochester, N.Y.) were precoated with OVA protein at a concentration of 0.5 µg protein/well in 50 mM carbonate buffer (pH 9.6) at 4° C. overnight, which were then blocked with 5% Glycine. Antisera obtained from immunized animals were serially diluted from 10$^2$ to 10$^6$ in PBS-0.05% Tween (PBS-T), pH 7.4, and were added to the wells and incubated at 37° C. for 1 h. Goat anti-mouse IgG1 and IgG2c (HRP) (Abcam, Cambridge, Mass.) were used at a dilution of 1:10,000 in PBS-T-1% BSA for labeling. After adding the HRP substrates, optical densities were determined at a wavelength of 450 nm in an ELISA plate reader (Bio-Rad, Hercules, Calif.).

L. In Vivo Cell Uptake Assay

For antigen delivery assay, subcutaneous injections at tail base of C57BL/6 mice were performed with PBS alone, OVA-AF647, or nanoparticle plus OVA-AF647 treatments. At 24 h post injection, mice were sacrificed and inguinal lymph nodes were removed, teased with 26 gauge needles and then passed through a 70-µm cell strainer (BD) to recover a cell suspension. The lymph node cell suspension was stained with PI and anti-CD11c-FITC, anti-CD11b-pacific blue, anti-B220-APC-Cy7, anti-CD8a-PE-Cy7. Four major APCs populations (CD8α$^+$DC cells (CD11c$^+$CD11b$^-$B220$^-$CD8α$^+$), CD8α$^-$DC cells (CD11c$^+$ CD8α$^-$), macrophage cells (CD11b$^+$ CD11c$^-$ B220$^-$), B cells (B220$^+$ CD11c$^-$)) were analyzed for the OVA-AF647 positive cells. APC maturation was measured by staining with anti-CD86-PE.

For nanoparticle uptake and STING activation assay, subcutaneous injections at tail base of C57BL/6 mice were carried out with PBS alone, or PC7A-Cy5 (30 µg) treatments. At 24 h post injection, mice were sacrificed, inguinal lymph nodes and subcutaneous tissue were removed, and digested in collagenase IV (Sigma-Aldrich) solution for 25 mins at 37° C. Tissue was then passed through a 70-µm cell strainer (BD) to recover a cell suspension. All the cell suspension were stained with PI and anti-CD11c-FITC, anti-MHCII-BV605, anti-CD45.2-Apc-Cy7. For intracellular pIRF3 staining, cells were permeabilized by the Fixation/Permeabilization kit (BD Cat #554714). After blocking with mouse serum, cells were stained with pIRF3 antibody (Cell Signaling, Cat #4947) and subsequently were stained with anti-rabbit IgG-PE secondary antibody (Biolegend). Flow cytometry (LSRII, BD) was performed on stained cell suspensions and analyzed with FlowJo® software (Tree Star Inc. Ashland, Oreg.).

M. In Vitro Uptake and Cross Presentation Assay

Bone marrow-derived dendritic cells were generated by culturing bone marrow cells flushed from femurs of C57BL/6J mice in DC media: DMEM supplemented with 10% FBS, pen/strep, sodium pyruvate and 20 ng/mL GM-CSF. Media was half replaced every 2 days; non-adherent and loosely adherent immature dendritic cells (DCs) were collected on day 6 and phenotyped by determining expression of CD11c (routinely 60-80% CD11c$^+$). OVA-AF647 (2 ug/mL) or mixture of OVA-AF647 with different nanoparticles (50 µg/mL) was incubated with murine bone marrow-derived dendritic cells (BMDCs) at 37° C. for 4 hours and quantified using the mean fluorescence intensity (MFI) of cells by FACS. For cross presentation assay, BMDCs were incubated with OVA alone or mixture of OVA with different nanoparticles at 37° C. for 18-20 hours, then the $OVA_{257-267}$ presented on the MHC-I on cell surface were detected by monoclonal antibody 25mAb-D1.16, an antibody specifically recognize OVA peptide SIINFEKL bound to H-2K$^b$.

N. In Vitro and In Vivo CD8+ T Cell Priming Assays

To evaluate antigen presentation by OVA-NP-pulsed BMDCs, IFN-γ secretion by primed OT-I T cells was used to quantify CD8$^+$ T-cell activation. Briefly, BMDCs were incubated with 3 µg/mL OVA alone or mixture of OVA with different nanoparticles (50 µg/mL) at 37° C. for 18 h. CD8$^+$ T lymphocytes from OT-I mice were selected by magnetic separation (MACS system; Miltenyi Biotec, Bergisch Gladbach, Germany) according to the manufacturer's indications. The purity of CD8$^+$ T lymphocytes was >95%. CD8$^+$ T cells were plated at 2×10$^5$ cells/well in 96-well plates (Costar; Corning, Inc., Corning, N.Y.) in RPMI media containing 10% FCS and 2×10$^5$ unpulsed, or antigen-pulsed BMDCs that were added for 24 h. Cell culture supernatants were collected and analyzed for cytokine content using mouse TH1/TH2 9-Plex Ultra-sensitive Kit (Meso Scale Discovery). Samples were run in triplicate.

Spleens were harvested from B6 CD45.2$^+$ OT-I mice, CD8$^+$ T cells from cell suspensions were isolated by magnetic bead separation on a MACS column. $5\times10^4$ OT-1 CD8$^+$ T cells were transferred into B6 CD45.1$^+$ mice via intravenous (i.v.) injection and allowed to acclimate for 1 day prior to immunization. 1 day later, groups of CD45.1$^+$ mice were immunized with PBS alone, OVA(10 µg), or nanoparticle (30 µg) plus OVA subcutaneously at the tail base. One week later, spleens were harvested and dispersed into single-cell suspensions, stained with anti-CD8-PE-cy7, APC-conjugated H-2Kb/OVA (SIINFEKL) tetramer (NIH) for flow cytometry analysis.

O. Hemolysis Assay

The capacity of polymers to promote pH-dependent disruption of lipid bilayer membranes was assessed via a red blood cell hemolysis assay as previously described (Wilson et al., 2013). Polymers were incubated for 1 h at 37° C. in the presence of mouse erythrocytes at 20 µg/mL in 100 mM sodium phosphate buffer (supplemented with 150 mM NaCl) in the pH range of the endosomal processing pathway (7.4, 7.2, 7.0, 6.8, 6.6, and 6.4). The extent of cell lysis (i.e., hemolytic activity) was determined spectrophotometrically by measuring the amount of hemoglobin released (A541 nm). Hemolytic activity was normalized to a 100% lysis control (1% Triton X-100 treated red blood cells). Samples were run in triplicate.

P. Flow Cytometry

Antibodies were purchased from Biolegend. The following primary antibodies were used: anti-CD16/CD32 (Biolegend, Cat #: 101301, clone: 93), anti-CD8-PE-cy7 (Biolegend, Cat #: 100721, clone: 53-6.7), anti-CD11c-FITC (Biolegend, Cat #: 117305, clone: N418) and anti-CD11b-Pacif blue (Biolegend, Cat #: 101223, clone: M1/70), anti-B220-APC-cy7 (Biolegend, Cat #: 103223, clone: RA3-6B2), anti-CD86-PE (Biolegend, Cat #: 105007, clone: GL-1), anti-H-2K$^b$ bound to SIINFEKL-APC (Biolegend, Cat #:141605, clone:25-D1.16), anti-CD45.2-APC (Biolegend, Cat #:109814, clone:104), anti-CD45.2-APCcy7 (Biolegend, Cat #:109823, clone:104), anti-PD-L1-PE (Biolegend, Cat #:124307, clone:10F.9G2), isotype control-PE (Biolegend, Cat #:400607, clone:RTK4530), anti-F4/80-PE/cy7 (Biolegend, Cat #:123113, clone:BM8), anti-Gr-1-FITC (Biolegend, Cat #:108419, clone:RB608C5), anti-MHCII-BV605 (Biolegend, Cat #:107639, clone:M5/114.15.2), anti-rabbit IgG-PE (Biolegend, Cat #:406421, clone:poly4064). Flow data were acquired on a BD™ LSR II flow cytometer and analyzed using Flowjo® software.

Q. RT-PCR

Subcutaneous tissues were taken at indicated time points after injection with OVA-PC7A NP (OVA 10 µg, PC7A 150 µg) or the same dose of different adjuvants. To obtain BMDM, about $1\times10^7$ bone marrow cells were cultured in DMEM containing 10% FBS, antibiotics and conditioned media from L929 cell culture. After 6 to 7 days, mature macrophages were harvested and cultured on 12-well plates for experiments (Collins et al., 2015). Total RNAs were extracted by TRIzol (Invitrogen) from cells or tissues according to the manufacturer's instructions. q-RT-PCR were performed as previously described (Li et al., 2013; Collins et al., 2015). Samples were run in triplicate. The following primers were used for q-RT-PCR.

```
mIRF7:
                                    (SEQ ID NO: 16)
ATGCACAGATCTTCAAGGCCTGGGC;

(SEQ ID NO: 17)
GTGCTGTGGAGTGCACAGCGGAAGT;

mCXCL10:
                                    (SEQ ID NO: 18)
GCCGTCATTTTCTGCCTCA;

(SEQ ID NO: 19)
CGTCCTTGCGAGAGGGATC;

mRPL19:
                                    (SEQ ID NO: 20)
AAATCGCCAATGCCAACTC;

(SEQ ID NO: 21)
TCTTCCCTATGCCCATATGC;

hCXCL10:
                                    (SEQ ID NO: 22)
TGGCATTCAAGGAGTACCTC;

(SEQ ID NO: 23)
TTGTAGCAATGATCTCAACACG;

hGAPDH:
                                    (SEQ ID NO: 24)
ATGACATCAAGAAGGTGGTG;

(SEQ ID NO: 25)
CATACCAGGAAATGAGCTTG.
```

R. Immunization and Tumor Therapy Experiments.

Six to eight week old mice (n=10 for each group) were injected subcutaneously with B16-OVA or B16F10 melanoma cells ($1.5\times10^5$), or TC-1 cells ($1.5\times10^5$), MC38 cells ($5\times10^5$) into the right flank of mice. Animals were immunized with subcutaneous injection at the tail base of antigen-polymer NP (0.5 µg per antigen peptide, PC7A NP 30 µg) or the same dose of different adjuvants as described in the main text. Or at day 3, 6, 9 and 12, some groups were i.p. injected with 200 µg checkpoint inhibitors (anti-mPD-1, BioXcell, BE0146) for comparison or synergy evaluation. The tumor growth was subsequently measured twice a week using a digital caliper and calculated as $0.5\times length\times width^2$ by blinded investigators. Mice were killed when tumor surface area reached 1500 mm$^3$, the end point of tumor detection is 2-fold of the longest survival time (LST) of control group, so around 40 days for melanoma tumor model, and around 60 days for TC-1 and MC38 tumor models.

For PD-L1 expression analyses, tumor tissues were digested by 1 mg/mL collagenase IV (Sigma-Aldrich) and 0.2 mg/mL DNase I (Sigma-Aldrich) for 45 minutes at 37° C. Cells were then stained with antibodies against PD-L1, CD11b, Gr-1, F4/80, CD11c, and CD45 (Biolegend).

S. Statistical Analysis

Based on pilot immunization and tumor treatment studies, the inventors used group sizes of 3-6 animals/group for immunogenicity measurements and 10 animals/group for tumor therapy experiments. Statistical analysis was performed using Microsoft Excel and Prism 5.0 (GraphPad). Data are expressed as means±s.e.m. Data were analyzed by Student's t test. Variance similarity test (f-test) was performed before t-test. All t-tests were one-tailed and unpaired, and were considered statistically significant if $p<0.05$, (*, $p<0.05$; , $p<0.01$; *, $p<0.001$ unless otherwise indicated). The survival rates of the two groups were analyzed using a log-rank test and were considered statistically significant if $p<0.05$.

T. Polymer Nanovaccine

The pH-sensitive polymer library of PEG-b-PR with 70 repeating unit of PR segment was synthesized using an atom transfer radical polymerization method. Dye conjugated polymers were synthesized by reacting PEG-b-PR(NH$_2$) with NHS-Dye in N,N-dimethylformamide. The PC7A nanovaccine was freshly prepared by physical mixing of the PC7A nanoparticle with protein or peptide antigens in water.

U. Immunization

C57BL/6 mice (female, 6-8 weeks old, Breeding Core on campus) were immunized with nanovaccines in 100 μL PBS solution subcutaneously injected at the tail base. All animal procedures were approved by the Institutional Animal Care and Use Committee at the University of Texas Southwestern Medical Center.

V. DNase I Transfection

BMDMs were transfected with 5 μg of DNase I (Roche) by transfection reagent DOTAP (Roche) according to manufacturer's instructions. After incubating the cells with DOTAP-DNase I or DOTAP alone for 1 hr, cells were washed to remove excess of transfection reagent and enzyme and were then incubated with PC7A at 400 μg/ml for 9 hr. CXCL10 were measured by RT-PCR.

W. STING Pulldown Assay

To investigate the STING interaction with PC7A copolymer, the inventors labeled the PC7A copolymer with biotin (2-3 biotins per polymer chain). For THP-1 cell pulldown assay, PC7A-biotin (200 μg/ml) was incubated with THP-1 cells for 8 hrs, and then cells were collected and lysed in RIPA buffer (Sigma R0278). Lysates were precipitated with streptavidin-modified dynabeads (BD 557812). Samples were analyzed using SDS-PAGE and Western blots by rabbit anti-STING antibody (Cell Signaling, Cat #13647). For STING protein pull down assay, human STING CTD (139-379) expression and purification had been described before[7]. PC7A-biotin (50 μg/mL) was incubated with STING CTD (1 μg/ml) for 3 hrs in PBS (pH=6.8), PEPA-biotin in PBS (pH=6.8) and PD5A-biotin in PBS (pH=4.4) with the same concentration were used as control groups, and then precipitated with streptavidin-modified dynabeads. Samples were analyzed using SDS-PAGE and Western blots.

X. Isothermal Titration Calorimetry (ITC)

ITC was employed to measure the binding affinities between STING CTD and PC7A polymers or cGAMP using a VP-ITC microcalorimeter (GE Healthcare), ITC of PC7A-bovine serum albumin (BSA) was used as a negative control. The titrations were performed at 20° C. in the buffer containing 25 mM HEPES (pH 6.8), 150 mM NaCl. Thirty-two injections were performed with 4 min spacing time. The titration traces were integrated by NITPIC, and then the curves were fitted by SEDFIT (Zhang et al., 2013). The figures were prepared using GUSSI (biophysics.swmed.edu/MBR/software.html).

Y. IDO Enzyme Activity Assay in Tissues

Bacterial pDNA (pEGFPN1, Clontech) was prepared using an endotoxin-free Kit (Qiagen). Mice were intravenously injected with 30 μg pDNA mixed with in vivo-jetPEI (Polyplus-transfection, N:P=8) or were injected s.c. with NPs (150 μg, 5-fold of vaccine dose). IDO activity was measured as described in previous reports (Huang et al., 2012; Hoshi et al., 2010). In brief, tissues were removed 24 hr after immunization, and homogenized in 1.5 volumes of ice-cold 0.14M KCl-20 mM potassium phosphate buffer (pH 7). The homogenate samples were centrifuged at 7000×g and 4° C. for 10 min. Then 50 μl of supernatant was mixed with 50 μl substrate solution. The composition of the substrate solution was 100 mM potassium phosphate buffer (pH 6.5), 50 μM methylene blue, 20 μg catalase, 50 mM ascorbate, and 0.4 mM L-TRP. After incubation of the reaction mixture at 37° C., samples were acidified with 3% perchloric acid and centrifuged at 7000×g and 4° C. for 10 min. The concentrations of the products were measured by HPLC. Enzyme activity was expressed as the product content per hour per gram of tissue protein.

Z. OVA Loading and Stability Studies

OVA loading efficiency inside micelle nanoparticles was measured by an ultrafiltration method. Briefly, micelle nanoparticles (300 μg/mL) from different polymers were mixed with AF647-labelled OVA (100 μg/mL) for 30 min. After OVA loading, free OVA was removed from OVA-loaded nanoparticles by ultrafiltration tube with a molecular weight cutoff of 100 kD. The concentration of free OVA was measured on a Hitachi fluorometer (F-7500 model) with excitation wavelength at 640 nm. The loading efficiency was calculated using the equation below:

$$\text{Loading Efficiency} = \frac{\text{Total } OVA - \text{Free } OVA}{\text{Total } OVA} \times 100\%$$

To evaluate the loading stability, OVA-loaded PC7A nanoparticles were incubated in PBS buffer (pH 7.4) containing 5% fetal bovine serum over different times. Free OVA was separated and determined as described above.

The FRET experiment was further designed to investigate the polymer and OVA interactions. In a typical procedure, Cy3.5-conjugated PC7A (100 μg/mL) was incubated with AF647-labelled OVA (20 ug/mL) in PBS buffer (pH=7.4). After 30 min incubation, the fluorescence emission spectra were obtained on a Hitachi fluorometer (F-7500 model). The samples were excited at 590 nm, and the emission spectra were collected from 600 to 750 nm.

Eight week-old female B6 WT mice were primed via i.m. vaccination with 1 μg H1N1 PR8 (influenza A virus A/PR/8/1934(H1N1) hemagglutinin (HA) antigen together with either PC7A [200 μg PC7A/mouse], Alum [1:1 vol/vol ratio], or endotoxin-free H$_2$O. Ten days post-prime, mice were boosted with 0.5 μg H1N1 PR8 HA together with either 200 μg PC7A/mouse], Alum [1:1 vol/vol ratio], or endotoxin-free H$_2$O. Serum was harvested from vaccinated mice on Day 17 (one week post-boost).

For ELISA, plates were coated with H1N1 HA PR8 antigen (5 μg/mL in PBS) overnight at 4° C. Plates were blocked with TBS-3% (wt/vol) bovine serum albumin (BSA). Samples were added to plate at a 1:10000 dilution. After washing of plate, HRP-conjugated goat anti-mouse IgG (H+L) was added at a 1:5000 dilution. For IgG1 and IgG2b detection, HRP-conjugated goat anti-mouse IgG1 or IgG2b antibodies were added at a dilution of 1:5000. The plate was developed with 3,3',5,5'-tetramethylbenzidine substrate and the OD at 450 nm was measured.

For influenza challenge, influenza A/PR/8/34 (H1N1) virus was diluted in sterile PBS to 10× (700 pfu/mouse) MLD$_{50}$. Mice were sedated using ketamine (30 mg/ml)/xylazine (4 mg/ml) intraperitoneally (i.p.) and virus was administered intranasally in a total volume of 40 μL, split evenly between nares. After virus challenge, mice received atipamezole (0.63 mg/ml) i.p. and were subsequently monitored for weight loss and mortality for 14 days. Mice were humanely sacrificed when weight loss exceeded 30%.

Example 2

Data and Discussion

Successful production of tumor-specific CD8 T cell response requires spatio-temporal control of transport of tumor antigens to the secondary lymphoid organs, cytosolic delivery and cross-presentation in the antigen presenting cells (APCs) in coordination with innate stimulation. Immunotherapy using nanoparticles is an emerging area with recent advances focusing on the immunogenecity advantage of viral nanoparticles (Lizotte et al., 2016). Although non-viral nanoparticles (<50 nm in diameter) can selectively accumulate inside the lymph nodes (Reddy et al., 2007; Liu et al., 2014), few studies had shown their ability to simultaneously promote antigen presentation and stimulate innate immune response without incorporation of adjuvants (e.g., CpG, Poly(I:C)). Recently, the inventors' lab has established a library of ultra-pH sensitive (UPS) nanoparticles (20-50 nm in diameter) that are finely tunable in a broad range of physiological pH (4-7.4) (Ma et al., 2014). Once taken up by cells through macropinocytosis, these UPS nanoparticles can buffer the luminal pH of endocytic organelles at specific pH values (Wang et al., 2015). Inspired by "proton sponge" polymers for cytosolic delivery of biologics (Boussif et al., 1995) and small nanoparticle size for LN targeting, the inventors performed an in vivo screening of UPS nanoparticles to evaluate their abilities in generating cytotoxic T lymphocyte (CTL) response. The UPS library consists of copolymers containing tertiary amines with linear or cyclic side chains (FIG. 1A and FIG. 5A) with each component rendering sharp pH buffering at corresponding pKa (FIGS. 5B-C). Ovalbumin (OVA) was used as a model antigen. OVA loading efficiency was measured to be >75% across different polymer nanoparticles (FIG. 6A).

OVA-specific CTL response was quantified by an established in vivo cytotoxicity assay (FIG. 1A) (Barber et al., 2015). Briefly, OVA-polymer NP was first injected subcutaneously at the tail base of C57BL/6 mice. After 7 days, OVA epitope (SIINFEKL) specific CTL effect was determined by measuring the killing rate of CFSE-labeled target cells. Flow cytometry data showed that PC7A NP allowed the highest OVA-specific splenocyte killings (82%) compared to other cyclic amines (e.g., PC6A, substituted PC6As and PC8A) as well as linear tertiary amines (FIG. 1B). PC7A NP yielded approximately two-fold stronger CTL response compared to PC6S1A and PEPA NPs with comparable pKa's (6.9-7.0). In the linear series, PEPA had the highest CTL response compared to other copolymers. These data suggest that both pH transition (i.e., 6.9 that targets early endosomal pH) and polymer architecture (i.e., cyclic seven-membered ring) of UPS copolymers are important to induce strong CTL response. Conventional PEG-b-poly(D, L-lactic acid) (PEG-PLA) micelles had a weak CTL response (4.2%) (Maldonado et al., 2015). OVA-PC7A NP induced approximately 20-fold higher CTL response over OVA-Alum (4.3%) or OVA-LPS that stimulates the $TLR_4$ pathway (3.7%) (Poltorak et al., 1998), and 3.6-fold higher than OVA-CpG that stimulates the TLR9 pathway (23%) (Hemmi et al., 2000). In addition, OVA-specific antibody responses from the sera of immunized mice collected 7 days after boosting showed that mice vaccinated with PC7A NP generated similar titers of OVA-specific IgG1 response comparable to those by Alum or LPS (FIG. 1C). PC7A NP also generated similar titers of OVA-specific IgG2c antibody compared to those immunized with OVA plus CpG or LPS (FIG. 1D). Altogether, the inventors conclude that PC7A NP was able to induce a robust antigen-specific CTL, Th1 and Th2 responses with comparable or better efficacy than several established adjuvants.

To investigate the APC targeting ability of PC7A NP, the inventors first labeled PC7A copolymer with indocyanine green ($\lambda_{ex}/\lambda_{em}$=800/820 nm) and used a clinical camera (SPY Elite®) to image nanoparticle transport into draining lymph nodes (dLNs) after subcutaneous injection at the tail base. Results show efficient accumulation of PC7A NP (29 nm in diameter) in the peripheral lymph nodes at 24 h (FIG. 7A). Other organs did not show significant accumulation. To investigate the ability of PC7A NP for antigen delivery, the inventors first verified that OVA can be encapsulated in the PC7A micelles by strong FRET effect (FIGS. 6C-E), and the encapsulation was relatively stable in 5% serum over 24 h (FIG. 6B). They then used Alexa Fluor 647-labelled OVA with and without PC7A micelle encapsulation and harvested the dLNs 24 h after subcutaneous injection. Flow cytometry was performed to quantify the percentage of OVA-positive cells in $CD8\alpha^+$ and $CD8\alpha^-$ dendritic cells (DCs) and macrophages. All three subpopulations showed a significantly higher OVA accumulation by PC7A-mediated delivery over OVA alone (FIG. 2A). LN-resident $CD8\alpha^+$ DC cells were known to be important for induction of CTL response (Hildner et al., 2008; Sancho et al., 2008). The amount of OVA-positive $CD8\alpha^+$ DCs increased 29-fold in OVA-PC7A NP group over the OVA only control.

The inventors investigated the ability of PC7A NP on cytosolic delivery and cross-presentation of antigens (Heath et al., 2004) using several in vitro cell culture assays (FIG. 2B). Incubation of OVA-PC7A NP with bone marrow derived dendritic cells (BMDCs) showed similar antigen uptake compared to OVA-PD5A NP and less than the OVA only group (FIG. 2C). In contrast, OVA peptide (SIINFEKL)-MHC-I complex as detected by mAb25-D1.16 illustrated 3-fold antigen cross-presentation over the two control groups (FIG. 2D). Using an in vitro OT-I $CD8^+$ T cell priming assay, BMDCs treated with OVA-PC7A NP dramatically increased the IFN-γ secretion of $CD8^+$ T cells isolated from OT-I mice over the other control groups (FIG. 2E). This result was further supported by in vivo $CD8^+$ T cell priming assay, where OVA epitope (SIINFEKL) specific $CD8^+$ T cells showed 15-fold higher proliferation in OVA-PC7A NP group over OVA only group (FIG. 2F-G). Further evidence on endosomal disruption for cytosolic delivery was illustrated by a hemolysis assay in red blood cells (RBCs) at different pH values (Wilson et al., 2013). Results showed that PC7A NP had no hemolytic effect at pH 7.4 in the micelle state but displayed a strong hemolytic activity (~90%) at pH below 7.0 upon micelle dissociation. PD5A NP did not show any observable RBC hemolysis in the same pH range (FIGS. 8A-B).

Costimulatory signals (e.g., CD80/86) and cytokines are also necessary to induce a strong tumor-specific CTL response (Liechtenstein et al., 2012). In the previous experiments, at 24 h post immunization with OVA-PC7A NP, the inventors found that the inguinal LNs appeared to increase in size compared with OVA alone (FIG. 7B). The total cell number in the inguinal LNs from OVA-PC7A NP-treated mice increased by >2-fold over OVA-PD5A or OVA alone controls (FIG. 7C). Flow cytometry analysis showed significantly higher expression of CD86 in different subgroups of APCs from mice treated by OVA-PC7A NP over three other control groups (FIG. 3A and FIG. 7D). Type I IFNs have been shown to boost the effectiveness of the $CD8^+$ T cell response (Zitvogel et al., 2015; Fuertes et al., 2013). The inventors examined the expressions of IFN-stimulated genes (ISGs) in the local tissues (Trinchieri et al., 2010) over time after subcutaneous injection of PC7A NP. Poly(I:C) was used as a positive control (Alexopoulou et al., 2001). Results show that Poly(I:C) was able to elicit higher response in IRF7 and CXCL10 expressions in the early time points from 2 to 8 h than PC7A NP. At 24 h, PC7A NP produced stronger responses than both Poly(I:C) and PD5A NP groups (FIGS. 3B-C).

To confirm the impact of IFN pathway on CTL response, the inventors measured the OVA-specific CTL and Th1 response in IFN receptor (IFN-α/βR$^{-/-}$) knockout mice. Data show majority of the CTL/Th1 response was abolished in IFN-α/βR$^{-/-}$ mice compared to wild type control (FIGS. 3D-F, n=5), which is consistent with the ISG expression data. Toll-like receptors (TLR), MAVS and STING are known to activate the type I interferon pathways (Zitvogel et al., 2015; Baccala et al., 2007).

To further elucidate the mechanism, the inventors analyzed the immune response in MyD88$^{-/-}$/TRIF$^{-/-}$, MAVS$^{-/-}$ and STING$^{gt/gt}$ mice. Results show that T cell response induced by PC7A NP was not dependent on TLR and MAVS pathways, whereas STING$^{gt/gt}$ mice almost recapitulated the outcome in IFN-α/βR$^{-/-}$ mice (FIGS. 3D-F). Cyclic GMP-AMP synthase (cGAS) can sense cytosolic DNA and produce cyclic GMP-AMP (cGAMP), which subsequently activates STING, leading to induction of type I IFNs (Sun et al., 2013). Additional studies in cGAS$^{-/-}$ mice showed CTL response was partially dependent on cGAS. The roles of STING and cGAS in ISG induction were further confirmed by in vitro cell culture results using bone marrow derived macrophages and human monocyte THP-1 cells (FIGS. 9A-B). To further evaluate the role of cytosolic DNA in this process, the inventors transfected DNase I into BMDMs before PC7A treatment (Carroll et al., 2016), and found that the PC7A-induced ISG level in WT BMDMs decreased to almost the same level as in cGAS$^{-/-}$ BMDMs (FIG. 9C). This result suggests that cytosolic DNA is partially responsible for cGAS-dependent STING activation. For cGAS-independent STING activation, the inventors performed a STING pulldown assay using biotin-conjugated PC7A NP incubated with THP-1 cells. Cell lysis and protein pulldown by streptavidin-modified dynabeads show that only PC7A-biotin was able to retain STING but not PD5A-biotin and PC7A-only (biotin free) controls (FIG. 9D). Further study with purified C-terminal domain (CTD, 139-397 AAs) of STING show STING CTD pulldown in the absence of other proteins (FIG. 9E), suggesting direct binding between STING and PC7A. This is further supported by isothermal calorimetry (ITC) experiment where PC7A titration of STING in HEPES buffer showed a dissociation constant (Kd) of 1.3 μM (FIGS. 9F-G). This interaction is weaker compared to cGAMP-STING complex (Kd=9.6 nM). In contrast, negligible binding was found between PC7A and bovine serum albumin in the negative control. Although the inventors could detect a specific interaction between PC7A and STING, further structural and functional studies are required to determine if PC7A can activate STING through direct binding.

Next, the inventors sought to identify the major cell populations that are responsible for nanoparticle uptake and STING activation. Cy5-labeled PC7A polymer was employed to quantify NP uptake in cells and phosphorylated IRF3 (pIRF3) was used to detect the activation of STING-type I IFN pathway (Woo et al., 2014). One day after subcutaneous injection Cy5-PC7A NP, they collected the inguinal LNs and subcutaneous tissue at injection site and produced single cell suspensions. Flow cytometry analysis revealed that in LNs, NP+ cells had significantly elevated pIRF3 expressions over NP-cells and CD45+ leukocytes in the PBS control (FIG. 10A). Further analysis showed that 87% of NP+ cells expressed a DC cell marker (CD11c+) which was further corroborated by MHC-II+ expression (FIG. 10B). The same analysis was performed on cell suspension from the injection site (FIG. 10C). Data show CD45+ leukocytes internalized significantly higher amount of PC7A NPs than CD45− cells. In the CD45− cell population, the inventors did not observe any significant increase in the pIRF3 levels. In the CD45+ cell population, significantly elevated pIRF3 levels were found in the NP+ cells over NP− cells. Further analysis of CD45+NP+ cells showed 95% of cell population have CD11c+ marker (lower panel in FIG. 10D). Based on these data, the inventors conclude that at both the injection site and draining LNs, APCs (especially DCs) were the major cell population that took up PC7A NPs and subsequently activated STING-type I IFN pathway.

Figure 9J:
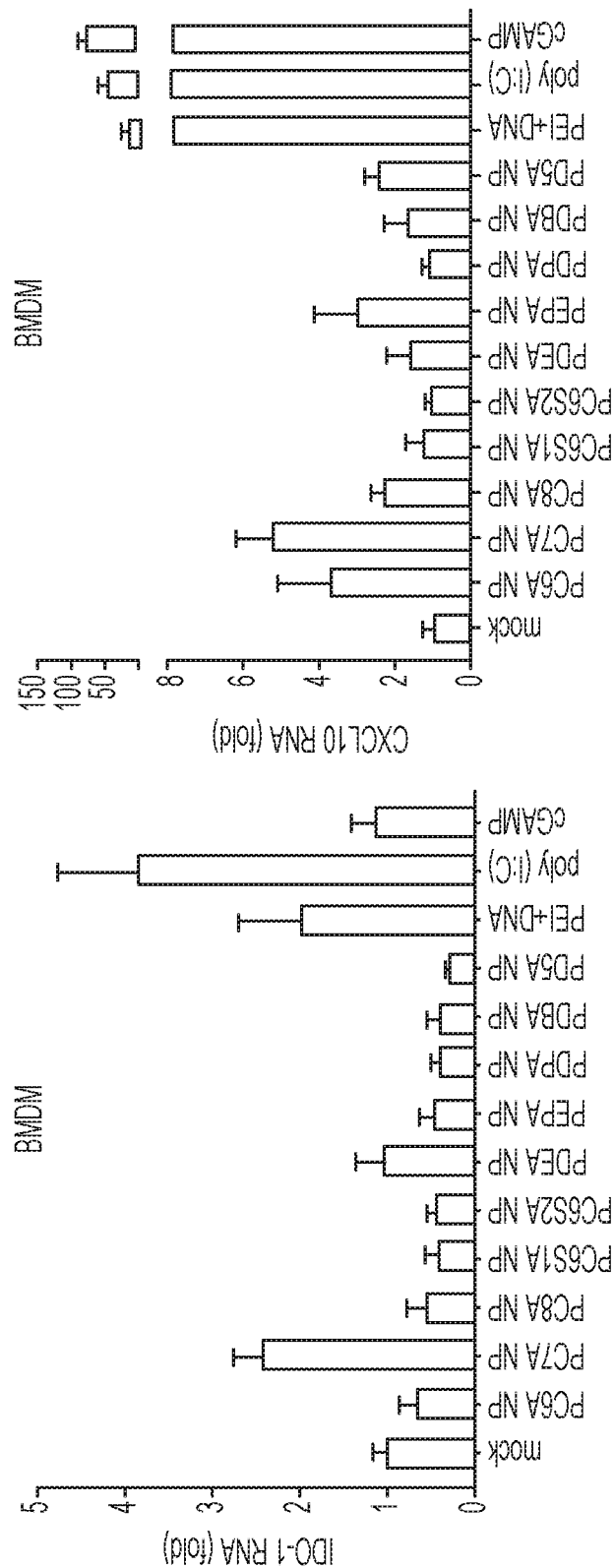

STING-type I IFN activation has been reported to induce immune regulatory responses, where IDO-1 expression was identified as a major immune checkpoint in this regulatory pathway (Lemos et al., 2014; Huang et al., 2012). In this study, the inventors first performed the in vivo IDO enzyme activity assay in mice treated with different polymers. Mice treated with subcutaneous injections of PC7A, PD5A or PEPA copolymers (150 μg, 5-fold of vaccine dose) showed 33-51% increase in IDO activity in spleen over the PBS control, which is less than the positive control of intravenously injected PEI-DNA. No statistically significant differences were detected among the IDO activities induced by PC7A, PD5A or PEPA copolymer (FIG. 9H). The in vivo animal data was further supported by cell culture data in THP-1 and BMDM cells. In this study, the inventors compared the IDO-1 and CXCL10 expression profiles treated with the whole panel of nanoparticles. Results show that the lack of CTL activity by nanoparticles other than PC7A NP are not a result of elevated IDO-1 expression but rather due to the lack of STING activation (FIGS. 9I-J) and inefficient antigen delivery and presentation on DCs (e.g., see representative data of PD5A in FIG. 2D).

Figure 13:
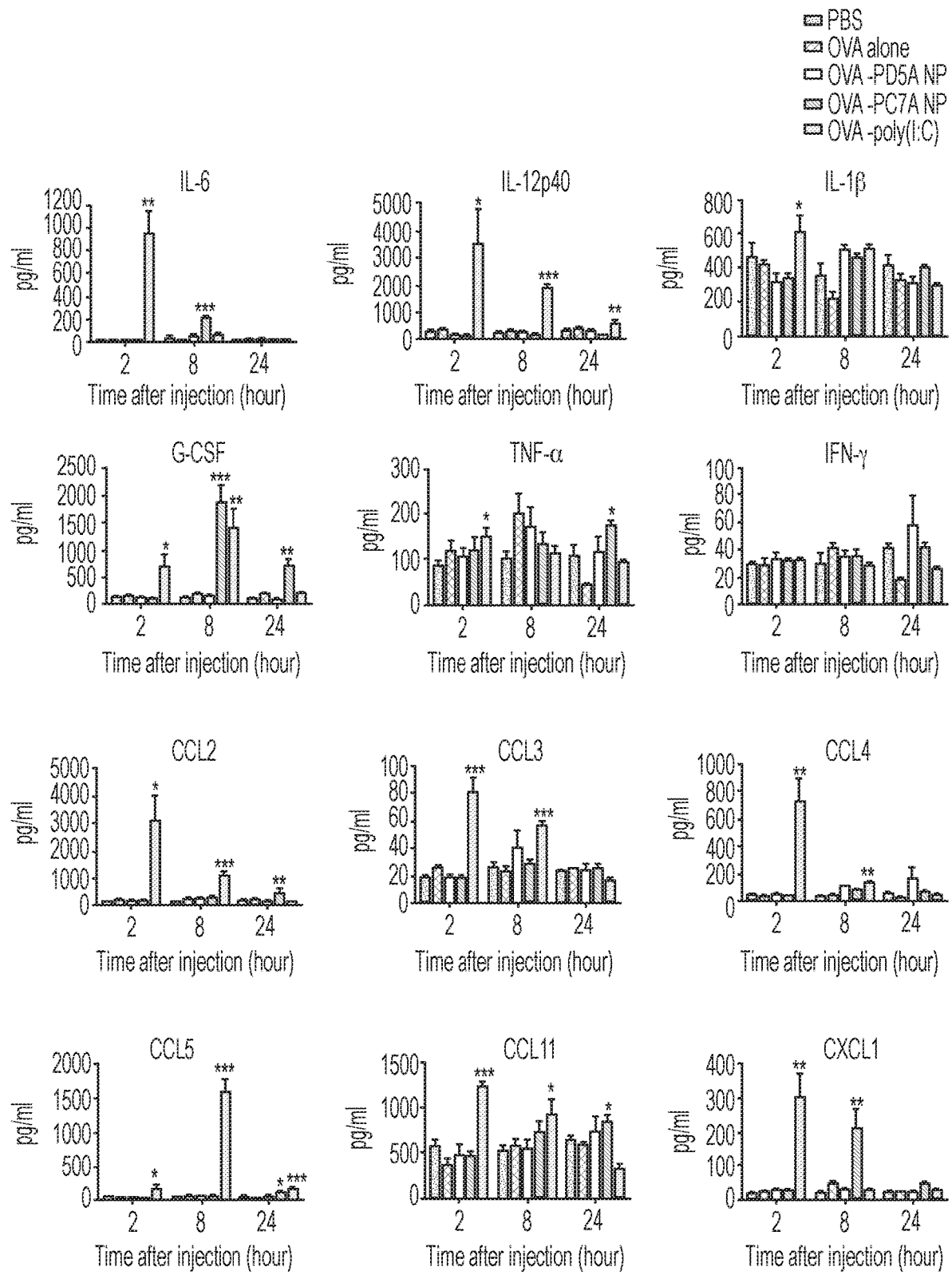
FIG. 13. PC7A nanovaccine showed less systemic cytokine levels compared to Poly(I:C) control. C57BL/6 mice (n=5 per group) were subcutaneously injected with 10 μg OVA plus 150 μg PC7A NP or the same dose of Poly(I:C). Systemic cytokines and chemokines in the serum were measured over time by bead-based Bio-Plex Pro Mouse Cytokine 23-plex Assay. IL-1α, IL-2, IL-3, IL-4, IL-5, IL-9, IL-10, IL-12 (p70), IL-13, IL-17, GM-CSF did not show any significant difference in all groups and were not included in this figure. Data are presented as means±s.e.m. Statistical significance was calculated by Student's t-test, *P<0.001, P<0.01, *P<0.05.
Figure 14:
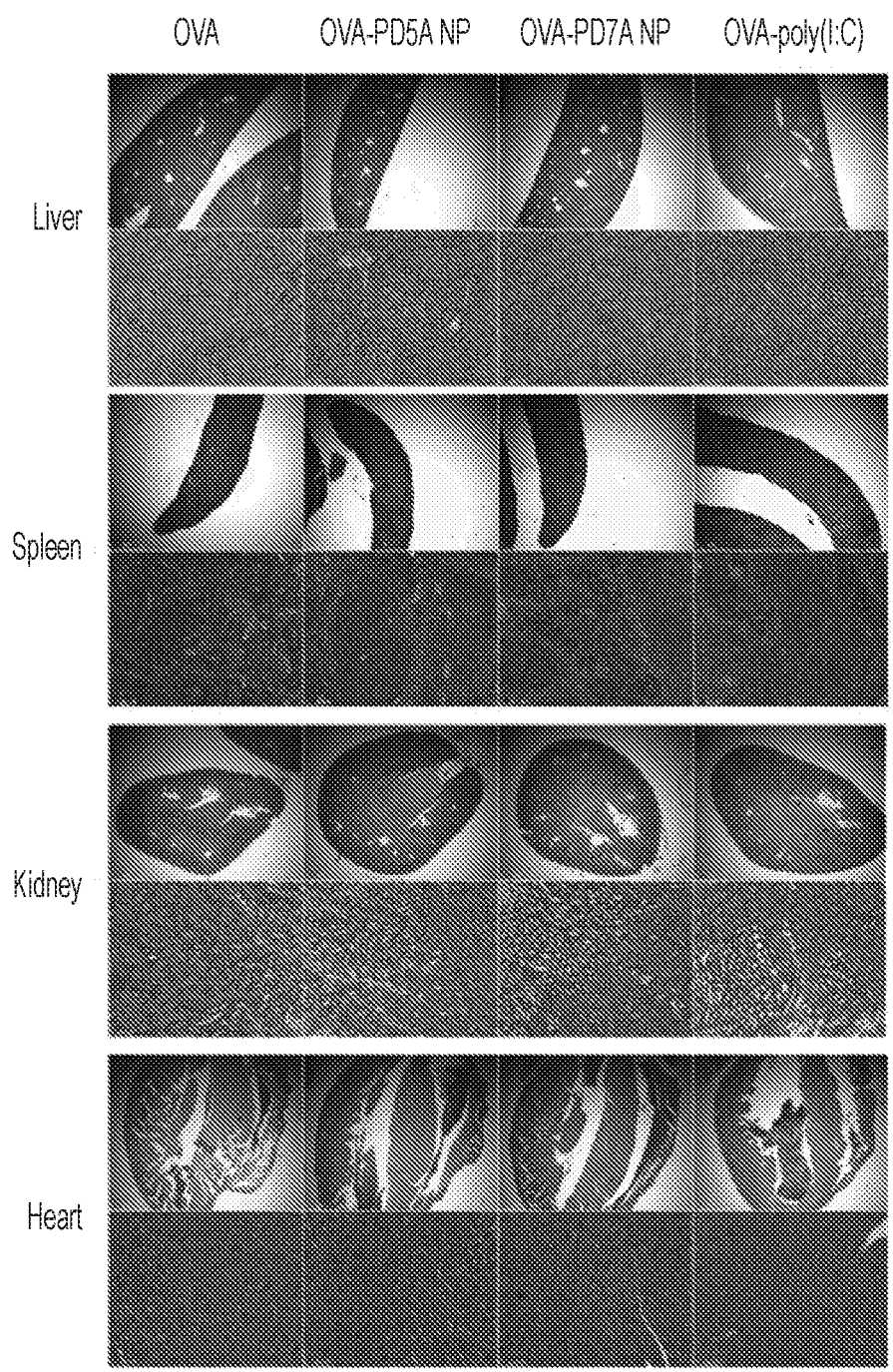
FIG. 14. Histology analyses of major organs for safety assessment of PC7A nanovaccine. Representative H&E sections of the main organs from C57BL/6 mice after repeated injections of 10 μg OVA plus 150 μg PC7A NP or the same dose of Poly(I:C). Mice were sacrificed 24 h after the second injection (n=5 for each group). Liver in Poly(I:C) group showed ballooned hepatocytes indicative of steatohepatitis. Spleen, kidney and heart showed no abnormalities for all the groups.
Figure 15:
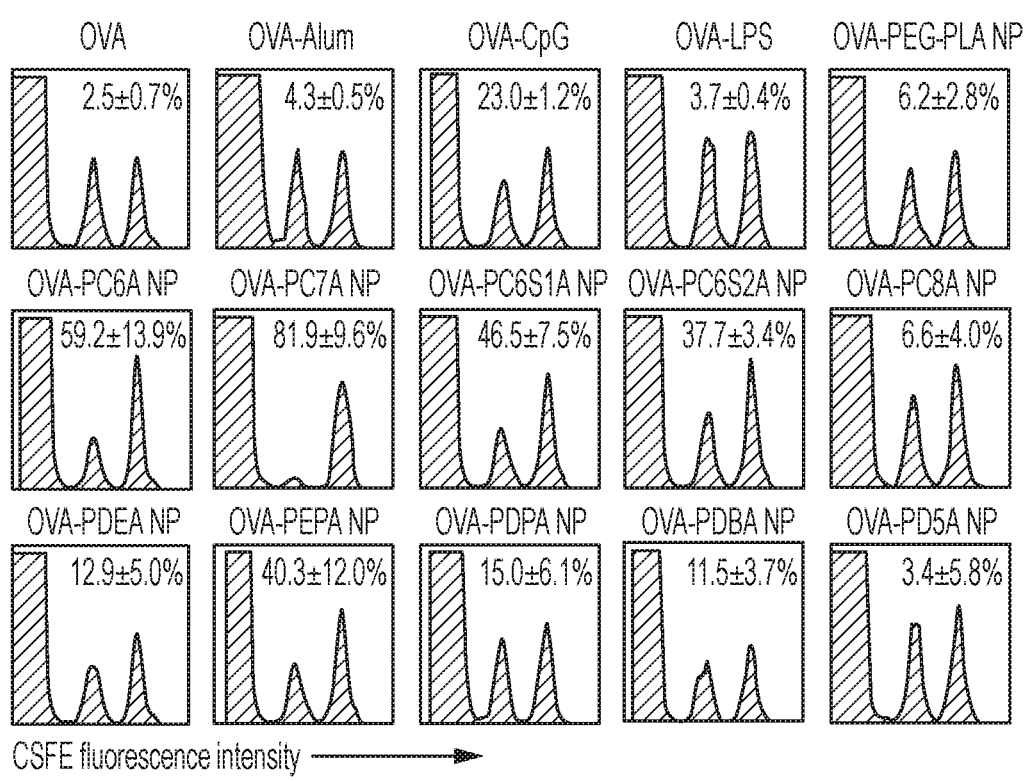
FIG. 15. Comparison of OVA-specific CTL responses in different NP groups by in vivo cytotoxicity killing assay. The blood samples of immunized mice after injection of a 1:1 mixture of $CFSE^{high}$ and $CFSE^{low}$-labeled splenocytes that had been unpulsed or pulsed with $OVA_{257-264}$ peptides, respectively, were analyzed by flow cytometry to determine the percentages of the $CFSE^{high}$ and $CFSE^{low}$ cells. Representative flow cytometric plots from three independent experiments for each group. The value in each panel represents the mean percentage of specific lysis in the blood±s.e.m.
Figure 16A:
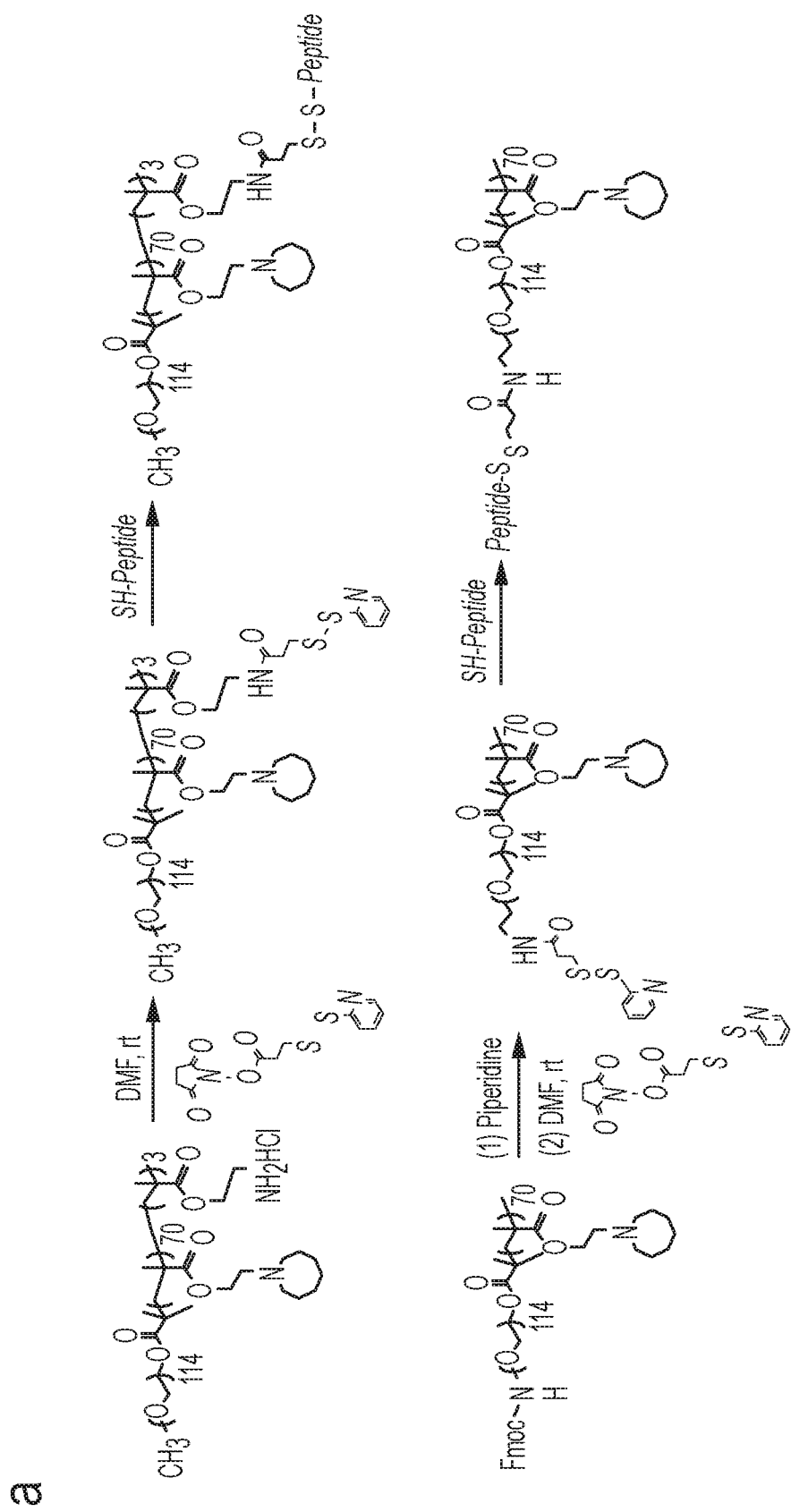

Based on the above characteristics (FIG. 4A), the inventors investigated the antitumor efficacy of PC7A nanovaccine in several tumor models. In the B16-OVA melanoma model, a physical mixture of antigenic peptides (OVA$_{257-280}$, 0.5 μg) with PC7A NP (30 μg) was formulated. Different nanovaccine groups were subcutaneously injected 5 days after tumor inoculation, followed by a booster shot 5 days later (FIG. 4B). In the PBS control group, all the animals died in 20 days. OVA$_{257-280}$ alone, PC7A NP alone or OVA$_{257-280}$-PD5A NP groups did not offer any significant tumor growth inhibition or survival benefit over the PBS control (FIGS. 11A-B). OVA$_{257-280}$-CpG and OVA$_{257-280}$-Poly(I:C) groups offered a minor degree of immune protection (FIGS. 4B-C). Still, all the animals died before day 40. In contrast, OVA$_{257-280}$-PC7A NP achieved the maximum therapeutic efficacy, where 50% of animals survived over 40 days. In B16-F10 melanoma, the inventors used a cocktail of either tumor associated antigens (Gp100$_{21-41}$, Trp1$_{214-237}$, Trp2$_{173-196}$) or neoantigens (Obsl1$_{T1764M}$, Kif18b$_{K739N}$, Def8$_{R255G}$) (Kreiter et al., 2015) in PC7A NP (0.5 μg for each peptide, 30 μg polymer). PC7A vaccination significantly slowed the growth of B16F10 tumors over antigen only, PC7A only and non-treated controls (P<0.001 in both studies, n=10, FIG. 4d and FIG. 11C). In the colon cancer MC38 model, they selected three tumor neoantigens (Reps1$_{P45A}$, Adpgk$_{R304M}$, Dpagt1$_{V213L}$) with validated immunogenic neo-epitopes (Yadav et al., 2014). Data also show significantly improved tumor growth inhibition (FIG. 4E). Finally, the inventors employed human papilloma virus (HPV) E6/7 TC-1 tumors (Sun et al., 2015; Liu et al., 2016). Using an E7-derived peptide E7$_{43-62}$, 50% of mice are tumor free over 60 days when treated with E7$_{43-62}$-PC7A NP (FIGS. 4F-G and FIG. 12E). Combination of PC7A nanovaccine with an anti-PD-1 antibody showed synergy in both B16-OVA melanoma and TC-1 tumor models (FIG. 4G and FIGS. 12A-F). In the TC-1 model, 100% of the animals survived for more than 60 days and 90% of these animals were tumor free (FIG. 12E). Both B16OVA and TC-1 tumor models showed mild PD-L1 expressions on tumor cells while certain subtype of myeloid cells had high PD-L1 expressions over the isotype control (FIGS. 12D and 12F). These data support the nanovaccine synergy with anti-PD1 therapy. Meanwhile, anti-PD-1 therapy alone did not lead to significantly improved antitumor effect in either model, as also reported by other groups (Rice et al., 2015; Holmgaard et al., 2013). Tumor-free mice were rechallenged with $1 \times 10^6$ TC-1 tumor cells 82 days after tumor inoculation. Data showed that the previously treated, tumor-free mice were resistant to the newly transplanted tumors for over 60 days whereas such tumors grew robustly in naïve mice and surgically cured mice (FIG. 12E). These results suggest a long-term antitumor response induced by the nanovaccine, which likely activate memory T cells. Analyses of systemic cytokines/chemokines of mice treated with PC7A NP (150 µg, 5-fold of vaccine dose) showed much less systemic inflammation compared to Poly(I:C) control (FIG. 13). Histology analysis of major organs (e.g., liver, spleen, kidney, heart) did not show any observable toxicity in the mice treated with repeated injections of PC7A nanovaccine (150 µg, 5-fold of vaccine dose, FIG. 14). These data demonstrate the safe and efficacious antitumor immunity of PC7A nanovaccine at a small antigen dose (0.5 µg), and its notable synergy with a checkpoint inhibitor.

Results from this study established a simple nanoparticle, PC7A NP, which can be physically mixed with a wide range of tumor antigens to produce a robust cancer-specific T cell response. Our original attempt was to screen a library of ultra-pH sensitive polymer compositions that would allow T cell immunity against tumors. In PC7A NP, the inventors serendipitously discovered a single polymer composition that meets all the spatio-temporal criteria for T cell activation. Mechanistically, PC7A NP allowed stable antigen loading within a small size confinement (<50 nm) that facilitates antigen delivery to the lymph nodes. Equally important, PC7A NP achieved efficient cytosolic delivery of tumor antigens and STING activation. The 7-membered cyclic amine side chain structure in PC7A NP rendered a relatively high transition pH (i.e., 6.9) providing pH-specific proton sponge effect at early endosomal pH (6.5-7.0) and rigid configuration of protonated unimers for membrane disruption (FIGS. 8A-B). A conventional pH-insensitive nanoparticle, PEG-b-PLA micelles, was also included in the CTL screen but did not show any observable CTL effect (FIG. 1B). Early endosomal release of tumor antigens into the cytosol avoids lysosomal degradation leading to increased antigen cross-presentation on the cell surface. This unique membrane disruption capability may also be responsible for introducing trace amount of DNA into cytosol, which subsequently activates cytosolic cGAS-STING pathway for innate stimulation[21]. Meanwhile, STING pulldown assay and ITC experiment uncovered direct binding of PC7A to STING. The PC7A-STING interaction appeared to be specific, as supported by the lack of STING CTD pulldown by PEPA and PD5A copolymers (particularly, PEPA has the same transition pH as PC7A but lacks the ring structure), as well as negligible binding between PC7A and BSA by the ITC experiment.

In summary, the inventors' discovery that a synthetic nanoparticle not only enhances antigen delivery but also stimulates the STING pathway to boost antitumor immunity offers a new approach in cancer immunotherapy. The simplicity, robust T cell response and synergy with checkpoint inhibition make the PC7A nanovaccine an attractive candidate for clinical development. This nanovaccine platform can be rapidly adopted to incorporate many existing tumor-associated antigens as well as a growing number of tumor neoantigens (Schumacher & Schreiber, 2015; Sharma & Allison, 2015). The unique characteristics of PC7A NP also allows it to package microbial antigens as vaccines for the prevention and treatment of infectious diseases.

Example 3

Combination of Nanovaccine and Radiation Therapy $2 \times 10^5$ TC-1 cells were injected subcutaneously on the back of C57BL/6 mice (n=8/group). Tumors were radiated at 20 Gy 14 days later when they reached the size of ~200 mm$^3$. For vaccination treatments, on the same day of ionizing radiation, the nanovaccine (30 µg PC7A+0.5 µg peptide E7$_{43-62}$ (GQAEPDRAHYNIVTFCCKCD, SEQ ID NO: 26) was injected subcutaneously onto the back of mice at the tail base. Six days later, mice were boosted with another injection of nanovaccine with the same dose. Tumor growth was subsequently measured twice a week using a digital caliper and calculated as 0.5×length×width$^2$ by blinded investigators. Mice were sacrificed when tumor size reached 1500 mm$^3$. As can be seen in FIG. 18, the combined nanovaccine and radiation therapy showed significantly improved therapeutic synergy over treatment with either radiation or the nanovaccine alone.

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Abbas et al., *Cellular and Molecular Immunology.* 8th edn, 2014.
Alexopoulou et al., *Nature,* 413:732-738, 2001.
Azuma et al., *Cell Immunol.,* 116(1):123-134, 1988.
Baccala et al., *Nat Med,* 13:543-551, 2007.
Barber et al., *J Immunol,* 171:27-31, 2003.
Benjamini et al., *Adv. Exp. Med. Biol.,* 303:71-77, 1991.
Bisht et al., *Indian J. Cancer,* 47(4):443-451, 2010.
Boussif et al., *Proc Natl Acad Sci USA,* 92:7297-7301, 1995.
Carvalho, et al., *Scan. J. Immunol.,* 56:327, 2002.
Chen and Mellman, *Immunity,* 39:1-10, 2013.

Collins et al., *Cell Host Microbe*, 17:820-828, 2015.
De Taeye, et al., *Trends Immunol.*, pii:S1471, 2016.
Fuertes et al., *Trends Immunol*, 34:67-73, 2013.
Gupta and Kanodia, *Natl. Med. J. India*, 15(4):202-207, 2002.
Heath et al., *Immunol Rev*, 199:9-26, 2004.
Hemmi et al., *Nature*, 408:740-745, 2000.
Hildner et al., *Science*, 322:1097-1100, 2008.
Hubbell et al., *Nature*, 462:449-460, 2009.
Husson et al., *J. Bacteriol.*, 172(2):519-524, 1990.
Jacobs et al., *Nature*, 327(6122):532-535, 1987.
Li et al., *Science*, 341:1390-1394, 2013.
Liechtenstein et al., *Immunol Endocr Metab Agents Med Chem*, 12:224-235, 2012.
Liu et al., *Nature*, 507:519-522, 2014.
Lotte et al., *Adv. Tuberc. Res.*, 21:107-93; 194-245, 1984.
Luelmo, *Am. Rev. Respir. Dis.*, 125(3 Pt 2):70-72, 1982.
Ma et al., *J Am Chem Soc*, 136:11085-11092, 2014.
Maldonado et al., *Proc Natl Acad Sci USA*, 112:E156-165, 2015.
Martin et al., *Nature*, 345(6277):739-743, 1990.
Ottenhoff and Kaufmann, *PLoS Pathogen*, 8:e1002607, 2012.
PCT Patent Application WO 91/16347
Poltorak et al., *Science*, 282:2085-2088, 1998.
Rabinovich et al., *Science*, 265(5177):1401-1404, 1994.
Reddy et al., *Nat Biotechnol*, 25:1159-1164, 2007.
Remington's Pharmaceutical Sciences, 15$^{th}$ ed., pages 1035-1038 and 1570-1580, Mack Publishing Company, Easton, Pa., 1980.
Rosenberg and Restifo, *Science*, 348:62-68, 2015.
Sancho et al., *J Clin Invest*, 118:2098-2110, 2008.
Schumacher and Schreiber, *Science*, 348:69-74, 2015.
Snapper et al., *Proc. Natl. Acad. Sci. USA*, 85(18):6987-6991, 1988.
Sun et al., *Clin Cancer Res*, 2015.
Sun et al., *Science*, 339:786-791, 2013.
Takada et al., *J. Clin. Microbiol.*, 33(3):658-660, 1995.
Topalian et al., *N Engl J Med*, 366:2443-2454, 2012.
Trinchieri, *J Exp Med*, 207:2053-2063, 2010.
Tsarevsky and Matyjaszewski, *Chem Rev*, 107:2270-2299, 2007.
Tumeh et al., *Nature*, 515:568-571, 2014.
U.S. Pat. No. 4,435,386
U.S. Pat. No. 4,436,728
U.S. Pat. No. 4,505,900
U.S. Pat. No. 4,866,034
U.S. Pat. No. 4,877,611
U.S. Pat. No. 4,950,645
U.S. Pat. No. 5,399,363
U.S. Pat. No. 5,466,468
U.S. Pat. No. 5,543,158
U.S. Pat. No. 5,641,515
U.S. Pat. No. 5,846,233
U.S. Pat. No. 5,980,912
U.S. Pat. No. 4,436,727
U.S. Pat. No. 4,505,899
U.S. Pat. No. 4,520,019
U.S. Pat. No. 4,579,945
Wang et al., *Nat Commun*, 6:8524, 2015.
Wilson et al., *ACS Nano*, 7:3912-3925, 2013.
Wilson et al., *ACS Nano*, 7:3912-3925, 2013.
Woo et al., *Trends Immunol*, 36:250-256, 2015.
Yamamoto et al., *Jpn. J. Cancer Res.*, 79:866-873, 1988.
Yin et al., *J. Biol. Resp. Modif.*, 8:190-205, 1989.
Zhou et al., *Angew Chem Int Ed Engl*, 50:6109-6114, 2011.
Zhou et al., *J Am Chem Soc*, 134:7803-7811, 2012.
Zitvogel et al., *Nat Rev Immunol*, 15:405-414, 2015.
Zhou et al., *Angewandte Chemie* 2011, 50, 6109-14.
Zhou et al., *Journal of the American Chemical Society* 2012, 134, 7803-11.
Tsarevsky and Matyjaszewski, *Chemical Reviews* 2007, 107, 2270-99.
Li et al., *Science* 2013, 341, 1390-4.
Collins et al., *Cell Host & Microbe* 2015, 17, 820-8.
Wilson et al., *ACS Nano* 2013, 7, 3912-25.
Zhang et al., *Molecular Cell* 2013, 51, 226-35.
Huang et al., *Journal of Immunology* 2012, 188, 4913-20.
Hoshi et al., *Journal of Immunology* 2010, 185, 3305-12.
Lizotte et al., *Nat Nanotechnol* 11, 295-303 (2016).
Reddy et al., *Nat Biotechnol* 25, 1159-1164 (2007).
Liu et al., *Nature* 507, 519-522 (2014).
Ma et al., *J Am Chem Soc* 136, 11085-11092 (2014).
Wang et al., *Nat Commun* 6, 8524 (2015).
Boussif et al., *Proc Natl Acad Sci USA* 92, 7297-7301 (1995).
Barber et al., *J Immunol* 171, 27-31 (2003).
Maldonado et al., *Proc Natl Acad Sci USA* 112, E156-165 (2015).
Poltorak et al., *Science* 282, 2085-2088 (1998).
Hemmi et al., *Nature* 408, 740-745 (2000).
Hildner et al., *Science* 322, 1097-1100 (2008).
Sancho et al., *J Clin Invest* 118, 2098-2110 (2008).
Heath et al., *Immunol Rev* 199, 9-26 (2004).
Wilson et al., *ACS Nano* 7, 3912-3925 (2013).
Liechtenstein et al., *Immunol Endocr Metab Agents Med Chem* 12, 224-235 (2012).
Zitvogel et al., *Nat Rev Immunol* 15, 405-414 (2015).
Fuertes et al., *Trends Immunol* 34, 67-73 (2013).
Trinchieri, G. *J Exp Med* 207, 2053-2063 (2010).
Alexopoulou et al., *Nature* 413, 732-738 (2001).
Baccala et al., *Nat Med* 13, 543-551 (2007).
Sun et al., *Science* 339, 786-791 (2013).
Carroll et al., *Immunity* 44, 597-608 (2016).
Woo et al., *Immunity* 41, 830-842 (2014).
Lemos et al., *Eur J Immunol* 44, 2847-2853 (2014).
Huang et al., *J Immunol* 188, 4913-4920 (2012).
Kreiter et al., *Nature* 520, 692-696 (2015).
Yadav et al., *Nature* 515, 572-576 (2014).
Sun et al., *Clin Cancer Res* (2015).
Liu et al., *Oncoimmunology* 5, e1147641 (2016).
Rice et al., *Cancer Gene Ther* 22, 454-462 (2015).
Holmgaard et al., *J Exp Med* 210, 1389-1402 (2013).
Schumacher & Schreiber, *Science* 348, 69-74 (2015).
Sharma & Allison, *Cell* 161, 205-214 (2015).

What is claimed is:

1. A composition comprising:

(A) a protein or peptide antigen;

(B) a pH sensitive diblock copolymer nanoparticle, wherein the diblock copolymer is of the formula:

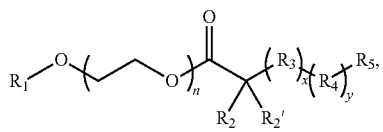

(Formula I)

wherein: $R_1$ is hydrogen, alkyl$_{(C<12)}$, cycloalkyl$_{(C<12)}$, substituted alkyl$_{(C<12)}$, or substituted cycloalkyl$_{(C<12)}$;

n is an integer from 1 to 500;

$R_2$ and $R_2'$ are each independently selected from the group consisting of hydrogen, alkyl$_{(C<12)}$, cycloalkyl$_{(C<12)}$, substituted alkyl$_{(C<12)}$, and substituted cycloalkyl$_{(C<12)}$;

$R_3$ is a group of the formula:

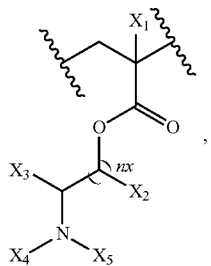

(Formula II)

wherein:

$n_x$ is 1-10;

$X_1$, $X_2$, and $X_3$ are each independently selected from hydrogen, alkyl$_{(C<12)}$, cycloalkyl$_{(C<12)}$, substituted alkyl$_{(C<12)}$, and substituted cycloalkyl$_{(C<12)}$;

$X_4$ and $X_5$ are taken together and are —CH$_2$CH$_2$CH$_2$CH$_2$CH$_2$—, —CH$_2$CH$_2$CH$_2$CH$_2$CH$_2$CH$_2$—, —CH$_2$CH$_2$CH(CH$_3$)CH$_2$CH$_2$—, or —CH$_2$CH(CH$_3$)CH$_2$CH(CH$_3$)CH$_2$—;

x is an integer from 1 to 150;

$R_4$ is a group of the formula:

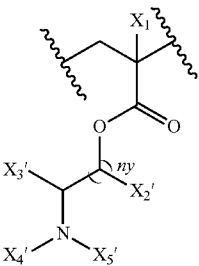

(Formula III)

wherein:

$n_y$ is 1-10;

$X_1'$, $X_2'$, and $X_3'$ are each independently selected from hydrogen, alkyl$_{(C<12)}$, cycloalkyl$_{(C<12)}$, substituted alkyl$_{(C<12)}$, and substituted cycloalkyl$_{(C<12)}$;

$X_4'$ is a dye or a fluorescence quencher;

$X_5'$ is selected from hydrogen, alkyl$_{(C<12)}$, cycloalkyl$_{(C<12)}$, substituted alkyl$_{(C<12)}$, substituted cycloalkyl$_{(C<12)}$, substituted acyl$_{(C<12)}$, a dye, and a fluorescence quencher;

y is an integer from 0 to 150; and $R_5$ is hydrogen, halo, hydroxy, alkyl$_{(C<12)}$, or substituted alkyl$_{(C<12)}$;

$R_3$ and $R_4$ can occur in any order within the diblock copolymer; and wherein the antigen is encapsulated by the diblock copolymer.

2. The composition of claim 1, wherein the antigen is an anti-cancer antigen.

3. The composition of claim 2, wherein the antigen is a tumor-associated antigen or a tumor neoantigen.

4. The composition of claim 3, wherein the tumor-associated antigen is human papilloma virus E6 protein, E7 protein, or a fragment thereof.

5. The composition of claim 3, wherein the tumor-associated antigen is mesothelin or a fragment thereof.

6. The composition of claim 2, wherein the anti-cancer antigen is a melanoma tumor-associated antigen or neoantigen.

7. The composition of claim 2, wherein the anti-cancer antigen is a bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid cancer antigen.

8. The composition of claim 1, wherein the antigen is a viral antigen.

9. The composition of claim 8, wherein the viral antigen is a hepatitis B virus antigen, an influenza virus antigen, a West Nile virus antigen, a Dengue virus antigen, an Ebola virus antigen, or a HIV antigen.

10. The composition of claim 1, wherein the antigen is a bacterial antigen.

11. The composition of claim 10, wherein the antigen is a *Mycobacterium tuberculosis* (Mtb) antigen.

12. The composition of claim 1, wherein the antigen is a malaria antigen.

13. The composition according to claim 1, wherein the diblock copolymer has a $pK_a$ in water from about 6 to about 7.5 as calculated by pH titration.

14. The composition according to claim 1, wherein a nanoparticle of the diblock copolymer dissociates at a pH below the pKa.

15. The composition of claim 1,
wherein the composition is a nanoparticle comprising a particle size of less than 50 nm.

16. A pharmaceutical composition comprising:
(A) a composition according to claim 1; and
(B) an excipient.

17. The composition of claim 1, wherein n is from 50 to 200.

18. The composition of claim 1, wherein x is from 50 to 120 and y is 0.

19. The composition of claim 1, wherein the diblock copolymer comprises $PEG_{114}$-b-$PC6A_{70}$, $PEG_{114}$-b-$PC_7A_{70}$, $PEG_{114}$-b-$PC_6S1A_{70}$, or $PEG_{114}$-b-$PC6S2A_{70}$.

20. The composition of claim 1, wherein $X_1$ is a methyl group.

21. The composition of claim 20, wherein y is zero.

22. A method of vaccinating against an infectious disease comprising administering to a patient an effective amount of the composition of claim 1, wherein, upon vaccination, the patient may generate an immune response against the infectious disease antigen.

23. A method of treating cancer in a patient in need thereof comprising administering to the patient a therapeutically effective amount of the composition according to claim 2.

* * * * *

SEQUENCE LISTING

<160> NUMBER OF SEQ ID NOS: 33

<210> SEQ ID NO 1
<211> LENGTH: 31
<212> TYPE: PRT

<213> ORGANISM: Artificial sequence
<220> FEATURE:
<223> OTHER INFORMATION: Synthetic polypeptide

<400> SEQUENCE: 1

```
Leu His Glu Tyr Met Leu Asp Leu Gln Pro Glu Thr Val Asp Leu Asp
1               5                   10                  15
Leu Leu Met Gly Thr Leu Gly Ile Val Cys Pro Ile Cys Ser Gln
            20                  25                  30
```

<210> SEQ ID NO 2
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 2

```
Asp Thr Pro Thr Leu His Glu Tyr Met Leu Asp Leu Gln Pro Glu Thr
1               5                   10                  15
Val Asp Leu Tyr Cys Tyr Glu
            20
```

<210> SEQ ID NO 3
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 3

```
Gly Gln Lys Met Asn Ala Gln Ala Ile Ala Leu Val Ala Cys Tyr Leu
1               5                   10                  15
Arg Gly Gly Gly Gln Leu Asp Glu Asp Met Val
            20                  25
```

<210> SEQ ID NO 4
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 4

```
His Ala Ser Ser Thr Phe Thr Ile Thr Asp Gln Val Pro Phe Ser Val
1               5                   10                  15
Ser Val Ser Gln Leu Gln Ala Leu
            20
```

<210> SEQ ID NO 5
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 5

```
Ser His Glu Gly Pro Ala Phe Leu Thr Trp His Arg Tyr His Leu Leu
1               5                   10                  15
Gln Leu Glu Arg Asp Met Gln Glu
            20
```

<210> SEQ ID NO 6
<211> LENGTH: 24

```
<212> TYPE: PRT
<213> ORGANISM: Artificial sequence
<220> FEATURE:
<223> OTHER INFORMATION: Synthetic polypeptide

<400> SEQUENCE: 6

Gln Pro Gln Ile Ala Asn Cys Ser Val Tyr Asp Phe Phe Val Trp Leu
1               5                   10                  15

His Tyr Tyr Ser Val Arg Asp Thr
            20

<210> SEQ ID NO 7
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 7

Arg Glu Gly Val Glu Leu Cys Pro Gly Asn Lys Tyr Glu Met Arg Arg
1               5                   10                  15

His Gly Thr Thr His Ser Leu Val Ile His Asp
            20                  25

<210> SEQ ID NO 8
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 8

Asp Ser Gly Ser Pro Phe Pro Ala Ala Val Ile Leu Arg Asp Ala Leu
1               5                   10                  15

His Met Ala Arg Gly Leu Lys Tyr Leu His Gln
            20                  25

<210> SEQ ID NO 9
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 9

Val Val Asp Arg Asn Pro Gln Phe Leu Asp Pro Val Leu Ala Tyr Leu
1               5                   10                  15

Met Lys Gly Leu Cys Glu Lys Pro Leu Ala Ser
            20                  25

<210> SEQ ID NO 10
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 10

Pro Ser Lys Pro Ser Phe Gln Glu Phe Val Asp Trp Glu Asn Val Ser
1               5                   10                  15

Pro Glu Leu Asn Ser Thr Asp Gln Pro Phe Leu
            20                  25

<210> SEQ ID NO 11
```

```
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 11

Asn His Ser Gly Leu Val Thr Phe Gln Ala Phe Ile Asp Val Met Ser
1               5                   10                  15

Arg Glu Thr Thr Asp Thr Asp Thr Ala Asp Gln
            20                  25

<210> SEQ ID NO 12
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 12

Ser Ile Ile Asn Phe Glu Lys Leu Thr Glu Trp Thr Ser Ser Asn Val
1               5                   10                  15

Met Glu Glu Arg Lys Ile Lys Val
            20

<210> SEQ ID NO 13
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 13

Gly Gln Ala Glu Pro Asp Arg Ala His Tyr Asn Ile Val Thr Phe Cys
1               5                   10                  15

Cys Lys Cys Asp
            20

<210> SEQ ID NO 14
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 14

Arg Ala His Tyr Asn Ile Val Thr Phe
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 15

Ser Ile Ile Asn Phe Glu Lys Leu
1               5

<210> SEQ ID NO 16
<211> LENGTH: 25
<212> TYPE: DNA
<213> ORGANISM: Artificial sequence
<220> FEATURE:
<223> OTHER INFORMATION: Synthetic primer
```

<400> SEQUENCE: 16
atgcacagat cttcaaggcc tgggc                                    25

<210> SEQ ID NO 17
<211> LENGTH: 25
<212> TYPE: DNA
<213> ORGANISM: Artificial sequence
<220> FEATURE:
<223> OTHER INFORMATION: Synthetic primer

<400> SEQUENCE: 17
gtgctgtgga gtgcacagcg gaagt                                    25

<210> SEQ ID NO 18
<211> LENGTH: 19
<212> TYPE: DNA
<213> ORGANISM: Artificial sequence
<220> FEATURE:
<223> OTHER INFORMATION: Synthetic primer

<400> SEQUENCE: 18
gccgtcattt tctgcctca                                           19

<210> SEQ ID NO 19
<211> LENGTH: 19
<212> TYPE: DNA
<213> ORGANISM: Artificial sequence
<220> FEATURE:
<223> OTHER INFORMATION: Synthetic primer

<400> SEQUENCE: 19
cgtccttgcg agagggatc                                           19

<210> SEQ ID NO 20
<211> LENGTH: 19
<212> TYPE: DNA
<213> ORGANISM: Artificial sequence
<220> FEATURE:
<223> OTHER INFORMATION: Synthetic primer

<400> SEQUENCE: 20
aaatcgccaa tgccaactc                                           19

<210> SEQ ID NO 21
<211> LENGTH: 20
<212> TYPE: DNA
<213> ORGANISM: Artificial sequence
<220> FEATURE:
<223> OTHER INFORMATION: Synthetic primer

<400> SEQUENCE: 21
tcttccctat gcccatatgc                                          20

<210> SEQ ID NO 22
<211> LENGTH: 20
<212> TYPE: DNA
<213> ORGANISM: Artificial sequence
<220> FEATURE:
<223> OTHER INFORMATION: Synthetic primer

<400> SEQUENCE: 22
tggcattcaa ggagtacctc                                          20

<210> SEQ ID NO 23

```
<211> LENGTH: 22
<212> TYPE: DNA
<213> ORGANISM: Artificial sequence
<220> FEATURE:
<223> OTHER INFORMATION: Synthetic primer

<400> SEQUENCE: 23
ttgtagcaat gatctcaaca cg                                          22

<210> SEQ ID NO 24
<211> LENGTH: 20
<212> TYPE: DNA
<213> ORGANISM: Artificial sequence
<220> FEATURE:
<223> OTHER INFORMATION: Synthetic primer

<400> SEQUENCE: 24
atgacatcaa gaaggtggtg                                             20

<210> SEQ ID NO 25
<211> LENGTH: 20
<212> TYPE: DNA
<213> ORGANISM: Artificial sequence
<220> FEATURE:
<223> OTHER INFORMATION: Synthetic primer

<400> SEQUENCE: 25
cataccagga aatgagcttg                                             20

<210> SEQ ID NO 26
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 26

Gly Gln Ala Glu Pro Asp Arg Ala His Tyr Asn Ile Val Thr Phe Cys
1               5                   10                  15

Cys Lys Cys Asp
            20

<210> SEQ ID NO 27
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 27

Ser Ile Ile Asn Phe Glu Lys Leu Thr Glu Trp Thr Ser Ser Asn Val
1               5                   10                  15

Met Glu Glu Arg Lys Ile Lys Val
            20

<210> SEQ ID NO 28
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 28

Arg Ala His Tyr Asn Ile Val Thr Phe
1               5
```

```
<210> SEQ ID NO 29
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 29

Val Gly Ala Leu Glu Gly Ser Arg Asn Gln Asp Trp Leu Gly Val Pro
1               5                   10                  15

Arg Gln Leu Val Thr
            20

<210> SEQ ID NO 30
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 30

Ser His Cys His Trp Asn Asp Leu Ala Val Ile Pro Ala Gly Val Val
1               5                   10                  15

His Asn Trp Asp Phe Glu Pro Arg Lys Val Ser
            20                  25

<210> SEQ ID NO 31
<211> LENGTH: 28
<212> TYPE: PRT
<213> ORGANISM: Artificial sequence
<220> FEATURE:
<223> OTHER INFORMATION: Synthetic polypeptide

<400> SEQUENCE: 31

Gly Arg Val Leu Glu Leu Phe Arg Ala Ala Gln Leu Ala Asn Asp Val
1               5                   10                  15

Val Leu Gln Ile Met Glu Leu Cys Gly Ala Thr Arg
            20                  25

<210> SEQ ID NO 32
<211> LENGTH: 28
<212> TYPE: PRT
<213> ORGANISM: Artificial sequence
<220> FEATURE:
<223> OTHER INFORMATION: Synthetic polypeptide

<400> SEQUENCE: 32

Gly Ile Pro Val His Leu Glu Leu Ala Ser Met Thr Asn Met Glu Leu
1               5                   10                  15

Met Ser Ser Ile Val His Gln Gln Val Phe Pro Thr
            20                  25

<210> SEQ ID NO 33
<211> LENGTH: 25
<212> TYPE: PRT
<213> ORGANISM: Artificial sequence
<220> FEATURE:
```

<223> OTHER INFORMATION: Synthetic polypeptide

<400> SEQUENCE: 33

Glu Ala Gly Gln Ser Leu Val Ile Ser Ala Ser Ile Ile Val Phe Asn
1               5                   10                  15

Leu Leu Glu Leu Glu Gly Asp Tyr Arg
            20                  25